(12) United States Patent
Carrano et al.

(10) Patent No.: US 8,058,502 B2
(45) Date of Patent: Nov. 15, 2011

(54) INCREASING LIFESPAN BY MODULATION OF WWP-1 AND UBC-18

(75) Inventors: Andrea C. Carrano, San Diego, CA (US); Andrew Dillin, La Jolla, CA (US); Tony Hunter, Del Mar, CA (US)

(73) Assignee: The Salk Institute for Biological Studies, La Jolla, CA (US)

( * ) Notice: Subject to any disclaimer, the term of this patent is extended or adjusted under 35 U.S.C. 154(b) by 162 days.

(21) Appl. No.: 12/228,707

(22) Filed: Aug. 15, 2008

(65) Prior Publication Data

US 2009/0083868 A1 Mar. 26, 2009

Related U.S. Application Data

(60) Provisional application No. 60/965,152, filed on Aug. 17, 2007.

(51) Int. Cl.
G01N 33/00 (2006.01)
A01K 67/00 (2006.01)
C12P 21/06 (2006.01)
C12N 5/00 (2006.01)
C07H 21/04 (2006.01)
C07K 1/00 (2006.01)

(52) U.S. Cl. .................. 800/3; 800/8; 800/9; 435/69.1; 435/320.1; 435/325; 435/455; 536/23.1; 536/23.2; 536/23.4; 530/350; 530/351

(58) Field of Classification Search ........................ 800/3
See application file for complete search history.

(56) References Cited

OTHER PUBLICATIONS

Chen et al. Oncogene 26:2386-2394; 2007.*
Carrano et al. Nature 460:396-400; 2009.*
Lucanic et al. Aging 1:751-752; 2009.*
Alcedo and Kenyon (2004) "Regulation of C. elegans longevity by specific gustatory and olfactory neurons," Neuron, 41, 45-55.
Angers et al. (2004) "The HECT domain ligase itch ubiquitinates endophilin and localizes to the trans-Golgi network and endosomal system," J Biol Chem, 279:11471-11479.
Apfeld and Kenyon (1998) "Cell nonautonomy of C. Elegans daf-2 function in the regulation of diapause and life span," Cell 95: 199-210.
Apfeld and Kenyon (1999) "Regulation of lifespan by sensory perception in Caenorhabditis elegans," Nature, 402:804-809.
Arum and Johnson (2007) "Reduced expression of the Caenorhbditis elegans p53 ortholog cep-1 results in increased longevity," J Gerontol A Biol Sci Med Sci., 62:951-959.
Bauer et al. (2005) "Neuronal expression of p53 dominant-negative proteins in adult Drosophila melanogaster extends life span," Curr Biol,15:2063-2068.
Bernassola et al. (2008) "The HECT family of E3 ubiquitin ligases: Multiple players in cancer development," Cancer Cell, 14:10-21.
Bishop and Guarente (2007) "Two neurons mediate diet-restriction-induced longevity in C. elegans," Nature, 447:545-549.
Blumenthal and Spieth (1996) "Gene structure and organization in Caenorhabditis elegans," Curr Opin Genet Dev, 6:692-698.
Blumenthal et al. (2002) "A global analysis of Caenorhabditis elegans operons," Nature. 417:851-854.
Carrano et al. 1 (1999) "SKP2 is required for ubiquitin-mediated degradation of the CDK inhibitor p27," Nat Cell Biol, 193-199.
Chen et al. (2005) "Human Kruppel-like factor 5 is a target of the E3 ubiquitin ligase WWP1 for proteolysis in epithelial cells," J Biol Chem, 280:41553-41561.
Chen et al. (2007) "The amplified WWP1 gene is a potential molecular target in breast cancer," Int J Cancer, 121(1):80-87.
Chen et al. (2007) "Ubiquitin E3 ligase WWP1 as an oncogenic factor in human prostate cancer," Oncogene, 26(16):2386-2394.
Conkright et al. (2001) "Lung Kruppel-like factor contains an autoinhibitory domain that regulates its transcriptional activation by binding WWP1, an E3 ubiquitin ligase," J Biol Chem 276:29299-29306.
Dillin et al. (2002) "Rates of behavior and aging specified by mitochondrial function during development," Science, 298:2398-2401.
Dillin et al. (2002) "Timing requirements for insulin/IGF-1 signaling in C. elegans," Science, 298:830-834.
Fang et al. (2002) "Dysregulation of T lymphocyte function in itchy mice: a role for Itch in TH2 differentiation," Nat Immunol 3, 281-287.
Fay et al. (2003) "lin-35/Rb and ubc-18, an E2 ubiquitin-conjugating enzyme, function redundantly to control pharyngeal morphogenesis in C. elegans," Development, 130:3319-3330.
Fay et al. (2004) "The coordinate regulation of pharyngeal development in C. elegans by lin-35/Rb, pha-1, and ubc-18," Dev Biol, 271:11-25.
Feng et al. (2004) "Atrophin-1-interacting protein 4/human Itch is a ubiquitin E3 ligase for human enhancer of filamentation 1 in transforming growth factor-beta signaling pathways," J Biol Chem, 279:29681-29690.
Feng et al. (2001) "Mitochondrial electron transport is a key determinant of life span in Caenorhabditis elegans," Dev Cell, 1:633-644.
Fraser et al. (2000) "Functional genomic analysis of C. elegans chromosome I by systematic RNA interference," Nature, 408(6810):325-330.
Gallagher et al. (2006) "Activation of the E3 ubiquitin ligase Itch through a phosphorylation-induce conformational change," PNAS, 103:1717-1722.
Gao et al. (2004) "Jun turnover is controlled through JNK-dependent phosphorylation of the E3 ligase Itch," Science. 306:271-275.
Gao et al. (2008) "The SCFFSN-1 ubiquitin ligase controls germline apoptosis through CEP-1/p53 in C. elegans," Cell Death and Differentiation, 15:1054-1062.
Genbank Accession No. NM_001026307, "Caenorhabditis elegans P-53-like protein family member (cep-1) (cep-1) mRNA, complete cds," Nov. 13, 2008.

(Continued)

Primary Examiner — Sumesh Kaushal
(74) Attorney, Agent, or Firm — Frommer Lawrence & Haug LLP

(57) ABSTRACT

Ubiquitin ligase wwp-1 and ubiquitin conjugating enzyme ubc-18 are identified in nematodes as mediators of dietary restriction induced longevity and therefore as targets for modulation of lifespan in animals. Methods of screening for compounds that modulate longevity by assaying wwp-1 ubiquitination pathway parameters are provided, as are related systems. In addition, methods of using wwp-1 and/or ubc-18 to modulate longevity or delay onset of age-related diseases are described.

18 Claims, 20 Drawing Sheets
(20 of 20 Drawing Sheet(s) Filed in Color)

OTHER PUBLICATIONS

Genbank Accession No. NM_001047651, *Caenorhabditis elegans* defective PHArynx development family meember (pha-4) (pha-4) mRNA, complete cds, Nov. 13, 2008.
Genbank Accession No. NM_031483, "*Homo sapiens* itchy E3 ubiquitin protein ligase homolog (mouse) (ITCH), mRNA," Mar. 4, 2010.
Genbank Accession No. NM_066140, "*Caenorhabditis elegans* ubiquitin conjugating enzyme family member (ubc-18) (ubc-18) mRNA, complete cds," Nov. 13, 2008.
Genbank Accession No. AJ000519, "*Homo sapiens* mRNA for ubiquitin-conjugating enzyme UbcH7," Oct. 7, 2008.
Genbank Accession No. NM_007013, "*Homo sapiens* WW domain containing E3 ubiquitin protein ligase 1 (WWP1), mRNA," Mar. 5, 2010.
Genbank Accession No. NM_025830, "Mus musculus WW domain containing E3 ubiquitin protein ligase 2 (Wwp2), mRNA," Mar. 12, 2010.
Genbank Accession No. NM_171831, "*Caenorhabditis elegans* WW domain protein (E3 ubiquitin ligase) family member (wwp-1) (wwp-1) mRNA, complete cds," Nov. 13, 2008.
Greer et al. (2007) "An AMPK-FOXO pathway mediates longevity induced by a novel method of dietary restriction in *C. elegans*," *Curr Biol*, 17:1646-1656.
Hansen et al. (2005) "New genes tied to endocrine, metabolic, and dietary regulation of lifespan from a *Caenorhabditis elegans* genomic RNAi screen," *PLoS Genetics*, e17.
Hansen et al. (2008) "A role for autophagy in the extension of lifespan by dietary restriction in *C. elegans*," *PLoS Genetics*, 4(2):e24.
Hoppe et al. (2000) "Activation of a membrane-bound transcription factor by regulated ubiquitin/proteasome-dependent processing," *Cell*, 102:577-586.
Huang et al. (1999) "Structure of an E6AP-UbcH7 complex: insights into ubiquitination by the E2-E3 enzyme cascade," *Science*, 286:1321-1326.
Huang et al. (2000) "A HECT domain ubiquitin ligase closely related to the mammalian protein WWP1 is essential for *Caenorhabditis elegans* embryogenesis," *Gene* 252:137-145.
Ikeda et al. (2000) "The Epstein-Barr virus latent membrane protein 2A PY motif recruits WW domain-containing ubiquitin-protein ligases," *Virology*, 268:178-191.
Ingham et al. (2005) "The Epstein-Barr virus protein, latent membrane protein 2A, co-opts tyrosine kinases used by the T cell receptor," *J Biol Chem*, 280:34133-34142.
Jones et al. (2006) "Regulation of adult bone mass by the zinc finger adapter protein Schnurri-3," *Science*, 312:1223-1227.
Kenyon (2001) "A conserved regulatory system for aging," *Cell*, 105:165-168.
Kimura et al. (1997) "daf-2, an insulin receptor-like gene that regulates longevity and diapause in *Caenorhabditis elegans*," *Science*, 277:942-946.
Klass (1977) "Aging in the nematode *Caenorhabditis elegans*: major biological and environmental factors influencing life span," *Mech Ageing Dev*, 6:413-429.
Laine and Ronai (2007) "Regulation of p53 localization and transcription by the HECT domain E3 ligase WWP1," *Oncogene*, 26:1477-1483.
Lakowski and Hekimi (1998) "The genetics of caloric restriction in *Caenorhabditis elegans*," *PNAS*, 95:13091-13096.
Lallemand et al. (2005) "AIP4 restricts transforming growth factor-beta signaling through a ubiquitination-independent mechanism," *J Biol Chem* 280:27645-27653.
Lee et al. (2003) "A systematic RNAi screen identifies a critical role for mitochondria in *C.elegans* longevity," *Nat. Genet.*, 33:40-48.
Leverson et al. (2000) "The APC11 RING-H2 finger mediates E2-dependent ubiquitination," *Mol Biol Cell*, 11:2315-2325.
Lin et al. (2001) "Regulation of the *Caenorhabditis elegans* longevity protein DAF-16 by insulin/IGF-1 and germline signaling," *Nat Genet*, 28:139-145.

Mosser et al. (1998) "Physical and functional interactions between the transactivation domain of the hematopoietic transcription factor NF-E2 and WW domains," *Biochemistry*, 37:13686-13695.
Ogg et al. (1997) "The Fork head transcription factor DAF-16 transduces insulin-like metabolic and longevity signals in *C. elegans*," *Nature*, 389, 994-999.
Oh et al (2005) "JNK regulates lifespan in *Caenorhabditis elegans* by modulating nuclear translocation of forkhead transcription factor/DAF-16," *PNAS*, 102(12:4494-4499.
Panowski et al. (2007) "PHA-4/Foxa mediates diet-restriction-induced longevity of *C. elegans*," *Nature*, 447:550-555.
Parkes et al. (1998) "Extension of *Drosophila* lifespan by overexpression of human SOD1 in motorneurons," *Nat Genet*, 19:171-174.
Pickart (2001) Mechanisms underlying ubiquitination. *Annu Rev Biochem*, 70, 503-533.
Pirozzi et al. (1997) "Identification of novel human WW domain-containing proteins by cloning of ligand targets," *J Biol Chem*, 272:14611-14616.
Qiu and Fay (2006) "ARI-1, an RBR family ubiquitin-ligase, functions with UBC-18 to regulate pharyngeal development in *C. elegans*," *Dev Biol*, 291:239-352.
Qiu et al. (2000) "Recognition and ubiquitination of Notch by Itch, a hect-type E3 ubiquitin ligase," *J Biol Chem*, 275:35734-35737.
Rogina and Helfand (2004) "Sir2 mediates longevity in the fly through a pathway related to calorie restriction," *PNAS*, 101:15998-16003.
Rossi et al. (2005) "The ubiquitin-protein ligase Itch regulates p73 stability," *EMBO J.*, 24:836-848.
Rossi et al. (2006) "Itch/AIP4 associates with and promotes p63 protein degradation," *Cell Cycle*, 5:1816-1822.
Rossi et al. (2006) "The E3 ubiquitin ligase Itch controls the protein stability of p63," *PNAS*, 103:12753-12758.
Rual et al. (2004) "Toward improving *Caenorhabditis elegans* phenome mapping with an ORFeome-based RNAi library," *Genome Res.*,14(10B):2162-2168.
Sieburth et al. (2005) "Systematic analysis of genes required for synapse structure and function," *Nature*, 436:510-517.
Tanida et al. (2008) "LC3 and autophagy," *Methods Mol Bio*, 445:77-88.
Tissenbaum and Guarente (2001) "Increased dosage of a sir-2 gene extends lifespan in *Caenorhabditis elegans*," *Nature*, 410:227-230.
Traweger et al. (2002) "The tight junction-specific protein occludin is a functional target of the E3 ubiquitin-protein ligase itch," *J Biol Chem*, 277:10201-10208.
Verdecia et al. (2003) "Conformational Flexibility Underlies Ubiquitin Ligation Mediated by the WWP1 Hect Domain E3 Ligase," *Mol Cell*, 11:249-259.
Wang et al. (2003) "JNK signaling confers tolerance to oxidative stress and extends lifespan in *Drosophila*," *Dev Cell*, 5:811-816.
Weissman (2001) "Themes and variations on ubiquitylation," *Nat Rev Mol Cell Biol*, 2:69-78.
Wolff et al. (2006) "SMK-1, an essential regulator of DAF-16-mediated longevity," *Cell*, 124:1039-1053.
Wolkow et al. (2000) "Regulation of *C. elegans* life-span by insulin-like signaling in the nervous system," *Science*, 290:147-150.
WormBase, "Strain report for RB1178", www.wormbase.org/db/gene/strain?name=RB1178;class=Strain, accessed Apr. 22, 2010.
WormBase, "Variation report for: ku354," www.wormbase.org/db/gene/variation?name=ku354, accessed Apr. 22, 2010.
Xia et al. (2003) "Enhancement of BRCA1 E3 ubiquitin ligase activity through direct interaction with the BARD1 protein," *J Biol Chem*,278:5255-5263.
Xu et al. (2004) "WWP2, an E3 ubiquitin ligase that targets transcription factor Oct-4 for ubiquitination," *J Biol Chem*, 279:23495-23503.
Zhang et al. (2004) "WWP1-dependent ubiquitination and degradation of the lung Kruppel-like factor KLF2," *Biochem Biophys Res Commun*, 316:139-148.

* cited by examiner

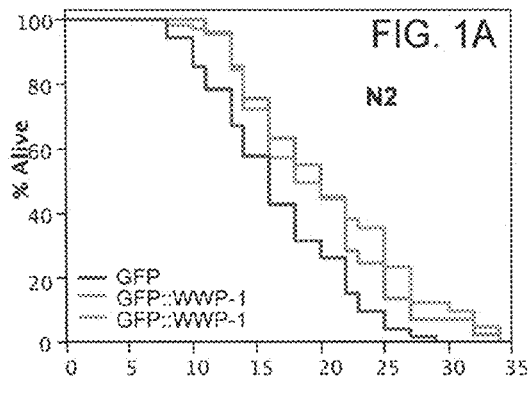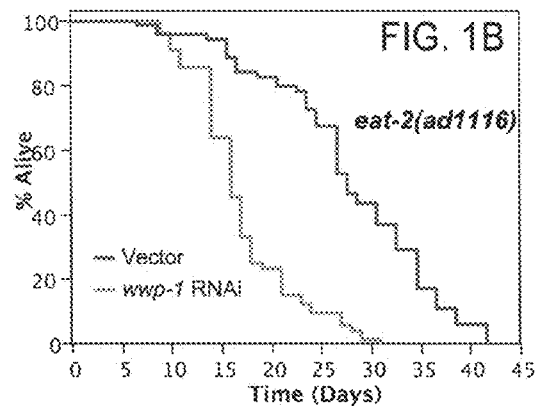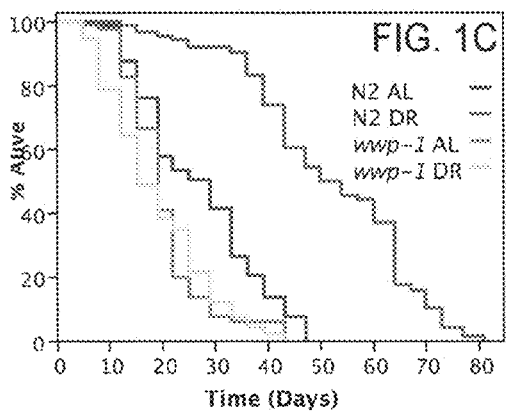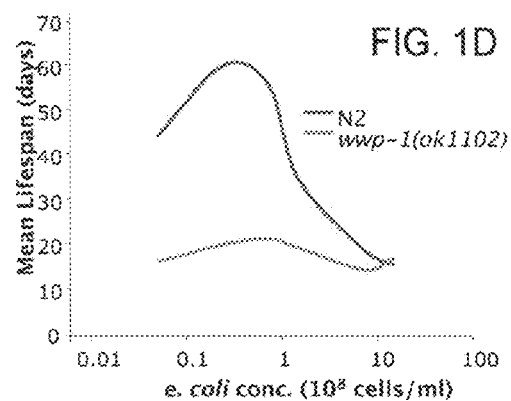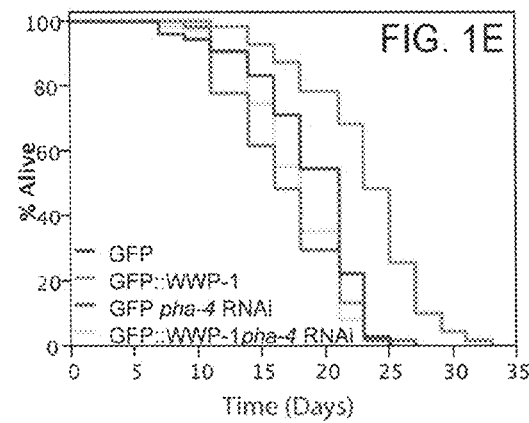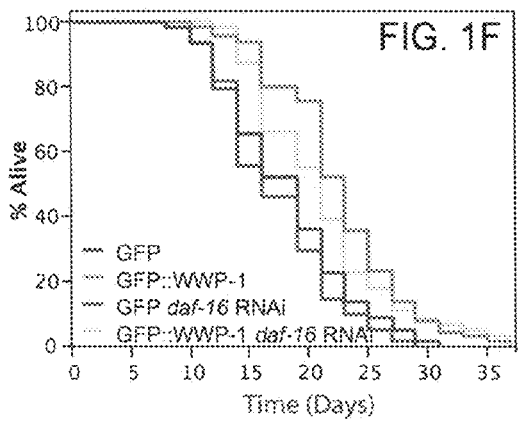

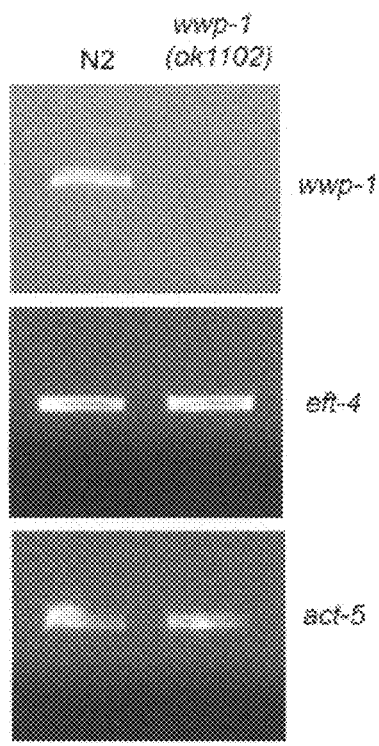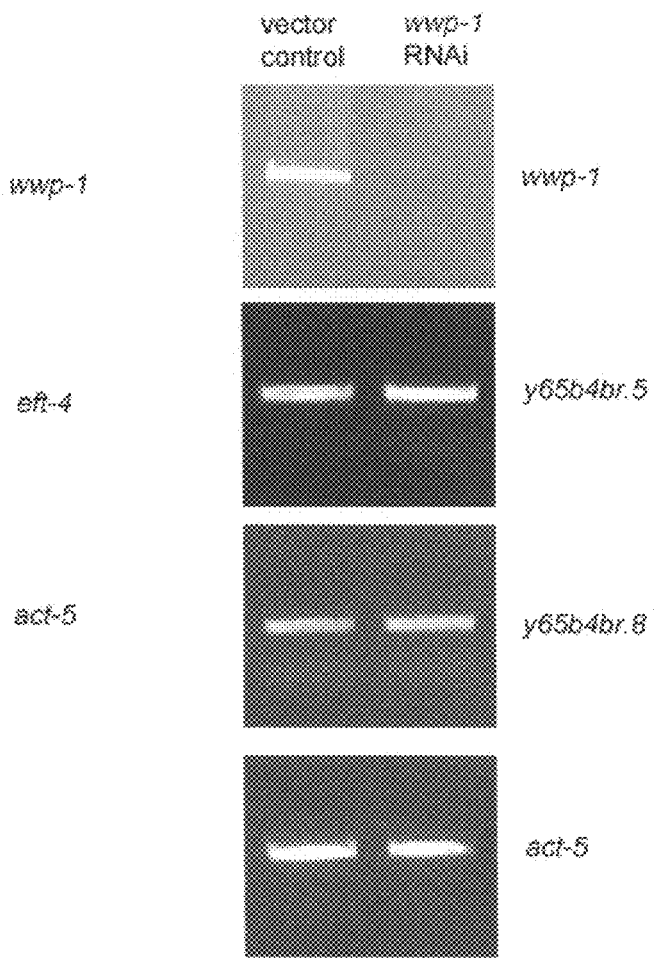

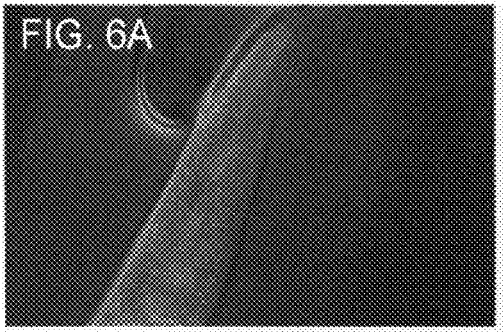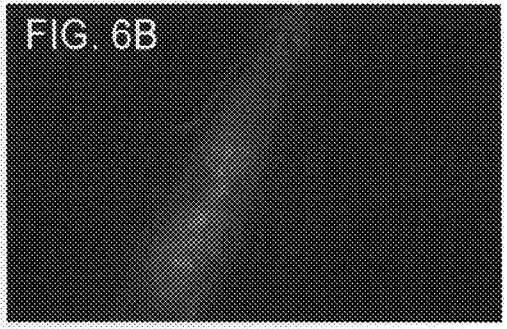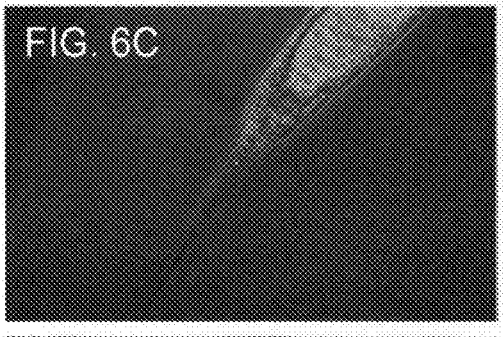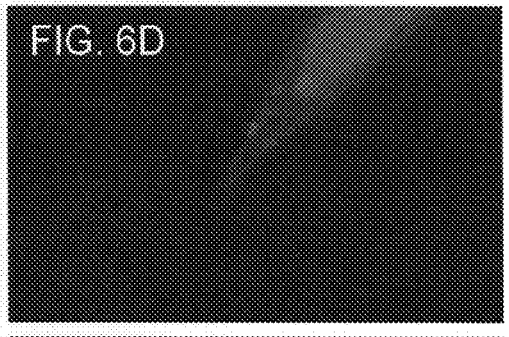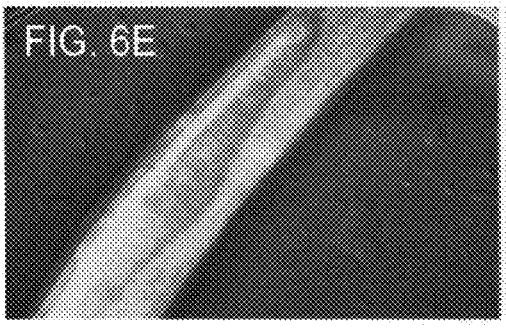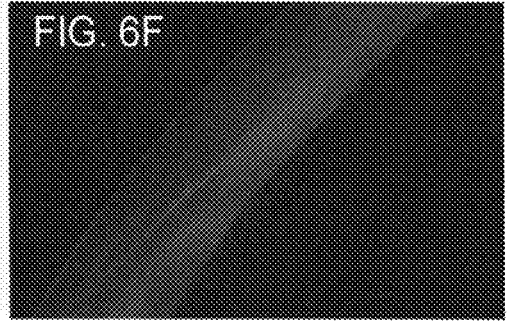

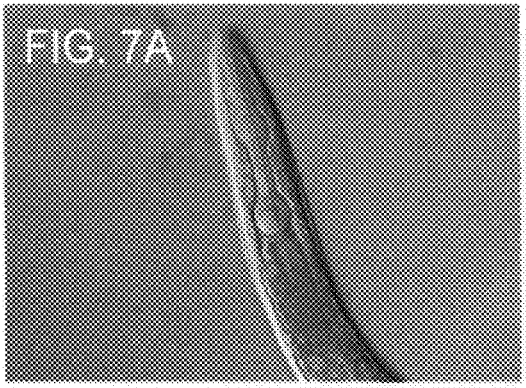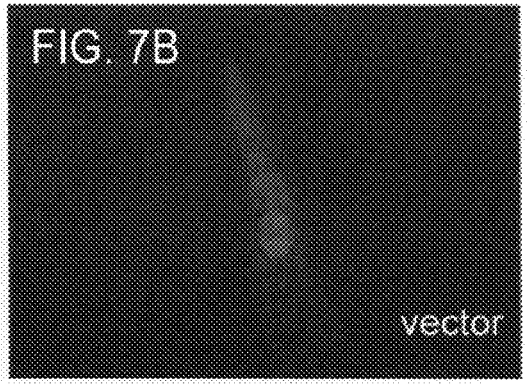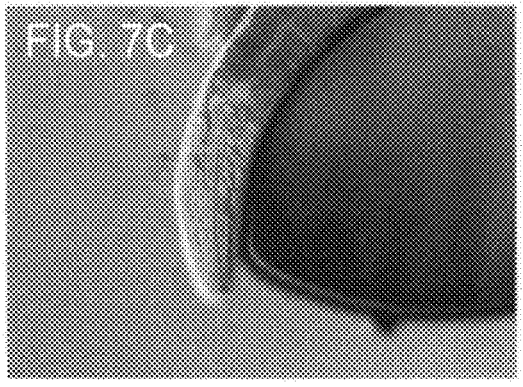

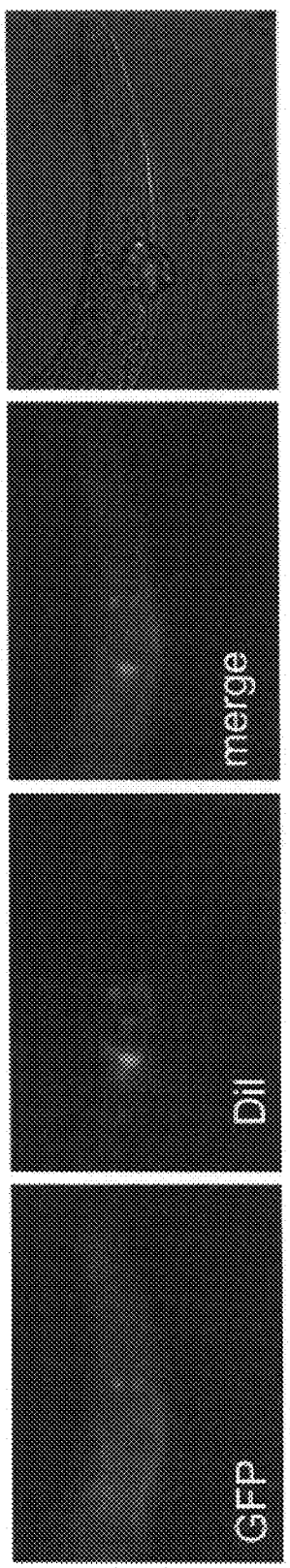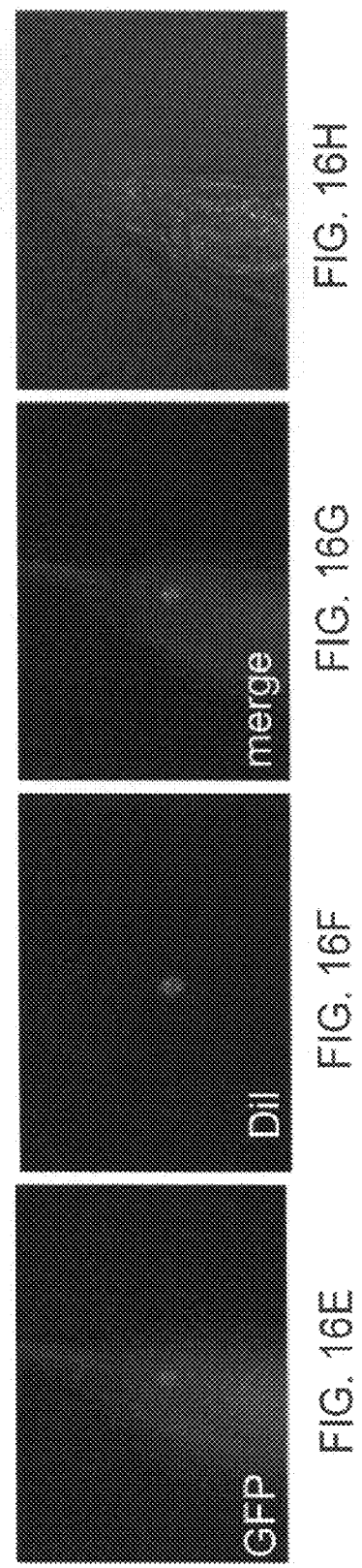

SEQUENCE LISTING

```
<160> NUMBER OF SEQ ID NOS: 14

<210> SEQ ID NO 1
<211> LENGTH: 34
<212> TYPE: DNA
<213> ORGANISM: Artificial
<220> FEATURE:
<223> OTHER INFORMATION: synthetic oligonucleotide primer

<400> SEQUENCE: 1
tggatgaact atacaaagaa ttccaactga gcgc                                    34

<210> SEQ ID NO 2
<211> LENGTH: 34
<212> TYPE: DNA
<213> ORGANISM: Artificial
<220> FEATURE:
<223> OTHER INFORMATION: synthetic oligonucleotide primer

<400> SEQUENCE: 2
gcgctcagtt ggaattcttt gtatagttca tcca                                    34

<210> SEQ ID NO 3
<211> LENGTH: 28
<212> TYPE: DNA
<213> ORGANISM: Artificial
<220> FEATURE:
<223> OTHER INFORMATION: synthetic oligonucleotide primer

<400> SEQUENCE: 3
gctctagact tgtttcctga tgaccttg                                           28

<210> SEQ ID NO 4
<211> LENGTH: 27
<212> TYPE: DNA
<213> ORGANISM: Artificial
<220> FEATURE:
<223> OTHER INFORMATION: synthetic oligonucleotide primer

<400> SEQUENCE: 4
cgggatcctc gatcatgaaa ctggctg                                            27

<210> SEQ ID NO 5
<211> LENGTH: 30
<212> TYPE: DNA
<213> ORGANISM: Artificial
<220> FEATURE:
<223> OTHER INFORMATION: synthetic oligonucleotide primer
```

-continued

```
<400> SEQUENCE: 5
atggctcgta atgaaccatc atctcagcag                                       30

<210> SEQ ID NO 6
<211> LENGTH: 30
<212> TYPE: DNA
<213> ORGANISM: Artificial
<220> FEATURE:
<223> OTHER INFORMATION: synthetic oligonucleotide primer

<400> SEQUENCE: 6
ctactcgttt ccaaatcctt ccgtcatctc                                       30

<210> SEQ ID NO 7
<211> LENGTH: 33
<212> TYPE: DNA
<213> ORGANISM: Artificial
<220> FEATURE:
<223> OTHER INFORMATION: synthetic oligonucleotide primer

<400> SEQUENCE: 7
ccacggtcgc atacggcctt caatcgactc gac                                   33

<210> SEQ ID NO 8
<211> LENGTH: 33
<212> TYPE: DNA
<213> ORGANISM: Artificial
<220> FEATURE:
<223> OTHER INFORMATION: synthetic oligonucleotide primer

<400> SEQUENCE: 8
gtcgagtcga ttgaaggccg tatgcgaccg tgg                                   33

<210> SEQ ID NO 9
<211> LENGTH: 792
<212> TYPE: PRT
<213> ORGANISM: Caenorhabditis elegans

<400> SEQUENCE: 9
```

Met Ala Arg Asn Glu Pro Ser Ser Gln Gln Pro Ser Ser Gly Ser
1               5                   10                  15

Asn Gly Thr Pro Ala Gln Gln Asn Gly Ser Ala Lys Pro Ser Lys Val
            20                  25                  30

Thr Val Lys Val Val Asn Ala Ser Phe Thr Lys Ala Ala Asp Cys Tyr
        35                  40                  45

Val Glu Ile Thr Ser Asp Thr Ser Ala Ala Pro Lys Lys Thr Thr
    50                  55                  60

Val Lys Lys Lys Thr Met Ala Pro Glu Trp Asn Glu His Leu Asn Val
65                  70                  75                  80

His Ala Asn Glu Ser Ser Thr Ile Ser Phe Arg Leu Leu Gln Lys Ala
                85                  90                  95

Lys Leu Phe Asp Asp Thr Cys Leu Gly Met Ala Lys Leu Lys Leu Ser
            100                 105                 110

Ser Leu Thr Arg Asn Glu Asn Gly Glu Phe Lys Asn Asp Ile Asn Asn
        115                 120                 125

Ile Ser Leu Leu Ala Lys Asp Ser Ser Lys Ile Gly Thr Leu Asn Ile
    130                 135                 140

Ile Phe Ser Gly Tyr Pro Glu Arg Lys Arg Ser Ala Gly Val Arg
145                 150                 155                 160

Ala Glu Thr Ala Ala Ser Ala Ser Ser Glu Ala Ser Thr Ser Asn Gly
                165                 170                 175

-continued

Val Ala Thr Ser Ser Ala Arg Arg Pro Ala Thr Ala Lys Arg Asp
                180                 185                 190

Thr Leu Ala Ala Pro Thr Ser Thr Ala Ala Ala Ala Ala Ala Thr
            195                 200                 205

Ala Gly Gly Thr Pro Ala Ala Gly Ala Glu Glu Gln Leu Pro Asp Gly
210                 215                 220

Trp Glu Met Arg Phe Asp Gln Tyr Gly Arg Lys Tyr Tyr Val Asp His
225                 230                 235                 240

Thr Thr Lys Ser Thr Thr Trp Glu Arg Pro Ser Thr Gln Pro Leu Pro
                245                 250                 255

Gln Gly Trp Glu Met Arg Arg Asp Pro Arg Gly Arg Val Tyr Tyr Val
                260                 265                 270

Asp His Asn Thr Arg Thr Thr Thr Trp Gln Arg Pro Thr Ala Asp Met
            275                 280                 285

Leu Glu Ala His Glu Gln Trp Gln Ser Gly Arg Asp Gln Ala Met Leu
            290                 295                 300

Gln Trp Glu Gln Arg Phe Leu Leu Gln Gln Asn Asn Phe Ser Ala Asp
305                 310                 315                 320

Asp Pro Leu Gly Pro Leu Pro Glu Gly Trp Glu Lys Arg Gln Asp Pro
                325                 330                 335

Asn Thr Ser Arg Met Tyr Phe Val Asn His Val Asn Arg Thr Thr Gln
                340                 345                 350

Trp Glu Asp Pro Arg Thr Gln Gly Gly Ser Asp Gln Pro Leu Pro Asp
                355                 360                 365

Gly Trp Glu Met Arg Phe Thr Glu Gln Gly Val Pro Phe Phe Ile Asp
370                 375                 380

His Gln Ser Lys Thr Thr Thr Tyr Asn Asp Pro Arg Thr Gly Lys Pro
385                 390                 395                 400

Val Gly Pro Leu Gly Val Val Gly Val Gln Met Ala Met Glu Lys Ser
                405                 410                 415

Phe Arg Trp Lys Ile Ala Gln Phe Arg Tyr Leu Cys Leu Ser Asn Ser
                420                 425                 430

Val Pro Asn His Val Lys Ile Thr Val Ser Arg Asn Asn Val Phe Glu
                435                 440                 445

Asp Ser Phe Gln Glu Ile Met Arg Lys Asn Ala Val Asp Leu Arg Arg
                450                 455                 460

Arg Leu Tyr Ile Gln Phe Arg Gly Glu Glu Gly Leu Asp Tyr Gly Gly
465                 470                 475                 480

Val Ala Arg Glu Trp Phe Phe Leu Leu Ser His Glu Val Leu Asn Pro
                485                 490                 495

Met Tyr Cys Leu Phe Met Tyr Ala Gly Asn Asn Tyr Ser Leu Gln
                500                 505                 510

Ile Asn Pro Ala Ser Phe Val Asn Pro Asp His Leu Lys Tyr Phe Glu
                515                 520                 525

Tyr Ile Gly Arg Phe Ile Ala Met Ala Leu Phe His Gly Lys Phe Ile
            530                 535                 540

Tyr Ser Gly Phe Thr Met Pro Phe Tyr Lys Lys Met Leu Asn Lys Lys
545                 550                 555                 560

Ile Val Leu Lys Asp Ile Glu Gln Val Asp Ser Glu Ile Tyr Asn Ser
                565                 570                 575

Leu Met Trp Ile Lys Asp Asn Asn Ile Asp Glu Cys Asp Met Glu Leu
            580                 585                 590

Tyr Phe Val Ala Asp Tyr Glu Leu Leu Gly Glu Leu Lys Thr Tyr Glu

```
                595                 600                 605
Leu Lys Glu Gly Gly Thr Glu Ile Ala Val Thr Glu Glu Asn Lys Leu
    610                 615                 620

Glu Tyr Ile Glu Leu Leu Val Glu Trp Arg Phe Asn Arg Gly Val Glu
625                 630                 635                 640

Gln Gln Thr Lys Ala Phe Phe Thr Gly Phe Asn Ser Val Phe Pro Leu
                645                 650                 655

Glu Trp Met Gln Tyr Phe Asp Glu Arg Glu Leu Glu Leu Leu Leu Cys
            660                 665                 670

Gly Met Gln Asp Val Asp Val Asp Asp Trp Gln Arg Asn Thr Val Tyr
        675                 680                 685

Arg His Tyr Ala Pro Gln Ser Lys Gln Val Thr Trp Phe Trp Gln Trp
    690                 695                 700

Val Arg Ser Leu Asp Gln Glu Lys Arg Ala Arg Leu Leu Gln Phe Val
705                 710                 715                 720

Thr Gly Thr Cys Arg Val Pro Val Gly Gly Phe Ser Glu Leu Met Gly
                725                 730                 735

Ser Thr Gly Pro Gln Leu Phe Cys Ile Glu Arg Val Gly Lys Glu Asn
            740                 745                 750

Trp Leu Pro Arg Ser His Thr Cys Phe Asn Arg Leu Asp Leu Pro Pro
        755                 760                 765

Tyr Arg Ser Tyr Asp Gln Leu Val Glu Lys Leu Ser Met Ala Ile Glu
    770                 775                 780

Met Thr Glu Gly Phe Gly Asn Glu
785                 790

<210> SEQ ID NO 10
<211> LENGTH: 2395
<212> TYPE: DNA
<213> ORGANISM: Caenorhabditis elegans

<400> SEQUENCE: 10
ccagtttcat gatcgaatgg ctcgtaatga accatcatct cagcagccga gtagttccgg      60
gagtaatgga actccagcac aacaaaacgg gtcggcaaaa ccatcaaaag tcacagtaaa     120
agtcgtcaac gcgtcgttca ccaaggcagc cgactgctat gtcgaaatca cgagtgacac     180
gtcatcggcg gcgccaaaaa agacgactgt aagaagaag acgatggcgc ccgagtggaa      240
tgaacatctc aacgttcatg caaatgaatc ttcgacaatt tcgtttcgtc tattgcaaaa     300
agccaagcta ttcgatgaca cgtgtctagg gatggcgaag ctgaagcttt cgagtctcac     360
aagaaatgag aatggagagt tcaaaaacga catcaacaat atatctttgc tggccaaaga     420
ctcctcgaaa tcggaactc tcaacataat tttctccgga tatccagagc ggaaacgaag      480
aagcgcagga gtacgagctg aaaccgccgc gtctgcaagt tcagaggcat ccacgtcaaa     540
tggcgttgcc acgtcatcct cggcgcggag accggcgaca gcgaagcgtg acactttggc     600
ggctccaacg agtaccgcag cggcggcagc agcagcaaca gcaggcggca ccccggccgc     660
cggagcagaa gaacagcttc ccgatggatg ggagatgcgt ttcgatcaat acggacgcaa     720
gtactacgtg gatcacacca ccaagagcac cacgtgggaa cgcccgtcta ctcagccatt     780
gccacaggga tgggaaatgc gaagagatcc gagaggaaga gtgtattacg tggatcacaa     840
cacgcgcacg accacctggc aacgaccgac agccgatatg cttgaagcac acgaacaatg     900
gcaatcggga agagatcagg cgatgcttca atgggaacaa cgtttccttc tccagcagaa     960
caactttagc gccgacgatc cactcggacc attgcccgaa ggatgggaga agcgtcagga    1020
```

```
tccgaatacg tcgagaatgt actttgtgaa tcatgtaaat agaacgacac aatgggaaga   1080
tccgagaaca cagggaggct ccgaccaacc tcttccggat ggttgggaaa tgcgattcac   1140
cgagcaaggc gttccattct tcatcgatca ccagtctaaa accaccacct ataatgatcc   1200
aagaaccgga aaaccgtcg gcccgctcgg cgtcgtcggt gttcaaatgg ccatggagaa   1260
gagtttccgg tggaaaattg cacaattcag atatttatgc ttgtcaaaca gtgtgcctaa   1320
tcatgtcaaa atcacagtat cccgtaataa cgtgttcgaa gactcattcc aagaaattat   1380
gcgtaaaaat gcagtcgatc tacgccggcg gctgtacatt caattccgag cgaagaggg   1440
tctcgactat ggaggtgtcg ccagagaatg gttcttcctg ctgtcgcacg aagtgttgaa   1500
tccaatgtat tgcctattca tgtatgctgg taataacaat tatagtcttc aaatcaatcc   1560
agcttcattt gttaacccgg atcatcttaa gtatttcgag tatattggac gattcattgc   1620
catggcgcta ttccacggga aattcatcta cagcggtttc acgatgccat tctacaaaaa   1680
gatgctcaac aagaagattg ttttaaagga cattgaacaa gtcgattcgg aaatttataa   1740
ttcattgatg tggatcaagg ataacaatat cgatgaatgc gatatggagc tctattttgt   1800
tgccgattac gagctgctcg gcgagctcaa gacttatgag cttaaggagg cggtacaga   1860
gattgctgtt accgaggaga ataagcttga atacatcgaa ctgctcgttg agtggcgctt   1920
caatcgcggt gtcgaacaac agacaaaagc cttcttcacc ggcttcaact cggtcttccc   1980
gttggaatgg atgcagtatt tcgatgaaag agagctcgag ctgttgctct gcggaatgca   2040
ggacgttgat gtggacgatt ggcagagaaa tactgtctac agacattatg ctccacagag   2100
caagcaggta acctggttct ggcaatgggt tcgaagtctg gaccaagaaa aacgtgcccg   2160
gctcctacaa ttcgtcacag gaacgtgccg tgtgccagtc ggtggattt ccgagctgat   2220
gggctcgacg ggaccacaac tattctgtat cgagcgtgtc ggcaaggaga actggctccc   2280
acggtcgcat acgtgcttca atcgactcga cttgccgcca tacagaagct acgatcagct   2340
cgtcgagaag ttgagcatgg cgatcgagat gacggaagga tttggaaacg agtag        2395
```

<210> SEQ ID NO 11
<211> LENGTH: 153
<212> TYPE: PRT
<213> ORGANISM: Caenorhabditis elegans

<400> SEQUENCE: 11

```
Met Ser Ala Thr Arg Arg Leu Gln Lys Glu Leu Gly Asp Leu Lys Asn
 1               5                  10                  15

Cys Gly Val Lys Ala Tyr Glu Asn Val Glu Cys Glu Glu Thr Asn Leu
            20                  25                  30

Leu Lys Trp Thr Val Leu Leu Ile Pro Asp Lys Glu Pro Tyr Asn Lys
        35                  40                  45

Gly Ala Phe Lys Val Gly Ile Thr Phe Pro Val Asp Tyr Pro Phe Lys
    50                  55                  60

Pro Pro Lys Val Ala Phe Glu Thr Lys Ile Tyr His Pro Asn Val Asp
65                  70                  75                  80

Glu Glu Gly Lys Phe Cys Leu Pro Ile Val Thr Ala Glu Asn Trp Lys
                85                  90                  95

Pro Ala Thr Lys Thr Glu Gln Val Met Met Ala Leu Leu Ser Leu Ile
            100                 105                 110

Asn Glu Pro Glu Pro Ser His Pro Ile Arg Ala Asp Val Ala Glu Glu
        115                 120                 125

Phe Gln Lys Asp His Lys Lys Phe Met Lys Thr Ala Glu Glu His Thr
    130                 135                 140
```

Arg Lys His Ala Glu Lys Arg Pro Glu
145                 150

<210> SEQ ID NO 12
<211> LENGTH: 648
<212> TYPE: DNA
<213> ORGANISM: Caenorhabditis elegans

<400> SEQUENCE: 12

```
tgttaaccca actagagcgt ttatatcaac atgtcagcga cacggcgtct tcagaaggaa      60
ctcggtgatc tcaaaaactg tggagtgaag gcgtacgaga atgttgagtg cgaggagaca     120
aatctcttga atggacagt tctccttatc ccagataagg agccatacaa caaaggtgcg     180
ttcaaagttg gaatcacgtt ccccgttgac tacccattca agccaccaaa ggtcgcgttc     240
gagaccaaga tttaccatcc aaatgttgat gaggaaggaa agttctgtct tccaattgtg     300
acagctgaaa actggaagcc agctaccaag accgagcaag tgatgatggc cttgctgtca     360
ctgatcaacg aaccagaacc atcccatcca attcgtgccg acgttgccga ggagttccaa     420
aaggatcaca aaaagttcat gaagaccgcc gaggagcaca ctcgaaagca cgccgaaaag     480
cggcctgaat aggcgccaag agctcagatc taaattcgtt cgatttcgag ttcatcttat     540
gtttcttttc tgtatttatc atattctcgt tttcaccgtc ccaatcattc aatccacttc     600
aatttcatcc aattccaacc tgatttccca catccaaagc aagaactg                  648
```

<210> SEQ ID NO 13
<211> LENGTH: 411
<212> TYPE: PRT
<213> ORGANISM: Caenorhabditis elegans

<400> SEQUENCE: 13

Met Asn Ala Gln Asp Tyr Leu Pro Thr Tyr Ser Asn Thr Thr Leu Asn
1               5                   10                  15

Tyr Gln Pro Tyr Gln Tyr Gln Thr Ala Ala Asn Gly Leu Leu Asn Tyr
            20                  25                  30

Asn Asn Tyr Ser Gln Tyr Ala Thr Ala Asn Gln Leu Gly Ser Asn Tyr
        35                  40                  45

Ile Ser Pro Ala Asn Phe Met Gln Gly Gly Ile Ser Pro Leu Gly
    50                  55                  60

Phe Thr Thr Gly Thr Thr Gly Ala Thr Thr Ala Ala Ala Ser Val Ala
65                  70                  75                  80

Thr Ser Ser Ala Ser Ala Val Ile Gly Arg Ser Asn Gly Arg Ser Ser
                85                  90                  95

Ser Thr Val Ala Ala Ser Pro Ala Asp Arg Ser Tyr Ser Gly Val Ser
            100                 105                 110

Gly Gly Gln Gly Gln Glu Leu Thr Ile Gln Glu Phe Glu Thr Val Thr
        115                 120                 125

Glu Lys Ile Arg Arg His Gly Thr Tyr Gly Gln Ser Lys Pro Pro Tyr
    130                 135                 140

Ser Tyr Ile Ser Leu Ile Thr Met Ala Ile Gln Lys Ser Asn Ser Arg
145                 150                 155                 160

Gln Leu Thr Leu Ser Glu Ile Tyr Asn Trp Ile Met Asp Leu Phe Pro
                165                 170                 175

Tyr Tyr Gln Asn Asn Gln Gln Arg Trp Gln Asn Ser Ile Arg His Ser
            180                 185                 190

Leu Ser Phe Asn Asp Cys Phe Val Lys Val Ala Arg Ser Pro Asp Lys
        195                 200                 205

```
Pro Gly Lys Gly Ser Phe Trp Thr Leu His Glu His Cys Gly Asn Met
    210                 215                 220
Phe Glu Asn Gly Cys Tyr Leu Arg Arg Gln Lys Arg Phe Lys Val Lys
225                 230                 235                 240
Glu Arg Glu Pro Ser Arg Lys Lys Arg Asn Ala Asn Ser Gln Gln Leu
                245                 250                 255
His Gln Gln His Ile Pro Lys Met Glu Ile Lys Glu Glu Asp Pro
            260                 265                 270
Thr Ser Ile Thr Thr Ser Ser Leu Gly Ala Tyr Ser Leu Ile Pro
    275                 280                 285
Gln Ile Ser Thr Lys Lys Glu Ile Lys Glu Glu Leu Lys Ala Val Gln
    290                 295                 300
Asp Ala Thr Ala Ala Ala Asn Leu Gly Leu Ile Asp Pro Ser Gly
305                 310                 315                 320
Thr Pro Ser Ala Val Asn His Ser Gln Pro Thr Ser Val Ile Ser Ser
                325                 330                 335
Val Gly Thr Leu Gly Thr Thr Gln Ala Gln Met Thr Leu Asn Gly Gln
            340                 345                 350
Tyr Ala Ser Pro Tyr Leu Tyr Ser Ser Asp Phe Ala Thr Ile Leu Pro
    355                 360                 365
Gln Ser Gln Asn Phe Leu Asn Asn Thr Leu Tyr Asn Thr Thr Ser Ser
    370                 375                 380
Tyr Pro Gly Ile Asp Tyr Thr Asn Gly Val Tyr Gln Asn Thr Leu Tyr
385                 390                 395                 400
Ser Ser Thr Asn Pro Asn Ser Ala Ala Asn Leu
                405                 410

<210> SEQ ID NO 14
<211> LENGTH: 1239
<212> TYPE: DNA
<213> ORGANISM: Caenorhabditis elegans

<400> SEQUENCE: 14
gccatgaacg ctcaggacta tctgccgacg tattctaata ctacgttaaa ctaccaacca     60
tatcagtacc agactgctgc caatggactt ctgaactaca caactacag ccagtatgcc    120
actgctaatc agctcggatc gaactacatc agcccagcca atttcatgca aggaggagga    180
atttcacctc ttggttttac cactggcacc accggagcca ccacagcggc cgcttccgtg    240
gccacgtcgt ccgcctcagc ggtcatcgga agaagcaatg gacgatcaag ctcgacggtt    300
gctgcatcgc cagccgatag gtcttattct ggtgtaagcg gagggcaagg ccaagaactc    360
acgattcagg aatttgaaac tgtcacggaa aagatcagaa gacatggaac ttatggacaa    420
tcgaaacctc catactctta cattagctta attactatgg caattcaaaa gtctaattct    480
agacaattga cattgtctga aatctacaat tggatcatgg atttgttccc ttactatcag    540
aacaatcaac aaagatggca aaactcaatt cgccactccc tctccttcaa tgattgcttt    600
gtaaaggttg ccaggtcccc tgacaagcct ggaaagggat ccttctggac tcttcacgag    660
cactgtggga atatgtttga gaatggatgc tacctccgta ggcagaagag attcaaggtc    720
aaggaacgtg agccatcgag aaagaagaga aatgccaact cccaacaatt gcatcaacaa    780
caacacattc caaaaatgga aatcaaagaa gaggatccaa catccatcac gaccacatca    840
tcacttggtg cttattctct gatccctcaa atttctacaa agaaggagat caaggaagag    900
ctgaaagctg tgcaagatgc aactgcagct gctgccaatc ttggcctaat tgacccatcg    960
```

-continued

| | | | | |
|---|---|---|---|---|
| ggaacgccgt | cggctgttaa | tcacagtcaa | cctacttcag tgatctcaag | tgttggcaca 1020 |
| ctaggaacca | cgcaagcaca | gatgacactc | aatggtcaat acgcgtctcc | ttacctctac 1080 |
| agttcggatt | ttgccacaat | tctcccacaa | tcccagaatt tcctgaacaa | cacactctac 1140 |
| aacacaacga | gcagttatcc | aggaattgac | tacaccaacg gagtatacca | gaatactctt 1200 |
| tacagctcca | ccaacccgaa | ctcggccgcc | aacctataa | 1239 |

INCREASING LIFESPAN BY MODULATION OF WWP-1 AND UBC-18

CROSS-REFERENCE TO RELATED APPLICATIONS

This application is a non-provisional utility patent application claiming priority to and benefit of the following prior provisional patent application: U.S. Ser. No. 60/965,152, filed Aug. 17, 2007, entitled "INCREASING LIFESPAN BY MODULATION OF WWP-1 AND UBC-18" by Andrea C. Carrano et al., which is incorporated herein by reference in its entirety for all purposes.

STATEMENT AS TO RIGHTS TO INVENTIONS MADE UNDER FEDERALLY SPONSORED RESEARCH AND DEVELOPMENT

This invention was made with government support under Grant Nos. CA54418 and CA82683 from the United States Public Health Service. The government may have certain rights to this invention.

FIELD OF THE INVENTION

The present invention relates to the field of longevity enhancement. More specifically, the present invention includes methods for increasing lifespan, e.g., by modulating wwp-1 and/or ubc-18 expression or activity, as well as screening methods for identifying compounds that modulate longevity.

BACKGROUND OF THE INVENTION

Aging in mammals or other animals can have profound negative effects on the cognitive and motor functions of the subject. Genes that regulate the aging pathways and genes that could slow, pause, or decrease the effects of aging and/or increase lifespan are of great interest, because of their potential to increase longevity or enhance quality of life during the later part of the subject's lifespan.

Studies in model organisms have shown that the aging process is regulated by conserved mechanisms. For example, lifespan extension has been achieved in multiple animal systems by inactivation of the insulin-like receptor signal transduction pathway (Kenyon (2001) "A conserved regulatory system for aging" Cell 105:165-8). Reduction of mitochondrial function has also been shown to increase lifespan. For example, mutations in the iron sulfur component of complex III, isp-1, increase longevity by decreasing oxygen consumption (Dillin et al. (2002) Science 298:2398-401, Feng et al. (2001) Dev Cell 1:633-644, and Lee et al. (2003) Nat. Genet. 33:40-48).

In addition, reduced food intake as a result of dietary restriction increases the lifespan of a wide variety of metazoans and delays the onset of multiple age-related pathologies. This is a conserved phenomenon in a number of species, e.g., yeast, worms, flies, mice, waterstriders, guppies, chickens, labradors, and rats. Dietary restriction elicits a genetically programmed response to nutrient availability that cannot be explained by a simple reduction in metabolism or slower growth of the organism.

However, although considerable progress has been made in understanding aging, there is still need for elucidation of the pathways that influence aging, as well as for novel ways to increase longevity and decrease the effects of aging.

Among other benefits, the present invention meets the above needs by providing the identity of a key pathway that mediates dietary restriction-induced longevity (the ubiquitin pathway), by providing methods for screening for modulators of aging and longevity, and by providing methods for regulating longevity. A complete understanding of the invention will be obtained upon review of the following.

SUMMARY OF THE INVENTION

Ubiquitin pathway components wwp-1 and ubc-18 are shown herein to mediate dietary restriction induced longevity. The connection between these genes and longevity is used to provide screening methods, e.g., whole organism and cell-based methods, for identifying compounds that modulate longevity and delay onset of age-related diseases and conditions. Related screening systems are also provided, as are compounds identified as longevity modulators using the methods and/or systems herein. In addition, methods are presented for using these genes to modulate longevity in an animal and to delay onset of age-related diseases.

One general class of embodiments provides methods of screening for a modulator of longevity in which a non-human animal that exhibits artificially altered expression or activity of wwp-1 or a homolog thereof and/or of ubc-18 or a homolog thereof is provided. A test compound is administered to the non-human animal, and a wwp-1 ubiquitination pathway parameter in the non-human animal is assayed. A change in the wwp-1 ubiquitination pathway parameter indicates that the test compound modulates longevity.

In one class of embodiments, the non-human animal exhibits reduced expression or activity of wwp-1 or the homolog thereof and/or reduced expression or activity of ubc-18 or the homolog thereof. In one embodiment, the non-human animal expresses a dominant negative form of wwp-1 or the homolog thereof or a dominant negative form of ubc-18 or the homolog thereof. In another class of embodiments, the non-human animal overexpresses wwp-1 or the homolog thereof and/or ubc-18 or the homolog thereof. In one class of embodiments, the cell expresses a fusion protein comprising GFP or a homolog thereof and either wwp-1 or a homolog thereof or ubc-18 or a homolog thereof; changes in expression of wwp-1 or ubc-18 can thus be easily monitored by monitoring expression of the GFP moiety in the fusion protein.

Suitable wwp-1 ubiquitination pathway parameters that can be assayed include, but are not limited to, one or more of lifespan, an activity or expression level of wwp-1 or the homolog thereof, an activity or expression level of ubc-18 or the homolog thereof, an activity or expression level of pha-4 or a homolog thereof, post-translational modification state of wwp-1 or the homolog thereof, post-translational modification state of a substrate of wwp-1 or the homolog thereof (e.g., cep-1, pha-4, skn-1b, or other substrate described herein or known in the art), and level of autophagy. Compounds that increase longevity or delay onset of age-related diseases can be identified, for example, as those that increase lifespan of the non-human animal; increase expression of wwp-1 or the homolog thereof, ubc-18 or the homolog thereof, or pha-4 or the homolog thereof; increase activity of wwp-1 or the homolog thereof, ubc-18 or the homolog thereof, or pha-4 or the homolog thereof; increase phosphorylation of wwp-1 or the homolog thereof, increase ubiquitination of the substrate of wwp-1 or the homolog thereof, or increase autophagy.

Non-human animals that can be employed in the screens include, but are not limited to, nematodes (e.g., *C. elegans*), flies (e.g., *Drosophila*), and typical mammalian laboratory animals such as mice, rabbits, and rats. Typically, the animals are adults. Administration of the test compound is optionally by feeding the compound to the animal. The animals are also optionally subjected to dietary restriction, e.g., reduced caloric intake, during the screen, or the compounds can be tested without any dietary restrictions in place. Exemplary test compounds include, e.g., a small molecule, a polypeptide, an antibody, a nucleic acid, an antisense molecule, or a double-stranded RNA.

A related general class of embodiments provides a system for screening for compounds that modulate longevity. The system includes an array of non-human animals in containers, a monitoring module, and a correlation module. The non-human animals exhibit artificially altered expression or activity of wwp-1 or a homolog thereof and/or of ubc-18 or a homolog thereof. The monitoring module monitors a wwp-1 ubiquitination pathway parameter of the non-human animals in the array following administration of a test compound to the animals. The correlation module correlates a change in the wwp-1 ubiquitination pathway parameter to longevity, thereby identifying the compounds that modulate longevity.

As for the methods above, suitable wwp-1 ubiquitination pathway parameters include, but are not limited to, one or more of lifespan, an activity or expression level of wwp-1 or the homolog thereof, an activity or expression level of ubc-18 or the homolog thereof, an activity or expression level of pha-4 or a homolog thereof, post-translational modification state of wwp-1 or the homolog thereof, post-translational modification state of a substrate of wwp-1 or the homolog thereof, and level of autophagy. Compounds that increase longevity or delay onset of age-related diseases can be identified, for example, as those that increase lifespan of the non-human animal; increase expression of wwp-1 or the homolog thereof, ubc-18 or the homolog thereof, or pha-4 or the homolog thereof; increase activity of wwp-1 or the homolog thereof, ubc-18 or the homolog thereof, or pha-4 or the homolog thereof; increase phosphorylation of wwp-1 or the homolog thereof, increase ubiquitination of the substrate of wwp-1 or the homolog thereof; or increase autophagy.

Non-human animals that can be employed include, but are not limited to, nematodes (e.g., *C. elegans*), flies (e.g., *Drosophila*), and typical mammalian laboratory animals such as mice, rabbits, and rats. Typically, the animals are adults. Administration of the test compound is optionally by feeding the compound to the animal. The animals are also optionally subjected to dietary restriction.

Another general class of embodiments provides methods of screening for a compound that modulates longevity in which a cell that exhibits artificially altered expression or activity of wwp-1 or a homolog thereof and/or of ubc-18 or a homolog thereof is contacted with a test agent. A wwp-1 ubiquitination pathway parameter in the cell is then assayed, and a change in the wwp-1 ubiquitination pathway parameter relative to a control sample without the test agent identifies the compound that modulates longevity. Exemplary test compounds include, e.g., a small molecule, a polypeptide, an antibody, a nucleic acid, an antisense molecule, or a double-stranded RNA.

Suitable wwp-1 ubiquitination pathway parameters that can be assayed include, but are not limited to, one or more of an activity or expression level of wwp-1 or the homolog thereof, an activity or expression level of ubc-18 or the homolog thereof, an activity or expression level of pha-4 or a homolog thereof, post-translational modification state of wwp-1 or the homolog thereof, post-translational modification state of a substrate of wwp-1 or the homolog thereof (e.g., cep-1, pha-4, skn-1b, or other substrate described herein or known in the art), and level of autophagy. Compounds that increase longevity or delay onset of age-related diseases can be identified, for example, as those that increase expression of wwp-1 or the homolog thereof, ubc-18 or the homolog thereof, or pha-4 or the homolog thereof; increase activity of wwp-1 or the homolog thereof, ubc-18 or the homolog thereof, or pha-4 or the homolog thereof; increase phosphorylation of wwp-1 or the homolog thereof; increase ubiquitination of the substrate of wwp-1 or the homolog thereof; or increase autophagy.

Yet another general class of embodiments provides methods of identifying a modulator of longevity. In the methods, a non-human animal is provided. A test compound is administered to the non-human animal, and expression or activity of wwp-1 or a homolog thereof, expression or activity of ubc-18 or a homolog thereof, and/or post-translational modification state of wwp-1 or a homolog thereof or a substrate thereof (e.g., cep-1, pha-4, skn-1b, or other substrate described herein or known in the art) in the animal is monitored. An increase in expression or activity of wwp-1 or the homolog thereof, an increase in expression or activity of ubc-18 or the homolog thereof, increased phosphorylation of wwp-1 or the homolog thereof, and/or increased ubiquitination of the substrate indicates that the test compound modulates (e.g., increases) longevity.

The animals optionally express a reporter construct that facilitates measurement of expression or activity. For example, the non-human animal can express a fusion protein comprising GFP or a homolog thereof and either wwp-1 or a homolog thereof or ubc-18 or a homolog thereof. In such embodiments, monitoring expression of wwp-1 or ubc-18 or the homolog thereof involves monitoring an optical signal from the GFP.

Non-human animals that can be employed in the screens include, but are not limited to, nematodes (e.g., *C. elegans*), flies (e.g., *Drosophila*), and typical mammalian laboratory animals such as mice, rabbits, and rats. Typically, the animals are adults. Administration of the test compound is optionally by feeding the compound to the animal. The animals are also optionally subjected to dietary restriction, e.g., reduced caloric intake, during the screen, or the compounds can be tested without any dietary restrictions in place. Exemplary test compounds include, e.g., a small molecule, a polypeptide, an antibody, a nucleic acid, an antisense molecule, or a double-stranded RNA.

A related general class of embodiments provides a system for screening for compounds that modulate longevity. In this class of embodiments, the system includes an array of non-human animals in containers, a monitoring module, and a correlation module. The monitoring module monitors expression or activity of wwp-1 or a homolog thereof, expression or activity of ubc-18 or a homolog thereof, and/or post-translational modification state of wwp-1 or a homolog thereof or a substrate thereof (e.g., cep-1, pha-4, skn-1b, or other substrate described herein or known in the art) in the non-human animals in the array following administration of a test compound. The correlation module then correlates an increase in expression or activity of wwp-1 or the homolog thereof, an increase in expression or activity of ubc-18 or the homolog thereof, increased phosphorylation of wwp-1 or the homolog thereof, and/or increased ubiquitination of the substrate to longevity, thereby identifying the compound(s) that modulate longevity.

Another general class of embodiments also provides methods of identifying a modulator of longevity. In these methods, a cell is provided and contacted with a test compound. Expression or activity of wwp-1 or a homolog thereof, expression or activity of ubc-18 or a homolog thereof, and/or post-translational modification state of wwp-1 or a homolog thereof or a substrate thereof (e.g., cep-1, pha-4, skn-1b, or other substrate described herein or known in the art) in the cell is monitored. An increase in expression or activity of wwp-1 or the homolog thereof, an increase in expression or activity of ubc-18 or the homolog thereof, increased phosphorylation of wwp-1 or the homolog thereof, and/or increased ubiquitination of the substrate indicates that the test compound modulates (e.g., increases) longevity.

As for the embodiments above, the cells optionally express a reporter construct that facilitates measurement of expression or activity. For example, the cell can express a fusion protein comprising GFP or a homolog thereof and either wwp-1 or a homolog thereof or ubc-18 or a homolog thereof. In such embodiments, monitoring expression of wwp-1 or ubc-18 or the homolog thereof involves monitoring an optical signal from the GFP. Exemplary test compounds include, e.g., a small molecule, a polypeptide, an antibody, a nucleic acid, an antisense molecule, or a double-stranded RNA.

Yet another general class of embodiments provides methods for modulating (e.g., increasing) longevity of an animal. In the methods, expression or activity of wwp-1 or a homolog thereof and/or of ubc-18 or a homolog thereof in the animal is modulated. For example, expression of wwp-1 or the homolog thereof, activity of wwp-1 or the homolog thereof, phosphorylation of wwp-1 or the homolog thereof, or expression or activity of ubc-18 or the homolog thereof can be increased.

Modulation can be effected, for example, by administration to the animal of a longevity modulator that affects wwp-1 or the homolog thereof or ubc-18 or the homolog thereof. Exemplary modulators include compounds that increase expression of wwp-1 or the homolog thereof, decrease expression or activity of a phosphatase that dephosphorylates wwp-1 or the homolog thereof, or increase expression or activity of a kinase that phosphorylates wwp-1 or the homolog thereof.

The animal can be a human, or it can be a non-human animal. The animal is optionally also subjected to dietary restriction.

Yet another general class of embodiments provides methods of delaying onset of an age-related disease such as diabetes, a cardiovascular disease, or a neurodegenerative disease in an animal. In these methods, expression or activity of wwp-1 or a homolog thereof and/or of ubc-18 or a homolog thereof in the animal is modulated (e.g., increased or decreased). As for the embodiments above, modulation can be effected, e.g., by administration of a longevity modulator that affects wwp-1 or the homolog thereof or ubc-18 or the homolog thereof. The animal can be a human, or it can be a non-human animal. The animal is optionally also subjected to dietary restriction.

BRIEF DESCRIPTION OF THE DRAWINGS

The file of this patent contains at least one drawing executed in color. Copies of this patent with color drawing(s) will be provided by the Patent and Trademark Office upon request and payment of the necessary fee.

FIG. 5 Panels A-B illustrate that wwp-1 RNA-mediated interference specifically interferes with its gene expression. Panel A presents data from RT-PCR analysis of N2 and wwp-1 (ok1102) worms indicating loss of wwp-1 mRNA in mutant worms (top panel). eft-4 and act-5 serve as controls (bottom panels). Panel B presents data from RT-PCR analysis of worms fed wwp-1 dsRNA or vector control. wwp-1 dsRNA is able to knock down expression of wwp-1 (top panel) but not y65b4br.5 and y65b4br.8 (middle panels). Act-5 serves as a control (bottom panel).

FIG. 6 Panels A-F illustrate that WWP-1 is expressed in neurons. Using an N-terminal GFP-tagged WWP-1 under control of the endogenous promoter, GFP fluorescence is detected in head (Panels A-B) and tail (Panels C-D) neurons as well as the ventral nerve chord (Panels E-F) Composite DIC/fluorescent pictures (Panels A, C, and E) are shown followed by fluorescent pictures (Panels B, D, and F).

FIG. 7 Panels A-D illustrate that GFP signal is reduced upon wwp-1 dsRNA treatment in GFP-tagged wwp-1 overexpressing worms. DIC pictures (Panels A, C) or fluorescent pictures (Panels B, D) of day 3 adult transgenic worms fed wwp-1 dsRNA (Panels C, D) or control vector (Panels A, B) since L1 stage are shown. Intestinal auto-fluorescence was observed with longer exposure in adults.

FIG. 16 Panels A-H illustrate the ubc-18 expression pattern and show that ubc-18 promoter::GFP reporter strains express GFP in specific head (Panels A-D) and tail (Panels E-H) sensory neurons. Overlay of the UBC-18::GFP expression in the hermaphrodite head and tail (green fluorescence, Panels A and E) and the DiI staining of the ciliated amphid neurons (red fluorescence, Panels B and F). The cells that are stained by DiI and expressing green fluorescence protein (GFP) merge to yellow (Panels C and G). DIC images are shown in Panels D and H.

DEFINITIONS

Figures 1G, 1H:
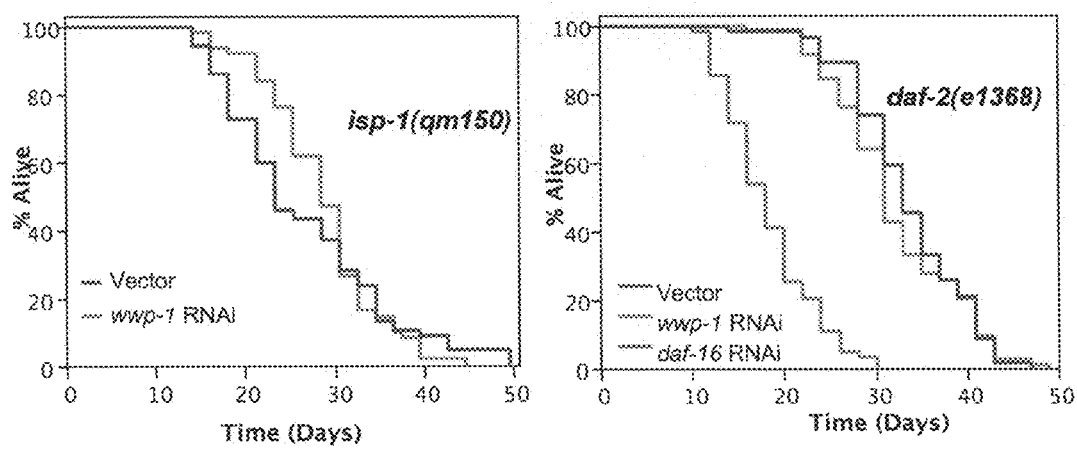
FIG. 1 Panels A-H illustrate that wwp-1 is required and specific for the extension of lifespan by dietary restriction (DR). The percentage of animals remaining alive is plotted against animal age. Lifespan values are given in Table 1. Panel A presents a line graph showing that wwp-1 is a positive regulator of lifespan. Two independent wwp-1 overexpressing strains (GFP::WWP-1) can extend longevity compared to control worms expressing GFP. Panel B presents a line graph showing that wwp-1 is essential for increased longevity in eat-2 mutant worms; lifespan analysis of eat-2(ad116) mutant animals fed control vector or wwp-1 dsRNA is presented. Panel C presents a line graph showing that wwp-1 is required for the increased longevity of true DR; lifespan analysis of N2 and wwp-1 (ok1102) mutant worms grown in DR or AL (ad libitum) $E.$ $coli$ concentrations is shown. Panel D presents a line graph showing that the longevity of wwp-1 mutant worms does not change in response to varying bacterial concentrations; lifespans of N2 and wwp-1 (ok1102) mutant worms grown in S basal buffer with different $E.$ $coli$ concentrations are illustrated. The slight decrease in longevity seen at the extreme ends of the curve of wwp-1 mutant animals is likely due to increased stress by starvation (at the lowest concentrations) or hypoxia (at higher concentrations). Lifespan curves were plotted from a representative experiment of three independent experiments using 40-60 worms per dilution per experiment. Panels E-F present line graphs showing that wwp-1 interacts genetically with the foxa transcription factor pha-4 but not daf-16. Graphs show lifespan analysis of wwp-1 overexpressing worms (GFP::WWP-1) or control line expressing GFP fed pha-4 dsRNA (Panel E), daf-16 dsRNA (Panel F) or control vector. Panels G-H present line graphs showing that loss of wwp-1 does not affect other longevity pathways. Panel G illustrates that feeding wwp-1 dsRNA cannot suppress the extended longevity of isp-1 (qm150) mitochondrial mutant worms. Panel H illustrates that wwp-1 is not required for increased longevity of DAF-2 signaling; lifespan analysis of daf-2(e1368) fed wwp-1 dsRNA or control vector is shown.

Unless defined otherwise, all technical and scientific terms used herein have the same meaning as commonly understood by one of ordinary skill in the art to which the invention pertains. The following definitions supplement those in the art and are directed to the current application and are not to be imputed to any related or unrelated case, e.g., to any commonly owned patent or application. Although any methods and materials similar or equivalent to those described herein can be used in the practice for testing of the present invention, the preferred materials and methods are described herein.

Accordingly, the terminology used herein is for the purpose of describing particular embodiments only, and is not intended to be limiting.

As used in this specification and the appended claims, the singular forms "a", "an" and "the" include plural referents unless the context clearly dictates otherwise. Thus, for example, reference to "a modulator" optionally includes a combination of modulators, reference to "a cell" includes mixtures or populations of cells, and the like.

"Longevity" and/or "lifespan" (or life span) is used herein to refer to the length of a subject's life, e.g., the number of years, months, weeks, days, minutes, etc., in the lifespan of an animal. The subjects of the invention are typically non-human animals, e.g., rodents, nematodes, or flies, when screening methods are employed but are also optionally humans when treatment or modulation of longevity is claimed. As used herein an "increase" or "modulation" of longevity also optionally includes a delay in the onset of age-related diseases and/or conditions and/or a delay and/or stabilization of the aging process.

"Dietary restriction" refers to restriction in caloric intake of an animal, e.g., a subject being tested for longevity modulation. Typically, an animal subjected to dietary restriction receives about 70% of its normal caloric intake, e.g., while receiving all necessary nutrients and vitamins. In some embodiments, an animal may receive only about 60% or about 50% of its normal caloric intake when subjected to dietary restriction. Dietary restriction, as used herein, can also refer to models that are commonly used to simulate dietary restriction, such as mutant animals that are used as a genetic surrogate of dietary restriction (for example, nematodes that mimic dietary restriction with a reduced rate of pharyngeal pumping that is representative of reduced eating). Optionally, in worms, dietary restriction takes the form of bacterial dietary restriction, which involves limiting the concentration of bacteria fed to worms in culture.

A "modulator" of a specified trait or phenotype is a compound that affects that trait or phenotype. For example, a modulator of aging or longevity can slow aging or increase longevity in an animal to which the modulator is administered. Generally, a modulator is a compound that modulates expression and/or activity of a given gene, protein, polypeptide, mRNA, or the like, e.g., to produce a phenotypic change such as increase in lifespan. The term "modulate" refers to a change in an expression level, activity or property of the gene, protein, etc. For example, modulation can cause an increase or a decrease in a protein activity (e.g., catalytic activity) or binding characteristic (e.g., binding of a transcription factor to a nucleic acid). Modulation can, e.g., cause an increase or decrease in expression of one or more genes, e.g., a change in transcription level, a change in stability of an mRNA that encodes a polypeptide, a change in translation efficiency, and/or a change in protein stability. Change in apparent protein activity can arise from changes in its expression; as additional examples, a modulator can change (activate or inhibit) activity of the polypeptide itself, for example, by binding to the polypeptide and stabilizing a catalytically active conformation thereof, by binding to and inhibiting the polypeptide, or by affecting post-translational modification of the polypeptide and thus changing its activity. In addition, a modulator of the invention can result in a change in lifespan or a delay in the onset of an age-related disease or condition. Exemplary modulators include, but are not limited to, wwp-1 and ubc-18 ligands, antibodies, agonists, antagonists, complexes thereof, interfering RNAs, etc. Modulators of the invention are identified, e.g., from a group of "test compounds" or "test agents" that include, but are not limited to, polypeptides, proteins, antibodies, nucleic acids, antisense molecules, DNAs, RNAs, double-stranded RNAs, small molecules, hormones, transcription factors, and the like.

Aging is the accumulation of diverse adverse changes that typically increase the risk of disease or death or reduce quality of life. These changes can be attributed, e.g., to development, genetic defects, the environment, disease, and the inborn aging process. The modulators or test agents of the present invention can inhibit aging, e.g., in adult subjects, thereby increasing lifespan or longevity. In addition, the modulators of the present invention can also protect against one or more age-related diseases in a subject. Delaying onset of these diseases or conditions, e.g., delaying the time at which a subject begins to exhibit symptoms of the diseases, can also increase lifespan.

A "polypeptide" is a polymer comprising two or more amino acid residues (e.g., a peptide or a protein). The polymer can additionally comprise non-amino acid elements such as labels, quenchers, blocking groups, or the like and can optionally comprise modifications such as glycosylation or the like. The amino acid residues of the polypeptide can be natural or non-natural and can be unsubstituted, unmodified, substituted or modified.

The term "fusion protein" indicates that the protein includes polypeptide components derived from more than one parental protein or polypeptide. Typically, a fusion protein is expressed from a fusion gene in which a nucleotide sequence encoding a polypeptide sequence from one protein is appended in frame with, and optionally separated by a linker from, a nucleotide sequence encoding a polypeptide sequence from a different protein. The fusion gene can then be expressed by a cell as a single protein.

A "post-translational modification" of a protein is a transformation (generally an enzymatic transformation) that occurs following translation of some or all of the protein's amino acid residues. Typically, post-translational modification involves attachment of a small chemical group (or groups) to a functional group of certain amino acid residues (e.g., the epsilon amino group of lysine, or the hydroxyl group of serine, threonine, or tyrosine) or to the protein's terminal amino or carboxyl group. Examples include, but are not limited to, phosphorylation, glycosylation, acetylation, lipidation (e.g., prenylation, farnesylation, myristoylation, attachment of a fatty acid or a GPI anchor), ubiquitination, sumoylation, hydroxylation, methylation and nucleotidylation (e.g., ADP-ribosylation).

"Ubiquitination" (also called ubiquitylation) of a protein involves the post-translational attachment of one or more ubiquitin chains to the protein. Ubiquitination can, for example, affect the protein's stability (e.g., target the protein for proteasomal degradation), protein-protein interactions (e.g., with ubiquitin-binding domain proteins), activity, and/or subcellular localization. Ubiquitination typically depends on a three-component enzyme system, E1, E2, and E3. The E1 ubiquitin-activating enzyme forms a thioester bond between its active cysteine and a ubiquitin moiety, the E2 ubiquitin conjugating enzyme transfers this activated ubiquitin moiety to the target protein or onto a growing polyubiquitin chain, and the E3 ubiquitin ligase facilitates this reaction. Different classes of E3 ligases facilitate the transfer through different mechanisms; E3 ligases containing a characteristic HECT (Homologous to E6-AP C Terminus) domain serve as a catalytic intermediate in the transfer of ubiquitin chains from the E2 to the substrate. E3 ligases can, e.g., modify the protein substrate by monoubiquitination (and can singly or multiply monoubiquitinate the substrate) or by sequential attachment of ubiquitin moieties to form polyubiquitin chains. In some instances, ubiquitination (e.g., monoubiquitination) can involve E2 and not require E3. See, e.g., Bernassola et al. (2008) "The HECT family of E3 ubiquitin ligases: Multiple players in cancer development" Cancer Cell 14:10-21.

The term "nucleic acid" or "polynucleotide" encompasses any physical string of monomer units that can be corresponded to a string of nucleotides, including a polymer of nucleotides (e.g., a typical DNA or RNA polymer), PNAs, modified oligonucleotides (e.g., oligonucleotides comprising nucleotides that are not typical to biological RNA or DNA, such as 2'-O-methylated oligonucleotides), and the like. A nucleic acid can be e.g., single-stranded or double-stranded. Unless otherwise indicated, a particular nucleic acid sequence of this invention encompasses complementary sequences, in addition to the sequence explicitly indicated. The terms "DNA" and "RNA" include, but are not limited to, all single stranded and double stranded nucleic acid sequences or polynucleotides, such as cDNA, mRNA, antisense molecules, interfering RNAs, oligonucleotides, and the like. In addition, the nucleic acids of the invention include naturally occurring and non-naturally occurring nucleotide analogs and backbone substitutes, e.g., PNA, that one of skill in the art would recognize as capable of substituting for naturally occurring nucleotides and backbones of nucleic acids.

The term "antibody" herein is used in the broadest sense and specifically covers monoclonal antibodies, polyclonal antibodies, multispecific antibodies (e.g. bispecific antibodies) formed from at least two intact antibodies, chimeric antibodies, humanized antibodies, and antibody fragments (whether produced, e.g., by the modification of whole antibodies or synthesized de novo using recombinant DNA methodologies) so long as they exhibit a desired biological activity. An antibody is a protein comprising one or more polypeptides substantially or partially encoded by immunoglobulin genes or fragments of immunoglobulin genes. The recognized immunoglobulin genes include the kappa, lambda, alpha, gamma, delta, epsilon and mu constant region genes, as well as myriad immunoglobulin variable region genes. An intact antibody is one comprising heavy- and light-variable domains as well as an Fc region. Antibody fragments comprise a portion of an intact antibody, preferably comprising the antigen-binding region thereof. Examples of antibody fragments include Fab, Fab', F(ab')$_2$, and Fv fragments, diabodies, linear antibodies, single-chain antibody molecules, and multispecific antibodies formed from antibody fragments. Antibody fragments are optionally produced using enzymatic digestion of intact antibodies or synthesized chemically or by recombinant DNA methods. The subunit structures and three-dimensional configurations of different classes and fragments of immunoglobulins are well known and the term antibody as used herein includes all configurations, fragments, and classes. Methods of making and using antibodies are well known to those of skill in the art.

A "wwp-1 polypeptide" is a polypeptide that is the same as, a splice variant of, an isoform of, or homologous to a naturally occurring wwp-1 polypeptide (e.g., a *C. elegans* wwp-1), or that is derived from such a polypeptide (e.g., through cloning, recombination, mutation, or the like). The polypeptide can be full length or a fragment of a full length protein. A wwp-1 fragment typically includes at least 10 contiguous amino acids corresponding to a native wwp-1 protein, such as nematode wwp-1, and optionally includes catalytically active as well as catalytically inactive fragments. The fragment optionally includes at least about 25, at least about 50, at least about 75, at least about 100, at least about 250, at least about 500, or about 1000 or more contiguous amino acids corresponding to the native protein.

A "ubc-18 polypeptide" is a polypeptide that is the same as, a splice variant of, an isoform of, or homologous to a naturally occurring ubc-18 polypeptide (e.g., a *C. elegans* ubc-18), or that is derived from such a polypeptide (e.g., through cloning, recombination, mutation, or the like). The polypeptide can be full length or a fragment of a full length protein. A ubc-18 fragment typically includes at least 10 contiguous amino acids corresponding to a native ubc-18 protein, such as nematode ubc-18, and optionally includes active as well as inactive fragments. The fragment optionally includes at least about 25, at least about 50, at least about 75, at least about 100, at least about 250, at least about 500, or about 1000 or more contiguous amino acids corresponding to the native protein.

All polypeptides of the invention, e.g., wwp-1, ubc-18, pha-4, sod proteins, foxa proteins, and the like can be naturally occurring or recombinant, and are optionally unpurified, purified, or isolated, and exist, e.g., in vitro, in vivo, or in situ.

A "wwp-1 gene" or polynucleotide is a nucleic acid that encodes a wwp-1 polypeptide. Typically, the gene includes regulatory sequences that direct expression of the gene in one or more cells of interest. Optionally, the gene is a native gene that includes regulatory and coding sequences that naturally direct expression of a wwp-1 polypeptide, e.g., in a nematode such as *C. elegans* or other animal. It is understood that polynucleotides encoding all or varying portions of wwp-1 are included herein. Optionally, wwp-1 polynucleotides encode a polypeptide with wwp-1 activity, e.g., ubiquitin ligase activity. Such polynucleotides include naturally occurring, synthetic, and intentionally manipulated polynucleotides as well as splice variants. For example, portions of the mRNA sequence may be altered due to alternate RNA splicing patterns or the use of alternate promoters for RNA transcription.

A "ubc-18 gene" or polynucleotide is a nucleic acid that encodes a ubc-18 polypeptide. Typically, the gene includes regulatory sequences that direct expression of the gene in one or more cells of interest. Optionally, the gene is a native gene that includes regulatory and coding sequences that naturally direct expression of a ubc-18 polypeptide, e.g., in a nematode such as *C. elegans* or other animal. It is understood that polynucleotides encoding all or varying portions of ubc-18 are included herein. Optionally, ubc-18 polynucleotides encode a polypeptide with ubc-18 activity, e.g., ubiquitin conjugating activity. Such polynucleotides include naturally occurring, synthetic, and intentionally manipulated polynucleotides as well as splice variants. For example, portions of the mRNA sequence may be altered due to alternate RNA splicing patterns or the use of alternate promoters for RNA transcription.

Moreover, polynucleotides of the invention, e.g., wwp-1 polynucleotides, ubc-18 polynucleotides, or the like include polynucleotides having alterations in the nucleic acid sequence that still encode a polypeptide having the ability to modulate a wwp-1 ubiquitination pathway parameter such as longevity, lifespan and response to dietary restriction.

As used herein, the terms "wwp-1", "ubc-18", "pha-4", and the like refer to either the gene, the transcribed RNA, or its translated polypeptide, unless specifically stated otherwise. The term "wwp-1" is also used herein to refer to a gene and its protein and any homologs or orthologs thereof; therefore, while the invention is described primarily with reference to *C. elegans* wwp-1, any of its homologs (e.g., *Drosophila* or mammalian homologs, e.g., mammalian WWP1, WWP2, and ITCH) is also contemplated. Thus, "wwp-1" also include genes homologous to, and genes whose protein products are homologous or substantially identical to the protein product of, the *C. elegans* wwp-1 gene (e.g., as presented in Genbank accession no. NM_171831; see also SEQ ID NOs: 9 and 10 for amino acid and nucleotide sequences, respectively); examples of such orthologs include human wwp1 (Genbank accession no. NM_007013), human wwp2 (Genbank accession no. NM_025830), and human itch (Genbank accession no. NM_031483). Similarly, the term "ubc-18" is also used herein to refer to a gene and its protein and any homologs or orthologs thereof; therefore, while the invention is described primarily with reference to *C. elegans* ubc-18, any of its homologs (e.g., *Drosophila* or mammalian homologs, e.g., mammalian UBCH7) is also contemplated. Thus, "ubc-18" also include genes homologous to, and genes whose protein products are homologous or substantially identical to the protein product of, the *C. elegans* ubc-18 gene (e.g., as presented in Genbank accession no. NM_066140; see also SEQ ID NOs: 11 and 12 for amino acid and nucleotide sequences, respectively); examples of such orthologs include human ubch7 (Genbank accession no. AJ000519). The same convention is used for all other genes and proteins discussed herein. For example, "pha-4" also include genes homologous to, and genes whose protein products are homologous or substantially identical to the protein product of, the *C. elegans* pha-4 gene (e.g., as presented in Genbank accession no. NM_001047651; see also SEQ ID NOs: 13 and 14 for amino acid and nucleotide sequences, respectively).

The term "gene" is used broadly to refer to any nucleic acid associated with a biological function. Genes typically include coding sequences and/or the regulatory sequences required for expression of coding sequences. The term "gene" applies to a specific genomic sequence, as well as to a cDNA or an mRNA encoded by that genomic sequence. Genes also include non-expressed nucleic acid segments that, for example, form recognition sequences for other proteins. Non-expressed regulatory sequences include "promoters" and "enhancers", to which regulatory proteins such as transcription factors bind, resulting in transcription of adjacent or nearby sequences. In some cases, a gene is heritable. In some aspects, genes comprise coding sequences (e.g., an "open reading frame" or "coding region") necessary for the production of a polypeptide, while in other aspects, genes do not encode a polypeptide. Examples of genes that do not encode polypeptides include ribosomal RNA genes (rRNA) and transfer RNA (tRNA) genes. Genes of use in the present invention include, but are not limited to, wwp-1, wwp1, wwp2, itch, ubc-18, ubch7, pha-4, daf-16, foxa, sod, and other genes involved in longevity and dietary restriction pathways.

"Expression" of a gene or expression of a nucleic acid means transcription of DNA into RNA (optionally including modification of the RNA, e.g., splicing), translation of RNA into a polypeptide (possibly including subsequent modification, e.g., posttranslational modification), or both transcription and translation. "Reduced expression", e.g., of wwp-1 or ubc-18, refers to a situation in which a particular gene in a cell or animal is not translated at the same level as it would be in a wild-type or unmodified organism, whether because transcription, translation, or both are reduced. Reduced expression includes a condition in which expression of the gene does not occur at all, e.g., a knock-out gene, as well as conditions in which expression levels are merely reduced as compared to the gene in a wild-type organism or cell. "Overexpression", e.g., of wwp-1 or ubc-18, refers to a situation in which a particular gene in a cell or animal is translated at a higher level than it would be in a wild-type or unmodified organism, whether because transcription, translation, or both are increased. The "expression level" of a gene is the level at which the gene is expressed in a cell or organism and can include the level at which the gene is transcribed and/or the level at which it is translated into a protein. Activity level is also used to refer to the activity of the protein, e.g., an enzyme, and its level of activity in a cell, e.g., enzymatic or binding activity of a protein encoded by the gene at issue. A cell or animal expressing wwp-1 and/or ubc-18 includes any sample comprising a functional wwp-1 and/or ubc-18 gene, its transcribed RNA(s), and/or translated polypeptide(s).

Expression or activity is "artificially altered" when it is altered by human intervention. For example, a gene can be overexpressed or can be expressed at lower levels than in a wild-type organism or cell as a result of human intervention, or a naturally occurring gene can be replaced, e.g., with a construct encoding a dominant negative protein or with a reporter gene encoding a fusion protein that is expressed at approximately wild-type levels. As another example, such a construct or reporter can be expressed in addition to the naturally occurring gene. Expression of a gene can be artificially altered, for example, using recombinant DNA techniques to alter, e.g., its coding region(s) and/or regulatory element(s), by insertion of a transposable element, or by exposing it to a chemical, ionizing radiation, or the like and then performing in vitro or in vivo selection for a desired mutated form of the gene. Expression can be affected, e.g., by artificially introduced point mutations, insertions of one or more nucleotides (or amino acids, when referring to an encoded polypeptide), transposon insertions, and deletions of one or more nucleotides (or amino acids), or by use of RNA interference or similar techniques (e.g., introduction or expression of a small interfering RNA, short hairpin RNA, an antisense nucleic acid, etc.) to eliminate or reduce expression of the gene. Activity (e.g., specific activity) of a protein can be similarly artificially altered, e.g., by affecting its expression level, by mutations (e.g., point mutations, deletions, insertions, fusions, etc.) that directly affect activity without affecting expression level, or by controlling post-translational modifications that affect activity (e.g., increasing or decreasing phosphorylation level or the like).

The term "recombinant" indicates that the material (e.g., a nucleic acid or a protein) has been artificially or synthetically (non-naturally) altered by human intervention. The alteration can be performed on the material within, or removed from, its natural environment or state. For example, a "recombinant nucleic acid" is one that is made by recombining nucleic acids, e.g., during cloning, DNA shuffling or other procedures; a "recombinant polypeptide" or "recombinant protein" is a polypeptide or protein which is produced by expression of a recombinant nucleic acid.

A "wwp-1 ubiquitination pathway parameter" refers to a measurable parameter that is mediated by wwp-1 and/or ubc-18 such as longevity, lifespan, level of autophagy, and/or response to dietary restriction. In addition, a wwp-1 ubiquitination pathway parameter is optionally an activity or expression level of wwp-1 (e.g., activity of a wwp-1 polypeptide, transcription of a wwp-1 gene into mRNA, or translation level), an activity or expression level of ubc-18 (e.g., activity of a ubc-18 polypeptide, transcription of a ubc-18 gene into mRNA, or translation level), or activity or expression of any gene or polypeptide that can be correlated to wwp-1 and/or ubc-18. For example, pha-4 functions downstream of wwp-1 and thus its expression or activity can be used as a wwp-1 ubiquitination pathway parameter. Similarly, post-translational modification state of various proteins can be used as wwp-1 ubiquitination pathway parameters, for example, phosphorylation state of wwp-1 (which is correlated with its activity) and ubiquitination state of wwp-1 substrates (which is correlated with wwp-1 and ubc-18 activity).

The term "age related disease" is used herein to refer to diseases, conditions and symptoms that are predominantly found or manifested in older animals, e.g., in humans, people over 50 or more preferably people over 65. For any animal, age-related diseases would manifest after maturation, e.g., post-development. The age at which maturity is reached is different depending on the animal and for each animal such time would be well known to those of skill in the art. Age-related diseases include certain cancers, cardiovascular disease, atherosclerosis, hypertension, diabetes (e.g., type 2), osteoporosis, depression, neurodegenerative disease, Alzheimer's, Parkinson's, glaucoma, certain immune system defects, kidney failure, liver steatosis, and other conditions well known to those of skill in the art.

The term "animal" refers to an invertebrate or vertebrate animal. In some aspects (e.g., when describing treatment and diagnostic procedures), animals include humans, while other aspects (e.g., most screening procedures) relate only to non-human animals. Exemplary non-human animals include, but are not limited to, insects (e.g., Drosophila, including Drosophila melanogaster), nematodes (e.g., Caenorhabditis elegans), mammals, non-human primates, rodents (e.g., mice, rats, and hamsters), stock and domesticated animals (e.g., pigs, cows, sheep, horses, cats, and dogs), and birds. In certain embodiments, animals amenable to transformation techniques are particularly useful. As used herein, the term animal refers to either a whole animal, an animal organ, an animal cell, or a group of animal cells, such as an animal tissue, for example, depending upon the context.

An "autophagy pathway parameter" refers to a measurable parameter mediated by a member of the pathway that regulates autophagy (particularly autophagy that is induced or stimulated by dietary restriction and that is involved in lifespan extension), e.g., wwp-1, ubc-18, rab-10, TOR, atg-1, vps-34, bec-1, and/or pha-4. Level of autophagy is an autophagy pathway parameter of particular interest herein. In addition, an autophagy pathway parameter is optionally an activity or expression level or a post-translational modification state of wwp-1, ubc-18, rab-10, TOR, atg-1, vps-34, bec-1, pha-4, or another member of the autophagy pathway comprising these factors.

A variety of additional terms are defined or otherwise characterized herein.

DETAILED DESCRIPTION

Dietary restriction is known to increase lifespan in a variety of animals, including mice, flies, worms, and others. Among other aspects, genes that mediate this process are described herein, and screening methods for identifying modulators of such genes are presented. By identifying modulators of the genes (or their products) that mediate this process, methods of modulating longevity and compounds with which to do so are also provided.

Embodiments of the invention are based, in part, upon the identification of the HECT E3 ubiquitin ligase WWP-1 and the E2 ubiquitin conjugating enzyme UBC-18 as mediators of dietary restriction induced longevity in C. elegans. Characterizing the role of wwp-1 and ubc-18 in dietary restriction and their relationship to other genes in the dietary restriction pathway provides aspects of the present invention, including, without limitation, novel methods of identifying modulators of longevity, e.g., by identifying test compounds that modulate the wwp-1/ubc-18 ubiquitination pathway to increase longevity.

In brief, data presented herein show that wwp-1 and ubc-18 mediate dietary restriction induced longevity. Loss of wwp-1 or ubc-18 blocks the response to dietary restriction, and overexpression of wwp-1 extends lifespan. In addition to being required for dietary restriction induced longevity, wwp-1 and ubc-18 are also shown to be specific to dietary restriction induced longevity, in that neither wwp-1 nor ubc-18 is required for the insulin/IGF-1 or mitochondrial electron transport longevity pathways. Further, loss of wwp-1 or ubc-18 is shown to block dietary restriction induced autophagy, which is involved in lifespan extension. These and additional findings are described in greater detail in the Examples section below.

The studies described herein focused on the roles of wwp-1 and ubc-18 in lifespan control in C. elegans, and the results provide the first evidence that ubiquitination plays a positive role in lifespan determination. Targeting components of the ubiquitin pathway can thus lead to the development of new therapeutic agents. Because of the wide-ranging roles of the pathway in many cellular pathways, it may be difficult to limit the negative effects of agents that target the general ubiquitination machinery. However, an increase in the specificity of therapeutic intervention by targeting individual ubiquitin ligases (such as wwp-1) can boost the effectiveness of treatment and eliminate nonspecific side effects.

Therefore, wwp-1 and ubc-18 are useful targets for screening for modulators of longevity, as are other members of the pathway, such as pha-4 (demonstrated to be downstream of wwp-1 and ubc-18) and substrates of wwp-1 whose ubiquitination regulates dietary restriction induced longevity. In one aspect, the invention provides screening methods and systems to identify compounds that alter wwp-1 ubiquitination pathway parameters, such as lifespan, activity or expression level of wwp-1, activity or expression level of ubc-18, activity or expression level of pha-4, post-translational modification state of a substrate of wwp-1, post-translational modification state of wwp-1 itself (catalytic activity of the mammalian homolog ITCH is enhanced by phosphorylation, see Gallagher et al. (2006) "Activation of the E3 ubiquitin ligase Itch through a phosphorylation-induce conformational change" Proc Nat Acad Sci 103:1717-1722), autophagy, or other parameters correlated with lifespan. Such compounds are then optionally used to increase longevity, e.g., to treat a patient suffering from premature aging or to extend normal lifespan.

Before describing the present invention in detail, it is to be understood that the invention herein is not necessarily limited to use with C. elegans wwp-1, ubc-18, or other dietary restriction induced longevity, autophagy, and ubiquitin pathway factors, but also includes homologs or orthologs thereof. As just a few examples, use of the mammalian ligases WWP1, WWP2, and ITCH with which C. elegans wwp-1 is highly conserved is contemplated, as is use of mammalian UBCH7 which shows similarity to C. elegans ubc-18.

Dietary restriction reduces the incidence of age-related diseases such as cancer, cardiovascular disease and diabetes in mammals and has been found to improve functional outcome in models of Alzheimer's, Parkinson's, and Huntington's disease. A detailed understanding of the pathways that mediate the benefits of DR can thus also lead to novel therapies for age related diseases, as described herein.

Screening for Longevity Modulators

In one aspect, methods of identifying compounds that modulate longevity and/or delay onset of age-related diseases or conditions, e.g., by modulating an activity or expression level of a wwp-1 or ubc-18 gene or polypeptide or other gene or protein involved in the dietary restriction pathway, are provided. Generally, in the methods, a cell or non-human animal is contacted with or administered a test compound (also called a test agent herein), and a parameter related to the wwp-1/ubc-18 ubiquitin pathway is assayed. Suitable parameters include, but are not limited to, expression or activity of wwp-1 or a homolog thereof, expression or activity of ubc-18 or a homolog thereof, expression or activity of a downstream factor (for example, pha-4, sod-1, sod-2, sod-4, sod-5, or a homolog of any thereof, such as a mammalian foxa), post-translational modification state of wwp-1 or a homolog thereof, post-translational modification state of a wwp-1 or ubc-18 substrate, lifespan, level of authophagy, time of onset of an age related disease or condition, or binding of the test compound to one of the above genes or polypeptides or complexes thereof. By assaying changes in these parameters, compounds or combinations of compounds that modify, e.g., increase, longevity are identified. Compounds identified by these methods are also a feature of the invention, as are systems for conveniently screening test compounds to identify modulators of longevity.

Test compounds or agents for use in the methods provided include, but are not limited to, polypeptides, proteins, antibodies, nucleic acids, antisense molecules, small molecules (e.g., a compound with a molecular weight less than 1000 daltons), hormones, transcription factors, interfering RNAs (e.g., double-stranded RNAs, siRNAs, etc.), ions, carbohydrates, organic or inorganic compounds, protein fragments, nucleic acid fragments, antibody fragments, and the like, and are optionally selected from natural or synthetic molecules. A test compound is optionally an antagonist of a dietary restriction pathway polypeptide or gene, an agonist of such a polypeptide or gene, a ligand that specifically binds to a polypeptide or gene of the invention, an antibody that specifically binds to a polypeptide or gene in the pathway, or the like. For example, a test compound or modulator of the invention is optionally a ligand or other compound that alters (e.g., increases) expression of wwp-1 and/or ubc-18 or alters (e.g., increases) activity of wwp-1 and/or ubc-18. Exemplary compounds that increase activity of wwp-1 include, but are not limited to, compounds that bind wwp-1 and stabilize its catalytically active conformation, compounds that prevent or decrease binding of an inhibitor to wwp-1, compounds that activate a kinase that phosphorylates and thus activates wwp-1 (e.g., jnk), and compounds that inhibit a phosphatase that dephosphorylates and thus inactivates wwp-1.

Libraries of test compounds to be screened for potential modulators are available. These libraries are optionally random or targeted. Targeted libraries include those designed using any form of a rational design technique that selects scaffolds or building blocks to generate combinatorial libraries. These techniques include a number of methods for the design and combinatorial synthesis of target-focused libraries, including morphing with bioisosteric transformations, analysis of target-specific privileged structures, and the like. In general, where information regarding structure of wwp-1/ubc-18 ubiquitin pathway genes or gene products is available (e.g., wwp-1, ubc-18, a kinase or phosphatase that acts on wwp-1, etc.), likely binding partners can be designed, e.g., using flexible docking approaches, or the like. Similarly, random libraries exist for a variety of basic chemical scaffolds. In either case, many thousands of scaffolds and building blocks for chemical libraries are available, including those with polypeptide, nucleic acid, carbohydrate, and other backbones. Commercially available libraries and library design services include those offered by Chemical Diversity (San Diego, Calif.), Affymetrix (Santa Clara, Calif.), Sigma (St. Louis Mo.), ChemBridge Research Laboratories (San Diego, Calif.), TimTec (Newark, Del.), Nuevolution A/S (Copenhagen, Denmark) and many others; see also the section entitled "Test Compound Libraries" hereinbelow.

In a screen for modulators, optionally a panel of different test compounds or potential modulators (i.e., two or more) are administered to different animals (e.g., isogenic or near isogenic animals) or contacted with different cell populations, the effect of each compound on the phenotype is monitored, and one or more modulators having the desired effect are identified.

In general, test compounds that enhance activity or expression of wwp-1 and/or ubc-18 are desirable, e.g., to modulate lifespan. Identification of compounds that increase longevity or delay onset of age-related diseases is optionally achieved by utilizing the genes and/or polypeptides of the invention, including active fragments thereof, in cell-free assays, cell-based assays, and/or whole organism assays, e.g., in nematodes or other model organisms. A variety of formats are applicable, including measurement of lifespan, expression, or activity, e.g., using any of the parameters described above, as will be described in greater detail below.

Cell-Free Assays

In one aspect, cell-free assays are employed to identify compounds that modulate longevity or onset of age-related diseases. In one embodiment, cell-free assays for identifying such compounds comprise a mixture containing a wwp-1 and/or ubc-18 polypeptide or gene (or homologs or orthologs thereof) and a test compound or a library of test compounds. In the cell-free assay, binding of the test compounds to the wwp-1 and/or ubc-18 polypeptides or genes is measured, e.g., to prescreen a library of compounds. Any compounds that specifically bind to wwp-1 and/or ubc-18 are then optionally tested in further cell-free assays, a cell based assay, or a whole organism assay, e.g., for an effect on lifespan, gene expression, or protein activity. Detection of the formation of complexes is achieved by conventional methods well known to those of skill in the art.

For example, in one embodiment, a library of test compounds is synthesized on a solid substrate, e.g., a solid surface, plastic pins or some other surface. The test compounds are reacted with a polypeptide and/or gene and washed to elute unbound polypeptide. Bound polypeptide and/or gene is/are then detected by methods well known in the art. A reciprocal assay can also be used, e.g., in which the polypeptides and/or genes of interest, e.g., wwp-1 and/or ubc-18, are applied directly onto plates and binding of a test compound to the polypeptides or genes is detected. An antibody or other ligand binding to a polypeptide and/or gene of interest is optionally detected in either format. For example, a ligand that binds to a wwp-1 and/or ubc-18 gene or polypeptide can be identified in this manner.

Interaction between molecules is also optionally assessed using real-time BIA (Biomolecular Interaction Analysis, e.g., using devices from Pharmacia Biosensor AB), which detect surface plasmon resonance (an optical phenomenon). Detection depends on changes in the mass concentration of macromolecules at the biospecific interface and does not require specific labeling of the molecules. In one useful embodiment, a library of test compounds is immobilized on a sensor surface, e.g., a wall of a micro-flow cell. A solution containing a wwp-1 and/or ubc-18 polypeptide or gene is then continuously circulated over the sensor surface. An alteration in the resonance angle, as indicated on a signal recording, indicates the occurrence of an interaction. This general technique is described in more detail in the *BIAtechnology Handbook* by Pharmacia.

Optionally, a wwp-1 and/or ubc-18 polypeptide or gene is immobilized to facilitate separation of complexes formed between the polypeptide or gene of interest and a test compound from uncomplexed forms of the polypeptide or gene. This also facilitates automation of the assay. Complexation of wwp-1 and/or ubc-18 can be achieved in any type of vessel, e.g., microtiter plates, microfluidic chambers or channels, micro-centrifuge tubes and test tubes. In one embodiment, a wwp-1 and/or ubc-18 polypeptide is fused to another protein, e.g., glutathione-S-transferase, to form a fusion protein which is adsorbed onto a matrix, e.g., glutathione SEPHAROSE™ beads (Sigma Chemical. St. Louis, Mo.), which is then combined with a radiolabeled test compound or test compound library and incubated under conditions sufficient to form test compound-polypeptide complexes. Subsequently, the beads are washed to remove unbound label, and the matrix is immobilized and the radiolabel is determined. Similar methods for immobilizing proteins on matrices use biotin and streptavidin. For example, a protein can be biotinylated using biotin NHS (N-hydroxy-succinimide) using well known techniques and immobilized in the well of streptavidin-coated plates. The immobilized wwp-1 and/or ubc-18 is then used to test for binding of test compounds.

Cell-free assays for wwp-1 and/or ubc-18 activity are described in the Examples section below. In one embodiment, a test compound (optionally but not necessarily pre-screened for binding to wwp-1 and/or ubc-18 as described above) is added to such a cell-free assay, and its effect on wwp-1 and/or ubc-18 activity is monitored. Activators (test compounds that increase ubiquitination of one or more substrates by wwp-1 and ubc-18 in the cell-free assay) or inhibitors (test compounds that decrease ubiquitination of one or more substrates by wwp-1 and ubc-18 in the cell-free assay) can thus be identified.

It will be evident that similar considerations apply to other cell-free assays. For example, test compounds can be screened for binding to a kinase or phosphatase that acts on wwp-1. As another example, test compounds can be screened in cell-free assays including the test compound, the kinase or phosphatase, and wwp-1, and optionally including ubc-18 and/or a wwp-1 substrate. Whether the test compound activates or inhibits the kinase or phosphatase can be monitored, e.g., by assessing phosphorylation state of wwp-1 or by assaying wwp-1 activity by assaying ubiquitination state of the substrate.

Test compounds that are identified in cell free assays are then optionally screened further for modulation of lifespan or other wwp-1 ubiquitination pathway parameters, e.g., in cell based or whole organism methods as described below.

Cell Based Assays

In one aspect of the invention, cell-based assays are used for identifying compounds that modulate longevity or onset of age-related disease, e.g., compounds that bind to, activate and/or modulate wwp-1, ubc-18, and/or other factors that mediate dietary restriction-induced longevity. In certain exemplary embodiments, expression of wwp-1 or ubc-18 has been altered in the cells employed, while in other exemplary embodiments, the cells exhibit wild-type expression of wwp-1 and ubc-18.

Accordingly, one general class of embodiments provides methods of screening for a compound that modulates longevity in which a cell (e.g., a population of cells) that exhibits artificially altered expression or activity of wwp-1 or a homolog thereof and/or of ubc-18 or a homolog thereof is contacted with a test agent. A wwp-1 ubiquitination pathway parameter in the cell is then assayed, and a change in the wwp-1 ubiquitination pathway parameter relative to a control sample (e.g., a control cell) without the test agent identifies the compound that modulates longevity.

As noted above, expression and activity can be altered using any of a wide variety of techniques known in the art, e.g., through recombinant DNA techniques, mutagenesis, or the like.

In one class of embodiments, the cell exhibits reduced expression or activity of wwp-1 or the homolog thereof and/or reduced expression or activity of ubc-18 or the homolog thereof. For example, expression or activity can be reduced by at least 50%, at least 75%, or at least 90%, or can be undetectable. As just a few examples, expression and/or activity can be reduced using RNA interference or antisense techniques to decrease expression or through mutations (e.g., point mutations, insertions, or deletions) that decrease expression at an mRNA or protein level or that render the protein less active or inactive. In one embodiment, the cell expresses a dominant negative form of wwp-1 or the homolog thereof (e.g., wwp-1 having a point mutation at the catalytic cysteine; see the Examples section below) or a dominant negative form of ubc-18 or the homolog thereof (e.g., ubc-18 having a point mutation at the catalytic cysteine). Such cells exhibiting reduced expression or activity of wwp-1 or ubc-18 can be useful, for example, in screens for compounds that increase expression or activity of wwp-1, ubc-18, or a component downstream thereof.

In another class of embodiments, the cell overexpresses wwp-1 or the homolog thereof and/or ubc-18 or the homolog thereof. For example, a transcript and/or translated product can be present in the cell at an amount that is at least 2×, at least 5×, at least 10×, at least 50×, or even at least 100× normal for that cell type (including expression in a cell not normally expressing the gene). In a related class of embodiments, the cell expresses a constitutively active form of wwp-1 or ubc-18; for example, wwp-1 with a mutation disrupting an inhibitory interaction between its WW and HECT domains.

In some embodiments, the artificial alteration in expression provides a convenient way to assay the wwp-1 ubiquitination pathway parameter. For example, the cell can express a recombinant reporter construct whose expression is easily monitored. In one such embodiment, the cell expresses a fusion protein comprising GFP (green fluorescent protein) or a homolog thereof (e.g., YFP, CFP, RFP, etc.) and either wwp-1 or a homolog thereof or ubc-18 or a homolog thereof, typically under control of an endogenous wwp-1 or ubc-18 (or homologous) promoter; see, e.g., the Examples section below. Changes in expression of wwp-1 or ubc-18 can thus be easily monitored by monitoring expression of the GFP moiety in the fusion protein. It will be evident that essentially any similar reporter can be substituted for GFP, e.g., another fluorescent moiety, a reporter enzyme, an epitope tag, etc. The reporter construct can replace the corresponding native gene in the cell or can be in addition to the native gene.

Suitable wwp-1 ubiquitination pathway parameters that can be assayed include, but are not limited to, one or more of an activity or expression level of wwp-1 or the homolog thereof, an activity or expression level of ubc-18 or the homolog thereof, an activity or expression level of pha-4 or a homolog thereof (e.g., mammalian foxa1, foxa2, or foxa3) or another downstream factor (e.g., a sod such as sod-1, sod-2, sod-4, or sod-5), post-translational modification state of wwp-1 or the homolog thereof, post-translational modification state of a substrate of wwp-1 (or ubc-18) or the homolog thereof, and level of autophagy. Other parameters that can optionally be assayed include, e.g., expression or activity level or post-translational modification state of autophagy pathway members such as rab-10, TOR, atg-1, vps-34, or bec-1 or a homolog thereof. Compounds that increase longevity or delay onset of age-related diseases can be identified, for example, as those that increase expression of wwp-1 or the homolog thereof, ubc-18 or the homolog thereof, or pha-4 or the homolog thereof; increase activity of wwp-1 or the homolog thereof, ubc-18 or the homolog thereof, or pha-4 or the homolog thereof; increase phosphorylation of wwp-1 or the homolog thereof; or increase ubiquitination of the substrate of wwp-1 (or ubc-18) or the homolog thereof, e.g., by at least 2x, at least 5x, at least 10x, at least 50x, or even at least 100x normal for that cell type. Similarly, compounds of interest can increase autophagy (e.g., by at least 2x, at least 5x, at least 10x, at least 50x, or even at least 100x), decrease expression or activity of rab-10 or TOR or the homolog thereof, or increase expression or activity of atg-1, vps-34, or bec-1 or the homolog thereof.

Another general class of embodiments also provides methods of identifying a modulator of longevity. In these methods, a cell is provided (typically, a cell or population of cells expressing or capable of expressing wwp-1, ubc-18, and/or other genes in the dietary restriction pathway) and contacted with a test compound. Expression or activity of wwp-1 or a homolog thereof, expression or activity of ubc-18 or a homolog thereof, and/or post-translational modification state of wwp-1 or a homolog thereof or a substrate thereof in the cell is monitored. A change (e.g., an increase) in expression or activity of wwp-1 or the homolog thereof, a change (e.g., an increase) in expression or activity of ubc-18 or the homolog thereof, altered (e.g., increased) phosphorylation of wwp-1 or the homolog thereof, and/or altered (e.g., increased) ubiquitination of the substrate, e.g., relative to an untreated cell, indicates that the test compound modulates (e.g., increases) longevity. Similarly, other parameters related to the wwp-1/ubc-18 ubiquitin pathway or the autophagy pathway, as described herein, can be monitored.

As for the embodiments above, the cells optionally express a reporter construct that facilitates measurement of expression or activity. For example, the cell can express a fusion protein comprising GFP or a homolog thereof and either wwp-1 or a homolog thereof or ubc-18 or a homolog thereof. In such embodiments, monitoring expression of wwp-1 or ubc-18 or the homolog thereof involves monitoring an optical signal from the GFP (e.g., using a fluorescence microscope, a fluorimeter, a plate reader, etc., whether manually or in an automated system).

Yet another general class of embodiments provides methods of screening for a compound that modulates longevity and/or autophagy (e.g., dietary restriction-induced autophagy). In the methods, a cell (e.g., a population of cells), preferably that exhibits artificially altered expression or activity of wwp-1 or a homolog thereof and/or of ubc-18 or a homolog thereof, is contacted with a test agent. An autophagy pathway parameter in the cell is then assayed, and a change in the autophagy pathway parameter relative to a control sample (e.g., a control cell) without the test agent identifies the compound that modulates longevity and/or autophagy. Compounds of particular interest include those that increase autophagy or lifespan, decrease expression or activity of rab-10 or TOR (including homologs thereof), or increase expression or activity of atg-1, vps-34, bec-1, or pha-4 (or a homolog thereof). Essentially all of the features for the embodiments above apply to these methods as well, as relevant.

Cells that are useful for any of the screening methods of the invention include, for example, human or other mammalian cells, yeast cells, bacterial cells, insect cells, avian cells, amphibian cells, *Xenopus* oocytes, nematode cells, and essentially any other cells that express wwp-1, ubc-18, homologs thereto, and/or other genes of interest, whether that expression is natural to the cell or the result of recombinant introduction of a wwp-1, ubc-18, or other gene of interest into the cell. Thus, the cells are optionally those associated with expression of wwp-1, ubc-18, and/or other genes of interest in vivo, such as neuronal cells or heart, brain, liver, or kidney cells, or are derived from such cells through culture, or are recombinant cells (typically selected for ease of culture and manipulation) expressing heterologous wwp-1, ubc-18, and/or other genes of interest. The cells optionally exhibit artificially altered expression of one, two, or more of wwp-1, ubc-18, and other genes that mediate dietary restriction induced longevity, and/or optionally exhibit artificially altered expression of or comprise mutations (e.g., loss of function mutations) in one or more genes in the insulin/IGF-1 and/or mitochondrial electron transport longevity pathways and/or autophagy pathway. Cells are optionally isolated (e.g., not part of an animal or tissue) and/or cultured cells.

Expression of wwp-1, ubc-18, or any other ubiquitin or dietary restriction pathway gene of interest can be detected using techniques established in the art. References sufficient to guide one of skill through these methods are readily available, including Ausubel, Sambrook and Berger (all infra). For example, expression level can be measured by measuring transcribed mRNA, e.g., via northern analysis, microarray analysis, or quantitative (e.g., real time) reverse transcription-PCR.

As another example, the level of expression is optionally measured by measuring the amount of translated protein. Protein expression levels can be measured, e.g., using immunoassays such as western blotting, dot blotting, ELISA, immunoPCR, and the like, or with proteomic detection methods which detect many proteins simultaneously, multidimensional gel electrophoresis, mass spectrometry based methods, or surface plasmon resonance techniques.

Expression levels can also be detected using reporter constructs, such as the GFP fusion proteins described above. Similarly, promoter regions of wwp-1, ubc-18, or other gene(s) of interest (e.g., generally sequences in the region of the start site of transcription, e.g., within 5 kb of the start site, e.g., 1 kb, or less e.g., within 500 bp or 250 bp or 100 bp of the start site) can be coupled to reporter constructs (CAT, beta-galactosidase, luciferase or any other available reporter) and can be similarly tested for expression modulation by the test compound.

Post-translational modification state of proteins (e.g., wwp-1 or a substrate thereof) can be detected using techniques like those described above for detection of protein expression. For example, a particular post-translationally modified form of a protein (or the unmodified form) can be detected by an immunoassay (e.g., western blotting, ELISA, or immunoPCR) using an antibody specific for that form. Phosphorylation of a protein can be detected, for example, using antibodies specific to phosphoserine, phosphothreonine, and/or phosphotyrosine or an antibody specific for a given phosphorylated form of the protein. As another example, phosphorylation can be detected by incorporation of a radioactively labeled phosphate group. Ubiquitination can be detected, for example, in an assay incorporating tagged ubiquitin as described in greater detail in the Examples section below.

Substrates of wwp-1 can be identified by techniques known in the art. For example, an in vitro ubiquitination reaction can be performed, e.g., using *C. elegans* extract as described in the Examples section below. Ubiquitinated proteins can then be identified, for example, by mass spectroscopic techniques, two dimensional electrophoresis and microsequencing, etc. Such substrates can themselves be involved in regulation of dietary restriction induced longevity. Substrates can also be identified by genetic pathway analysis and confirmed in an in vitro assay. Exemplary substrates of interest in the context of the present invention include, but are not limited to, cep-1/p53, pha-4/foxa, skn-1b, NF-E2, LKLF, KLF5, Runx2, LMP2A, OCT-4, endophilin, Notch, Occludin, HEF1, Smad7, JunB, c-Jun, p73, p63, CXCR4, Hrs, Nrf1 and Nrf2.

A large number of assays for detecting activity of various enzymes and other proteins have been described in the art. Activity of wwp-1 and/or ubc-18 (or homologs thereof) is optionally detected in an in vitro ubiquitination assay as described in the Examples section below. The substrate for such an activity assay can be, e.g., a native substrate or an exogenously supplied substrate. Activity is optionally normalized, e.g., to amount of cell extract, total protein concentration or amount of total protein, or concentration or amount of the enzyme of interest. Activity of a transcription factor can be assayed, e.g., by monitoring transcription of a marker or reporter gene having a binding site for the transcription factor in its promoter. In some instances, subcellular localization can be determined and correlated with activity (e.g., nuclear localization for a transcription factor that shuttles between the cytoplasm and the nucleus).

Level of autophagy can be determined by techniques known in the art. In one exemplary technique, a reporter construct that indicates the presence of autophagocytic vesicles is employed. For example, a GFP-tagged LGG-1 protein (or homolog thereof) can be visualized as described in Hansen et al. (2008) "A role for autophagy in the extension of lifespan by dietary restriction in *C. elegans*" PLoS Genetics 4(2):e24 and references therein. LGG-1 is incorporated into pre-autophagosomal and autophagosomal membranes. The GFP-LGG-1 reporter is localized to puncta in cells with increased numbers of autophagic vesicles, and the appearance of such puncta is employed as an indicator of autophagy, e.g., in *C elegans*. As other examples, autophagic vesicles can be imaged directly by electron microscopy (e.g., TEM), or a marker such as LC3-II can be assayed by immunoblotting, immunoprecipitation, or immunofluorescence (see, e.g., Tanida et al. (2008) "LC3 and autophagy" Methods Mol Bio 445:77-88).

It will be evident that detection of expression, activity, post-translational modification state, or autophagy in the cell includes techniques that involve lysis of the cell and measurement, e.g., in a cell lysate or extract, as well as techniques that measure expression, activity, etc. directly in the cell without requiring extraction or lysis.

In any of the assays herein, control compounds are optionally administered and the activity of the control compounds compared to those of the test compounds to verify that changes in activity resulting from application of the test compound are not artifacts. For example, control compounds can include various dyes, buffers, adjuvants, carriers, or the like that the test compounds are typically administered with, but lack a putative test compound.

Any of the assays herein are optionally performed in a high-throughput fashion, e.g., using automated fluid handling and/or detection systems, in a serial or parallel fashion.

Test compounds identified in cell-based assays as modulators of a wwp-1 ubiquitination pathway parameter are then optionally further assayed, e.g., for lifespan modulation, in a whole organism assay as described below.

Whole Organism Assays

In another aspect, the present invention provides screening assays in whole organisms. In a whole organism screening assay, as in the cell based systems described above, modulators for longevity or age-related disease are identified. The methods typically include providing an organism for screening, administering a test compound to the organism, and assaying for a change in a relevant parameter due to the presence of the test compound. In certain exemplary embodiments, expression of wwp-1 or ubc-18 has been altered in the animals employed, while in other exemplary embodiments, the animals exhibit wild-type expression of wwp-1 and ubc-18.

One general class of embodiments provides methods of screening for a modulator of longevity, in which a non-human animal that exhibits artificially altered expression or activity of wwp-1 or a homolog thereof and/or of ubc-18 or a homolog thereof is provided. A test compound is administered to the non-human animal, and a wwp-1 ubiquitination pathway parameter in the non-human animal is assayed. A change in the wwp-1 ubiquitination pathway parameter indicates the test compound modulates longevity. Typically, the change is observed, e.g., relative to a control animal not receiving the test compound (e.g., an isogenic or near-isogenic animal of similar age) or relative to the animal prior to administration of the compound.

As for the cell-based screening embodiments above, expression and activity can be altered using any of a wide variety of techniques known in the art, e.g., through recombinant DNA techniques, mutagenesis, or the like.

In one class of embodiments, the non-human animal exhibits reduced expression or activity of wwp-1 or the homolog thereof and/or reduced expression or activity of ubc-18 or the homolog thereof. For example, expression or activity can be reduced by at least 50%, at least 75%, or at least 90%, or can be undetectable. As just a few examples, expression and/or activity can be reduced using RNA interference or antisense techniques to decrease expression or through mutations (e.g., point mutations, insertions, or deletions) that decrease expression at an mRNA or protein level or that render the protein less active or inactive. In one embodiment, the non-human animal expresses a dominant negative form of wwp-1 or the homolog thereof or a dominant negative form of ubc-18 or the homolog thereof. Such animals exhibiting reduced expression or activity of wwp-1 or ubc-18 can be useful, for example, in screens for compounds that increase expression or activity of wwp-1, ubc-18, or a component downstream thereof.

In another class of embodiments, the non-human animal overexpresses wwp-1 or the homolog thereof and/or ubc-18 or the homolog thereof. For example, a transcript and/or translated product can be present in the animal (or selected cells thereof) at an amount that is at least 2×, at least 5×, at least 10×, at least 50×, or even at least 100× normal for that animal or cell type (including expression in an animal or cell not normally expressing the gene). In a related class of embodiments, the animal expresses a constitutively active form of wwp-1 or ubc-18; for example, wwp-1 with a mutation disrupting an inhibitory interaction between its WW and HECT domains.

In some embodiments, the artificial alteration in expression provides a convenient way to assay the wwp-1 ubiquitination pathway parameter. For example, the non-human animal can express a recombinant reporter construct whose expression is easily monitored, as described above. In one such embodiment, the cell expresses a fusion protein comprising GFP or a homolog thereof and either wwp-1 or a homolog thereof or ubc-18 or a homolog thereof, typically under control of an endogenous wwp-1 or ubc-18 (or homologous) promoter; see, e.g., the Examples section below. Changes in expression of wwp-1 or ubc-18 can thus be easily monitored by monitoring expression of the GFP moiety in the fusion protein. It will be evident that essentially any similar reporter can be substituted for GFP, e.g., another fluorescent moiety, a reporter enzyme, an epitope tag, etc. The reporter construct can replace the corresponding native gene or can be in addition to the native gene.

Suitable wwp-1 ubiquitination pathway parameters that can be assayed include, but are not limited to, one or more of lifespan (e.g., mean or median lifespan), an activity or expression level of wwp-1 or the homolog thereof, an activity or expression level of ubc-18 or the homolog thereof, an activity or expression level of pha-4 or a homolog thereof (e.g., mammalian foxa1, foxa2, or foxa3) or another downstream factor (e.g., a sod such as sod-1, sod-2, sod-4, or sod-5), post-translational modification state of wwp-1 or the homolog thereof, post-translational modification state of a substrate of wwp-1 (or ubc-18) or the homolog thereof, and level of autophagy. Other parameters that can optionally be assayed include, e.g., expression or activity level or post-translational modification state of autophagy pathway members such as rab-10, TOR, atg-1, vps-34, or bec-1 or a homolog thereof. Compounds that increase longevity or delay onset of age-related diseases can be identified, for example, as those that increase lifespan of the non-human animal, increase expression of wwp-1 or the homolog thereof, ubc-18 or the homolog thereof, or pha-4 or the homolog thereof; increase activity of wwp-1 or the homolog thereof, ubc-18 or the homolog thereof, or pha-4 or the homolog thereof, increase phosphorylation of wwp-1 or the homolog thereof, or increase ubiquitination of the substrate of wwp-1 (or ubc-18) or the homolog thereof, e.g., by at least 2×, at least 5×, at least 10×, at least 50×, or even at least 100×. Similarly, compounds of interest can increase autophagy (e.g., by at least 2×, at least 5×, at least 10×, at least 50×, or even at least 100×), decrease expression or activity of rab-10 or TOR or the homolog thereof, or increase expression or activity of atg-1, vps-34, or bec-1 or the homolog thereof.

Another general class of embodiments also provides methods of identifying a modulator of longevity. In these methods, a non-human animal is provided. A test compound is administered to the non-human animal, and expression or activity of wwp-1 or a homolog thereof, expression or activity of ubc-18 or a homolog thereof, and/or post-translational modification state of wwp-1 or a homolog thereof or a substrate thereof in the animal is monitored. A change (e.g., an increase) in expression or activity of wwp-1 or the homolog thereof, a change (e.g., an increase) in expression or activity of ubc-18 or the homolog thereof, altered (e.g., increased) phosphorylation of wwp-1 or the homolog thereof, and/or altered (e.g., increased) ubiquitination of the substrate indicates that the test compound modulates (e.g., increases) longevity. Typically, the change is observed, e.g., relative to a control animal not receiving the test compound (e.g., an isogenic or near-isogenic animal of similar age) or relative to the animal prior to administration of the compound. Similarly, other parameters related to the wwp-1/ubc-18 ubiquitin pathway or the autophagy pathway, as described herein, can be monitored.

As for the embodiments above, the animals optionally express a reporter construct that facilitates measurement of expression or activity. For example, the non-human animal can express a fusion protein comprising GFP or a homolog thereof and either wwp-1 or a homolog thereof or ubc-18 or a homolog thereof. In such embodiments, monitoring expression of wwp-1 or ubc-18 or the homolog thereof involves monitoring an optical signal from the GFP (e.g., using a fluorescence microscope, a fluorimeter, a plate reader, etc., whether manually or in an automated system, in the animal or in explants, cells, or extracts therefrom).

Yet another general class of embodiments provides methods of screening for a modulator of longevity and/or autophagy (e.g., dietary restriction-induced autophagy). In the methods, a non-human animal, preferably that exhibits artificially altered expression or activity of wwp-1 or a homolog thereof and/or of ubc-18 or a homolog thereof, is provided. A test compound is administered to the non-human animal, and an autophagy pathway parameter in the non-human animal is assayed. A change in the autophagy pathway parameter indicates the test compound modulates longevity and/or autophagy. Typically, the change is observed, e.g., relative to a control animal not receiving the test compound (e.g., an isogenic or near-isogenic animal of similar age) or relative to the animal prior to administration of the compound. Compounds of particular interest include those that increase autophagy, decrease expression or activity of rab-10 or TOR (including homologs thereof), or increase expression or activity of atg-1, vps-34, bec-1, or pha-4 (or a homolog of any thereof). Essentially all of the features for the embodiments above apply to these methods as well, as relevant.

Suitable non-human animals for use in the screens include vertebrates and invertebrates, mammals and other animals. Preferred organisms for screening for longevity modulators are nematodes (e.g., *C. elegans*) and flies (e.g., *Drosophila*), as well as typical mammalian laboratory animals such as mice, rabbits, and rats. The organisms are optionally wild-type organisms or transgenic animals as described herein. Typically, the organisms express wwp-1 or a homolog or ortholog thereof, ubc-18 or a homolog or ortholog thereof, and/or other gene(s) in the dietary restriction pathway. The animals optionally exhibit artificially altered expression of one, two, or more of wwp-1, ubc-18, and other genes that mediate dietary restriction induced longevity, and/or optionally exhibit artificially altered expression of or comprise mutations (e.g., loss of function mutations) in one or more genes in the insulin/IGF-1 and/or mitochondrial electron transport longevity pathways and/or autophagy pathway.

Typically, the animals are adult, e.g., mature, post-developmental, animals. For example, screening can be performed in adult *C. elegans*, adult *Drosophila*, adult rodents, etc. In one aspect, the roundworm *Caenorhabditis elegans* is used to assay for longevity modulators. *C. elegans* is a simple soil nematode species that has been extensively described at the cellular and molecular level, and is a model organism for biological studies. *C. elegans* can develop through a normal life cycle that involves four larval stages and a final molt into an adult hermaphrodite. The dauer pathway is an alternative life cycle stage common to many nematode species which is normally triggered by environmental stresses such as starvation, temperature extremes, or overcrowding. Genetically, the dauer pathway has been most intensively studied in *C. elegans*. However, in the present invention, the dauer pathway is typically avoided and adult nematodes are used, to avoid any interference between development pathways and longevity pathways.

As noted, the organisms are administered a test compound, e.g., a library of test compounds is administered to an array of organisms. Administration of the test compound is optionally by injection or by feeding the compound to the animal, or any other mode of administration that is optionally used for pharmaceuticals. The animals are also optionally subjected to dietary restriction, e.g., reduced caloric intake, during the screen, or the compounds can be tested without any dietary restrictions in place. It will be evident that the methods are frequently employed on populations of animals, e.g., populations of isogenic or near-isogenic animals; for example, the test compound can be administered to a population of animals and comparison made to a control population not receiving the compound.

The organisms are optionally observed to determine lifespan, e.g., a mean or median lifespan. Lifespan assays have been well described in the art. (See, e.g., Apfeld J. & Kenyon C. (1998) Cell 95: 199-210). In organisms that exhibit a modified lifespan, an agent is identified based on its ability to either extend or shorten the lifespan.

Techniques for assaying expression, activity, post-translational modification state, and autophagy have been described above. Again, it will be evident that detection of expression, activity, modification state, or autophagy in the animal includes techniques that involve removal of tissue, cells, bodily fluid, or the like from the animal and measurement, e.g., in a cell or tissue lysate or extract, as well as techniques that measure expression, activity, etc. directly in the animal without requiring extraction of a sample from the animal.

In any of the assays herein, control compounds are optionally administered and the activity of the control compounds compared to those of the test compounds to verify that changes in activity resulting from application of the test compound are not artifacts. For example, control compounds can include various dyes, buffers, adjuvants, carriers, or the like that the test compounds are typically administered with, but lack a putative test compound.

Any of the assays herein are optionally performed in a high-throughput fashion, e.g., using automated fluid handling and/or detection systems, in a serial or parallel fashion.

After identification of a modulator, additional assays are optionally conducted using the compound identified to further characterize the nature of the modulator's action with respect to longevity. For example, further studies of lifespan can be conducted and a phenotype such as egg laying can be measured to determine whether the longevity occurs by delaying maturity. Compounds identified using the screening methods herein are then optionally used as the active ingredient in pharmaceuticals that extend lifespan, e.g., to treat premature aging, extend normal lifespan, or delay onset of age related diseases.

High Throughput Screening and Screening Systems

High throughput methods of screening, e.g., drug screening, are particularly useful in identifying longevity modulators, e.g., modulators that affect wwp-1 or ubc-18 polypeptide activity or gene expression. Generally in these methods, a sample (e.g., a cell-free assay mixture, a cell, or a non-human animal, such as those described above) is contacted with or administered a test compound; typically, one or more of a panel or library of compounds is contacted or administered to each of a plurality of samples. Modulation of a relevant parameter (e.g., expression, activity, post-translational modification, binding, autophagy, or lifespan of the organism) by the test compounds is detected, thereby identifying one or more compound as a modulator or potential modulator. The assay methods of the present invention can be useful in performing high-throughput (e.g., greater than 1,000 compounds/day) and even ultra-high throughput (e.g., greater than 10,000 compounds/day) screening of chemical libraries, e.g., searching for modulators of longevity. These experiments may be carried out in parallel by a providing a large number of samples (e.g., reaction mixtures, cell suspensions, or organisms) in separate receptacles, typically in a multiwell or similar format, e.g., 96 well, 324 well or 1536 well plates. Different test compounds (library members) are added to separate wells, and the effect of the compound on the sample is ascertained, e.g., via lifespan determination, detection of expression, activity, post-translational modification, autophagy, or binding as described above. These parallel assays are generally carried out using specialized equipment to enable simultaneous processing of large numbers of samples, i.e., fluid handling by robotic pipettor systems and detection in multiplexed systems.

Automated systems of the invention can facilitate the screening methods described above (both in vitro and in vivo screening methods). That is, systems that facilitate cell-free, cell-based, or whole organism based screening for modulators of longevity or onset of age-related diseases are a feature of the invention. Similarly, systems designed to monitor physiological responses of animals, including non-human transgenic laboratory animals, are also a feature of the invention. System features herein are generally applicable to the methods herein and vice-versa.

Screening Systems

Systems (e.g., high-throughput automated systems) to identify modulators of longevity or age-related disease typically include an array of samples, e.g., any in vitro assay mixture, cell, or animal described herein. For example, the system can include an array of non-human animals, cells, or in vitro assay mixtures in containers (e.g., multiwell plates, tubes, etc.). A source of a plurality of test compounds is also typically included in such a system. A monitoring module (e.g., including a detector) monitors a relevant parameter in the samples, e.g., after contact with a test compound, and detects any changes in the parameter, and a correlation module (e.g., a computer) correlates any changes that occur with longevity modulation and the particular compound that initiated such change.

For example, one class of embodiments provides a system for screening for compounds that modulate longevity in which an array of non-human animals in containers (e.g., vials, tubes, boxes, cages, etc. as appropriate for the type of animal) is provided. The non-human animals exhibit artificially altered expression or activity of wwp-1 or a homolog thereof and/or of ubc-18 or a homolog thereof. The system also includes a monitoring module and a correlation module. After the animals are exposed to (e.g., injected or fed) one or more test compounds, the monitoring module is used to monitor a wwp-1 ubiquitination pathway parameter of the non-human animals in the array (e.g., used to determine lifespan or to detect an activity or expression level of wwp-1 or the homolog thereof, ubc-18 or the homolog thereof, or pha-4 or a homolog thereof, post-translational modification state of wwp-1 or the homolog thereof or a substrate thereof, or level of autophagy). The correlation module is then used to correlate a change in the wwp-1 ubiquitination pathway parameter (e.g., relative to an untreated animal) to longevity, thereby identifying any test compounds that modulate longevity.

Another exemplary class of embodiments also provides a system for screening for compounds that modulate longevity. In this class of embodiments, the system includes an array of non-human animals in containers, a monitoring module, and a correlation module. The monitoring module monitors expression or activity of wwp-1 or a homolog thereof, expression or activity of ubc-18 or a homolog thereof, and/or post-translational modification state of wwp-1 or a homolog thereof or a substrate thereof in the non-human animals in the array following administration of a test compound. The correlation module then correlates a change (e.g., an increase) in expression or activity of wwp-1 or the homolog thereof, a change (e.g., an increase) in expression or activity of ubc-18 or the homolog thereof, altered (e.g., increased) phosphorylation of wwp-1 or the homolog thereof, and/or altered (e.g., increased) ubiquitination of the substrate (e.g., relative to an untreated animal) to longevity, thereby identifying the compounds that modulate longevity. Similarly, other parameters related to the wwp-1/ubc-18 ubiquitin pathway or the autophagy pathway, as described herein, can be monitored.

The non-human animals can be essentially any of those described herein, as appropriate, for example, wild-type animals, animals exhibiting reduced expression or activity of wwp-1 or a homolog thereof and/or reduced expression or activity of ubc-18 or a homolog thereof, animals that overexpress wwp-1 or a homolog thereof and/or ubc-18 or a homolog thereof, or animals expressing recombinant reporter constructs. Similarly, the non-human animals can be nematodes (e.g., C. elegans), flies (e.g., Drosophila), rodents, etc. Typically, the animals are adults. The animals whose phenotype is to be analyzed are optionally part of the system, or they can be considered separate from it.

Arrays of the invention can be standard gridded arrays that have a logical spatial relationship among members of the array, e.g., C. elegans in multiwell plates or vials of Drosophila in a rack. The array can also be a "logical array" in which the members of the array are linked by a look-up table that tracks array members, such as individual wells or vials. In the latter series of embodiments, standard tracking software can be used to track well or vial positions, and different logical arrays, e.g., sets of wells or vials, can be treated with one or more different modulators. In the case where the arrays are arranged in a standard spatial arrangement, the entire array, or selected members, can be treated with one or more modulators and the effects observed.

Test Compound Libraries

Essentially any available compound library can be screened, e.g. in a high-throughput format, in the systems herein. A number of suitable test compounds and libraries thereof have been noted above. Additional libraries exist, many of which are commercially available, e.g., from Sigma-Aldrich (St. Louis Mo.); Actimol (Newark Del.), providing e.g., the Actiprobe 10 and Actiprobe 25 libraries of 10,000 and 25,000 compounds, respectively; BioMol (Philadelphia, Pa.), providing a variety of libraries, including natural compound libraries and the SCREEN-WELL™ Ion Channel ligand library as well as several other application specific libraries; Enamine (Kiev, Ukranie) which produces custom libraries of billions of compounds from thousands of different building blocks; TimTec (Newark Delaware), which produces general screening stock compound libraries containing>100,000 compounds, as well as template-based libraries with common heterocyclic lattices, libraries for targeted mechanism based selections, including kinase modulators, GPCR ligands, channel modulators, etc., privileged structure libraries that include compounds containing chemical motifs that are more frequently associated with higher biological activity than other structures, diversity libraries that include compounds pre-selected from available stocks of compounds with maximum chemical diversity, plant extract libraries, natural products and natural product-derived libraries, etc; AnalytiCon Discovery (Germany) including NatDiverse (natural product analogue screening compounds) and MEGAbolite (natural product screening compounds); Chembridge (San Diego, Calif.) including a wide array of targeted or general and custom or stock libraries; ChemDiv (San Diego, Calif.) providing a variety of compound diversity libraries including CombiLab and the International Diversity Collection; Comgenix (Hungary) including ACTIVERSE™ libraries; MicroSource (Gaylordsville, Conn.) including natural libraries, agro libraries, the NINDS custom library, the genesis plus library and others; Polyphor (Switzerland) including privileged core structures as well as novel scaffolds; Prestwick Chemical (Washington D.C.), including the Prestwick chemical collection and others that are pre-screened for biotolerance; Tripos (St. Louis, Mo.), including large lead screening libraries; and many others. Academic institutions such as the Zelinsky Institute of Organic Chemistry (Russia) also provide libraries of considerable structural diversity that can be screened in the methods of the invention, e.g., to find longevity modulators.

The format of the library will vary depending on the system to be used. In one typical embodiment, libraries of test compounds and/or sample materials are arrayed in microwell plates (e.g., 96, 384 or more well plates), which can be accessed by standard fluid handling robotics, e.g., using a pipettor or other fluid handler with a standard ORCA robot (Optimized Robot for Chemical Analysis) available from Beckman Coulter (Fullerton, Calif.). Standard commercially available workstations such as the Caliper Life Sciences (Hopkinton, Mass.) Sciclone ALH 3000 workstation and RAPIDPLATE™ 96/384 workstation provide precise 96 and 384-well fluid transfers in a small, highly scalable format. Plate management systems such as the Caliper Life Sciences TWISTER® II Advanced Capability Microplate Handler for End-Users, OEM's and Integrators provide plate handling, storage and management capabilities for fluid handling, while the PRESTO™ AutoStack provides fast reliable access to consumables presenting trays of tips, reagents, microplates or deep wells to an automated device (e.g., the ALH 3000) without robotic arm intervention.

Microfluidic systems for handling and analyzing microscale fluid samples, e.g., in cell based and non-cell based approaches that can be used for analysis of test compounds on biological samples in the present invention are also available, e.g., the Caliper Life Sciences various LABCHIP® technologies (e.g., LABCHIP® 90 and 3000) and Agilent Technologies (Palo Alto, Calif.) 2100 and 5100 devices. Similarly, interface devices between microfluidic and standard plate handling technologies are also commercially available. For example, the Caliper Technologies LABCHIP® 3000 uses "sipper chips" as a "chip-to-world" interface that allows automated sampling from microtiter plates. To meet the needs of high-throughput environments, the LABCHIP® 3000 employs four or even twelve sippers on a single chip so that samples can be processed, in parallel, up to twelve at a time. Solid phase libraries of materials can also be conveniently accessed using sipper or pipetting technology, e.g., solid phase libraries can be gridded on a surface and dried for later rehydration with a sipper or pipette and accessed through the sipper or pipette. These sources are optionally used with whole organism, cell based, and/or cell free screening systems. For example, a library of test compounds in a microtiter plate can be accessed via a sipper or pipettor device into an array of containers or microchannels containing cells or organisms for screening as described above.

System Components

Although the devices and systems specifically illustrated herein are generally described in terms of the performance of a few or one particular operation, it will be readily appreciated from this disclosure that these systems permit easy integration of additional operations. For example, the systems described will optionally include structures, reagents and systems for performing virtually any number of operations both upstream and downstream from the operations specifically described herein. Such upstream operations include sample handling and preparation operations, e.g., cell separation, extraction, purification, culture, amplification, cellular activation, labeling reactions, dilution, aliquotting, and the like. Similarly, downstream operations may include similar operations, including, e.g., separation of sample components, labeling of components, assays and detection operations, movement of components into contact with cells or organisms, or the like.

Upstream and downstream assay and detection operations include, without limitation, fluorescence assays, activity assays, receptor/ligand assays, immunoassays, nucleic acid amplification, binding assays, lifespan determination, and the like. Any of these elements can be incorporated into the systems herein.

In general in the present invention, materials such as cells and organisms are optionally monitored and/or detected so that lifespan or expression, activity, or post-translational modification can be determined. Depending on the measurement made, decisions can be made regarding subsequent operations, e.g., whether to further assay a particular modulator in detail to determine the extent of lifespan modulation, such as whether diet restriction is necessary for the modulator to work and whether the modulator also delays onset of age-related diseases.

The systems described herein generally include fluid handling devices, as described above, in conjunction with additional instrumentation for controlling fluid transport, flow rate and direction within the devices, detection instrumentation for detecting or sensing results of the operations performed by the system, processors, e.g., computers, for instructing the controlling instrumentation in accordance with preprogrammed instructions, receiving data from the detection instrumentation, and for analyzing, storing and interpreting the data, and providing the data and interpretations in a readily accessible reporting format.

Controllers

A variety of controlling instrumentation is optionally utilized in conjunction with the fluid handling elements described above, for controlling the transport and direction of fluids and/or materials (samples, reaction mixtures, cells, test compounds, etc.) within the systems of the present invention. Controllers typically include appropriate software to direct fluid and material transport in response to user instructions. For example, software that directs the amount of nutrition/food to be fed to an array of nematodes can be included in a system of the present invention to allow a user to alter the dietary restriction profile for an array of nematodes being screened. Software that allows a user to direct a particular RNAi molecule to be administered to a cell or organism allows a user to selectively knock out a gene, such as wwp-1 and/or ubc-18, when screening for longevity modulators.

Typically, the controller systems are appropriately configured to receive or interface with a fluid handling or other system element as described herein. For example, the controller and/or detector optionally includes a stage upon which a sample is mounted to facilitate appropriate interfacing between the controller and/or detector and the rest of the system. Typically, the stage includes an appropriate mounting/alignment structural elements, such as a nesting well, alignment pins and/or holes, asymmetric edge structures (e.g., to facilitate proper alignment of slides, microwell plates or microfluidic "chips"), and the like.

Detectors

Within the systems of the invention, detectors can take any of a variety of forms. The various fluid handling stations noted above often come with integrated detectors, e.g., optical or fluorescent detectors. However, other detectors such as one that measures lifespan are also optionally used.

System signal detectors are typically disposed adjacent to a site of reaction or mixing between a cell sample or organism and a test compound. This site can be a test tube, microwell plate, microfluidic device, or the like. The site is within sensory communication of the detector. The phrase "within sensory communication" generally refers to the relative location of the detector that is positioned relative to the site so as to be able to receive a particular relevant signal from that container. In the case of optical detectors, e.g., fluorescence, FRET, or fluorescence polarization detectors, sensory communication typically means that the detector is disposed sufficiently proximal to the container that optical, e.g., fluorescent signals, are transmitted to the detector for adequate detection of those signals. Typically this employs a lens, optical train or other detection element, e.g., a CCD, that is focused upon a relevant portion of the container to efficiently gather and record these optical signals.

Exemplary detectors include, but are not limited to, photo multiplier tubes, a spectrophotometer, a fluorimeter, a CCD array, a scanning detector, a microscope, or the like. Cells, dyes or other components which emit a detectable signal can be flowed past or moved into contact with the detector, or, alternatively, the detector can move relative to an array of samples (or, the detector can simultaneously monitor a number of spatial positions corresponding to samples, e.g., as in a CCD array). For example, a microscope is optionally moved relative to an array of nematodes in containers, e.g., to determine whether the organism in a particular container is alive at any given time point.

The system typically includes a signal detector located proximal to the site of mixing/reaction. The signal detector detects the detectable signal, e.g., for a selected length of time. For example, the detector can include a spectrophotometer or other optical detection element. Commonly, the signal detector is operably coupled to a computer, which deconvolves the detectable signal to provide an indication of a relevant parameter, such as lifespan, protein activity, gene expression, etc. Changes in the relevant parameter(s) are monitored in response to a test compound (e.g., putative modulator), e.g., as compared to a control that does not include the test compound.

Computer

The system typically includes (e.g., in the correlation module, e.g., in a processor or computer) system instructions that correlate a relevant parameter with a predicted longevity phenotype, e.g., instructions that correlate gene expression, protein activity, protein post-translational modification level, or lifespan with increased or decreased longevity. The system instructions can compare detected information as to the parameter with a database that includes correlations between values of the parameter and the relevant phenotypes. This database can be multidimensional, thereby including higher-order relationships between combinations of parameters or other information and the relevant phenotypes. These relationships can be stored in any number of look-up tables, e.g., taking the form of spreadsheets (e.g., EXCEL™ spreadsheets) or databases such as an ACCESS™, SQL™, ORACLE™, PARADOX™, or similar database. The system can include provisions for inputting animal-specific information regarding parameter information, e.g., through an automated or user interface, and for comparing that information to the look up tables.

The correlation module can include software that tracks and analyzes data relationships. For example, Partek Incorporated (St. Peters, Missouri; www (dot) partek (dot) com) provides software for pattern recognition (e.g., Partek Pro 2000 Pattern Recognition Software) which can be applied to, e.g., principle component analysis, genetic algorithms for multivariate data analysis, interactive visualization, variable selection, and neural and statistical modeling. Relationships can be analyzed, e.g., by principal components analysis mapped scatterplots and biplots, multi-dimensional scaling mapped scatterplots, Star plots, etc. The software of the system can be heuristic in nature, e.g., by including neural networks or statistical methods to detect and analyze data relationships. For example, neural net approaches can be coupled to genetic algorithm-type programming for heuristic development of a modulator-trait data space model. For example, NNUGA (Neural Network Using Genetic Algorithms) is an available program (e.g., on the world wide web at cs (dot) bgu (dot) ac (dot) il/~omri/NNUGA) which couples neural networks and genetic algorithms. An introduction to neural networks can be found, e.g., in Kevin Gurney (1999) *An Introduction to Neural Networks*, UCL Press, 1 Gunpowder Square, London EC4A 3DE, UK. and on the world wide web at shef (dot) ac (dot) uk/psychology/gurney/notes/index (dot) html. Additional useful neural network references include, e.g., Christopher M. Bishop (1995) *Neural Networks for Pattern Recognition* Oxford Univ Press; ISBN: 0198538642; Brian D. Ripley, N. L. Hjort (Contributor) (1995) *Pattern Recognition and Neural Networks* Cambridge University Press (Short); ISBN: 0521460867. The correlation module can include any available statistical tool for detecting, correlating, predicting or analyzing modulator data, including multidimensional data as noted above.

For example, the system instructions can include software that accepts information associated with any detected parameter information, e.g., an indication that a subject with the relevant parameter value has a particular phenotype. This software can be heuristic in nature, using such inputted associations to detect correlations, or to improve the accuracy of the look up tables and/or interpretation of the look up tables by the system. A variety of such approaches, including principle component analysis, neural networks, genetic algorithms, Markov modeling, and other statistical analysis are known in the art and can be incorporated into the system software.

Also, in screening systems of the invention, either or both of the controller system and/or the detection system are optionally coupled to an appropriately programmed processor or computer which functions to instruct the operation of these instruments in accordance with preprogrammed or user input instructions, receive data and information from these instruments, and interpret, manipulate and report this information to the user. As such, the computer is typically appropriately coupled to one or both of these instruments (e.g., including an analog to digital or digital to analog converter as needed).

The computer typically includes appropriate software for receiving user instructions, either in the form of user input into a set parameter fields, or in the form of preprogrammed instructions, e.g., preprogrammed for a variety of different specific operations. For example, a user may input the amount of nutrients a nematode is to receive or the wwp-1 ubiquitination pathway parameter that is to be measured. The software then converts these instructions to appropriate language for instructing, e.g., the operation of the fluid direction and transport controller to carry out further desired operations. The computer then receives the data from the one or more sensors/detectors included within the system, and interprets the data, either provides it in a user understood format, or uses that data to initiate further controller instructions, in accordance with the programming, e.g., such as in monitoring and control of flow rates, temperatures, further assays, and the like. For example, the computer correlates which test compounds were capable of binding to wwp-1 (or ubc-18, a kinase, a phosphatase, etc.) in a cell free assay and then selects and initiates instruction that those compounds be used in cell-based assays that measure expression or activity levels or whole organism assays that measure lifespan.

Optionally, system components for interfacing with a user are provided. For example, the systems can include a user viewable display for viewing an output of computer-implemented system instructions, user input devices (e.g., keyboards or pointing devices such as a mouse) for inputting user commands and activating the system, etc. Typically, the system of interest includes a computer, wherein the various computer-implemented system instructions are embodied in computer software, e.g., stored on computer readable media.

In addition to statistical software, standard desktop applications such as word processing software (e.g., MICROSOFT WORD™ or COREL WORDPERFECT™) and database software (e.g., spreadsheet software such as MICROSOFT EXCEL™, COREL QUATTRO PRO™, or database programs such as MICROSOFT ACCESS™ or SEQUEL™, ORACLE™, PARADOX™) can be adapted to the present invention by inputting a character string corresponding to a modulator, a behavior or other trait herein, or to an association between a modulator or parameter or other trait and a phenotype. Suitable software can also easily be constructed by one of skill using a standard programming language such as Visualbasic, Fortran, Basic, Java, or the like.

As noted, systems can include a computer with an appropriate database and a behavior or correlation of the invention. Data sets entered into the software system comprising any of the wwp-1 ubiquitination pathway parameters or parameter-phenotype correlations herein can be a feature of the invention. The computer can be, e.g., a PC (Intel x86 or Pentium chip-compatible DOS™, OS2™ WINDOWS™ WINDOWS NT™, WINDOWS95™, WINDOWS98™, WINDOWS2000, WINDOWSME, WINDOWS VISTA, or LINUX based machine, a MACINTOSH™, Power PC, or a UNIX based (e.g., SUN™ work station or LINUX based machine) or other commercially common computer which is known to one of skill.

Biosensors

Biosensors of the invention are devices or systems that comprise the polypeptides or nucleic acids of the invention (e.g., a wwp-1 or ubc-18 polypeptide or nucleic acid) coupled to a readout that measures or displays one or more activity of the polypeptide or nucleic acid. Thus, any of the above described assay components can be configured as a biosensor by operably coupling the appropriate assay components to a readout. The readout can be optical (e.g., to detect cell markers, ion-sensitive dyes, cell potential, or cell survival), electrical (e.g., coupled to a FET, a BIAcore, or any of a variety of others), spectrographic, or the like, and can optionally include a user-viewable display (e.g., a CRT or optical viewing station). The biosensor can be coupled to robotics or other automation, e.g., microfluidic systems, that direct contact of the test compounds to the proteins of the invention, e.g., for automated high-throughput analysis of test compound activity. A large variety of automated systems that can be adapted to use with the biosensors of the invention are commercially available. For example, automated systems have been made to assess a variety of biological phenomena, including, e.g., expression levels of genes in response to selected stimuli (Service (1998) "Microchips Arrays Put DNA on the Spot" *Science* 282:396-399). Laboratory systems can also perform, e.g., repetitive fluid handling operations (e.g., pipetting) for transferring material to or from reagent storage systems that comprise arrays, such as microtiter trays or other chip trays, which are used as basic container elements for a variety of automated laboratory methods. Similarly, the systems manipulate, e.g., microtiter trays, and control a variety of environmental conditions such as temperature, exposure to light or air, and the like. Many such automated systems are commercially available. Examples of automated systems are available from Caliper Technologies (including the former Zymark Corporation, Hopkinton, Mass.), which utilize various Zymate systems that typically include, e.g., robotics and fluid handling modules. Similarly, the common ORCA® robot, which is used in a variety of laboratory systems, e.g., for microtiter tray manipulation, is also commercially available, e.g., from Beckman Coulter, Inc. (Fullerton, Calif.). A number of automated approaches to high-throughput activity screening are provided by the Genomics Institute of the Novartis Foundation (La Jolla, Calif.); See GNF.org on the world-wide web. Microfluidic screening applications are also commercially available from Caliper Technologies Corp. For example, (e.g., LABMICROFLUIDIC DEVICE® high throughput screening system (HTS) by Caliper Technologies, Mountain View, Calif. or the HP/Agilent technologies Bioanalyzer using LABCHIP™ technology by Caliper Technologies Corp. can be adapted for use in the present invention.

In an alternate embodiment, conformational changes are detected by coupling the polypeptides or complexes of the invention to an electrical readout, e.g., to a chemically coupled field effect transistor (a CHEM-FET) or other appropriate system for detecting changes in conductance or other electrical properties brought about by a conformational shift by the protein of the invention, e.g., by binding of a test compound to a polypeptide or gene of the invention.

Modulating Longevity

Compounds identified as described above or any other compounds that modulate longevity, e.g., through the dietary restriction pathway based on wwp-1 and ubc-18, are another feature of the invention. The compounds of the invention are typically administered to a subject or patient, e.g., to increase longevity, to treat premature aging, delay the onset of age-related diseases, such as some cancers, or enhance quality of life during the later part of a subject's lifespan, e.g., by preventing or alleviating symptoms of aging such as cognitive and motor deficits. The subject is optionally treated once with a compound that acts over an extended period of time or given daily, weekly, or monthly doses or the like for a shorter acting compound. In addition, a subject can be subjected to dietary restriction while on a pharmaceutical dosing regimen to extend longevity, or the compound used can act in the absence of any dietary restrictions.

In one aspect, the invention provides methods for modulating (e.g., increasing) longevity of an animal. In the methods, expression or activity of wwp-1 or a homolog thereof and/or of ubc-18 or a homolog thereof in the animal is modulated (e.g., increased), e.g., relative to a control or untreated animal. For example, expression of wwp-1 or the homolog thereof, activity of wwp-1 or the homolog thereof, phosphorylation of wwp-1 or the homolog thereof, or expression or activity of ubc-18 or the homolog thereof can be increased.

Modulation can be effected, for example, by administration of a longevity modulator that affects wwp-1 or the homolog thereof or ubc-18 or the homolog thereof, by overexpression or inhibition of expression of wwp-1 and/or ubc-18, or similar techniques. Exemplary modulators have been described herein, and include, for example, compounds that increase expression of wwp-1 or the homolog thereof, compounds that increase activity of wwp-1 or the homolog thereof (e.g., by decreasing expression or activity of a phosphatase that dephosphorylates wwp-1 or the homolog thereof or by increasing expression or activity of a kinase that phosphorylates wwp-1 or the homolog thereof), and compounds that increase expression or activity of ubc-18 or the homolog thereof. Modulation can be, e.g., relative to the animal before such treatment or relative to a control, untreated animal.

The animal can be a human, or it can be a non-human animal. The animal is optionally also subjected to dietary restriction.

A related aspect provides methods of delaying onset of an age-related disease such as cancer, diabetes, a cardiovascular disease, or a neurodegenerative disease in an animal. In these methods, expression or activity of wwp-1 or a homolog thereof and/or of ubc-18 or a homolog thereof in the animal is modulated (e.g., increased or decreased), e.g., relative to a control or untreated animal. As for the embodiments above, modulation can be effected, e.g., by administration of a longevity modulator that affects wwp-1 or the homolog thereof or ubc-18 or the homolog thereof. The animal can be a human, or it can be a non-human animal. The animal is optionally also subjected to dietary restriction.

Given that human wwp1 is a potential oncogene shown to be amplified in breast and prostate cancers (Chen et al. (2007) "The amplified WWP1 gene is a potential molecular target in breast cancer" Int J. Cancer. 121(1):80-87 and Chen et al. (2007) "Ubiquitin E3 ligase WWP1 as an oncogenic factor in human prostate cancer" Oncogene 26(16):2386-94) and that wwp1 and itch negatively regulate tumor suppressor p53 and its paralog p73 (Laine and Ronai (2007) "Regulation of p53 localization and transcription by the HECT domain E3 ligase WWP1" Oncogene 26(10):1477-83), in embodiments in which human wwp1 is activated or overexpressed, such activation or overexpression is preferably accomplished in adults in differentiated or post-mitotic cells, and the subject is closely monitored for undesirable side effects. For embodiments in which downregulation of wwp1 is desired (e.g., such cancers), inhibitors of wwp1 expression or activity identified as described herein are useful therapeutics.

Therapeutic Administration of Modulators

Various aspects of the invention involve administration of a modulator to a human patient or non-human animal. In embodiments in which a modulator is administered, particularly to a human, for example, to treat an age-related disease or disorder or increase longevity, compositions for administration typically comprise a therapeutically effective amount of the modulator (i.e., an amount that is effective for preventing, ameliorating, delaying onset of, or treating a disease or disorder, preventing or ameliorating physiological effects of aging, extending lifespan, or the like) and a pharmaceutically acceptable carrier or excipient. Such a carrier or excipient includes, but is not limited to, saline, buffered saline, dextrose, water, glycerol, ethanol, and/or combinations thereof. Pharmaceutically acceptable carriers are determined in part by the particular composition being administered, as well as by the particular method used to administer the composition. Accordingly, there is a wide variety of suitable formulations of pharmaceutical compositions of the present invention.

Therapeutic compositions comprising one or more modulators of the invention are optionally tested in one or more appropriate in vitro and/or in vivo animal model of disease, to confirm efficacy, tissue metabolism, and to estimate dosages, according to methods well known in the art. In particular, dosages can initially be determined by activity, stability or other suitable measures of the formulation.

Compositions can be administered by a number of routes including, but not limited to: oral, intravenous, intraperitoneal, intramuscular, transdermal, subcutaneous, topical, sublingual, or rectal administration. Such administration routes and appropriate formulations are generally known to those of skill in the art.

The compositions, alone or in combination with other suitable components, can also be made into aerosol formulations (i.e., they can be "nebulized") to be administered via inhalation. Aerosol formulations can be placed into pressurized acceptable propellants, such as dichlorodifluoromethane, propane, nitrogen, and the like. Formulations suitable for parenteral administration, such as, for example, by intraarticular (in the joints), intravenous, intramuscular, intradermal, intraperitoneal, and subcutaneous routes, include aqueous and non-aqueous, isotonic sterile injection solutions, which can contain antioxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. The formulations can be presented in unit-dose or multi-dose sealed containers, such as ampules and vials.

For longevity extension or prevention or treatment of disease, the appropriate dosage of a modulator, e.g., identified by the methods provided herein, will depend on the type of disease to be treated, e.g., premature aging or extension of lifespan in a mature adult, the severity and course of the disease, whether the modulator is administered for preventive or therapeutic purposes, previous therapy, the patient's clinical history, and the discretion of the attending physician. The compound or combination of compounds is suitably administered to the patient in one dose or more typically over a series of treatments.

The dose administered to a patient, in the context of the present invention, is sufficient to effect a beneficial, e.g., prophylactic and/or therapeutic, response in the patient over time. The dose is determined, e.g., by the efficacy of the particular compound or other formulation and the condition of the patient, as well as the body weight or surface area of the patient to be treated. The size of the dose is also determined by the existence, nature, and extent of any adverse side effects that accompany the administration of a particular formulation in a particular patient. In determining the effective amount of the modulator or formulation to be administered in the treatment of disease or extension of lifespan, the physician evaluates such factors as circulating plasma levels of the modulator, formulation toxicities, and progression of any relevant disease.

For administration, formulations of the present invention are optionally administered at a rate determined by the LD-50 of the relevant formulation, and/or observation of any side effects of the modulators of the invention at various concentrations, e.g., as applied to the mass or topical delivery area and overall health of the patient. As will be understood by those of ordinary skill in the art, the appropriate doses of compounds of the invention (e.g., polypeptides, antisense, RNAi molecules, antibodies, drugs, etc.) will be generally around those already employed in clinical therapies wherein similar moieties are administered alone or in combination with other therapeutics. The physician administering treatment will be able to determine the appropriate dose for the individual subject. The progress of the therapy of the invention is easily monitored by conventional techniques and assays; the efficacy of a therapeutic method of the invention over time can be identified by an absence of symptoms or clinical signs, e.g., by delayed onset of age-related conditions, and by lifespan extension, e.g., beyond an average age for a particular population.

If a patient undergoing treatment develops fevers, chills, or muscle aches, he/she receives the appropriate dose of aspirin, ibuprofen, acetaminophen or other pain/fever controlling drug. Patients who experience reactions to the compositions, such as fever, muscle aches, and chills are premedicated 30 minutes prior to the future infusions with either aspirin, acetaminophen, or, e.g., diphenhydramine. Meperidine is used for more severe chills and muscle aches that do not quickly respond to antipyretics and antihistamines. Treatment is slowed or discontinued depending upon the severity of the reaction.

Another aspect of the invention is gene therapy to extend longevity, e.g., in human or veterinary subjects. In these applications, the nucleic acids of the invention are optionally cloned into appropriate gene therapy vectors (and/or are simply delivered as naked or liposome-conjugated nucleic acids), which are then delivered, optionally in combination with appropriate carriers or delivery agents. Proteins can also be delivered directly, but delivery of the nucleic acid is typically preferred in applications where stable expression is desired.

Vectors for administration typically comprise wwp-1 and/or ubc-18 genes under the control of a promoter that is expressed in a cell of interest. These can include native wwp-1 and/or ubc-18 promoters and/or upstream regulatory elements, or other cell specific promoters known to those of skill in the art. Compositions for administration typically comprise a therapeutically effective amount of the gene therapy vector or other relevant nucleic acid, and a pharmaceutically acceptable carrier or excipient and are formulated to suit the mode of administration. Administration is by any of the routes normally used for introducing a molecule into ultimate contact with cells of interest. Practitioners can select an administration route of interest based on the cell target. Suitable methods of administering such nucleic acids are available and known to those of skill in the art.

The dose administered to a patient, in the context of the present invention, is sufficient to effect a beneficial therapeutic response in the patient over time, e.g., extension of lifespan or a halt or delay in the progression of age-related diseases. The dose is determined by the efficacy of the particular vector or other formulation, the activity, stability or serum half-life of the polypeptide which is expressed, and the condition of the patient, as well as the body weight or surface area of the patient to be treated. The size of the dose is also determined by the existence, nature, and extent of any adverse side effects that accompany the administration of a particular vector, formulation, or the like in a particular patient. In determining the effective amount of the vector or formulation to be administered in the treatment of disease, a physician evaluates local expression in the tissue or cell of interest or circulating plasma levels, formulation toxicities, progression of the relevant disease, and/or, where relevant, the production of antibodies to proteins encoded by the polynucleotides. The dose administered is typically in the range equivalent to dosages of currently-used therapeutic proteins, adjusted for the altered activity or serum half-life of the relevant composition. The vectors of this invention can supplement treatment conditions by any known conventional therapy, e.g., diet restriction.

Kits

In other embodiments, the invention provides a kit useful for the methods and modulators described herein. Such kits optionally comprise one or more containers, labels, and instructions, as well as components for assaying and identifying potential modulators of the dietary restriction pathway. For example, a kit optionally contains an array of nematodes in containers along with a module for assaying lifespan of the nematodes when exposed to various test compounds.

In many embodiments, the kits comprise instructions (typically written instructions) relating to the use of the kit to identify longevity modulators. In some embodiments, the kits comprise a URL address or phone number or the like for users to contact for instructions or further instructions.

Molecular Biological Techniques

In practicing the present invention, many conventional techniques in molecular biology, microbiology, and recombinant DNA technology are optionally used. These techniques are well known and are explained in, for example, Berger and Kimmel, *Guide to Molecular Cloning Techniques, Methods in Enzymology volume* 152 Academic Press, Inc., San Diego, Calif.; Sambrook et al., *Molecular Cloning—A Laboratory Manual* (3rd Ed.), Vol. 1-3, Cold Spring Harbor Laboratory, Cold Spring Harbor, N.Y., 2000; and *Current Protocols in Molecular Biology*, F. M. Ausubel et al., eds., Current Protocols, a joint venture between Greene Publishing Associates, Inc. and John Wiley & Sons, Inc., (supplemented through 2008). For a description of the basic paradigm of molecular biology, including the expression (transcription and/or translation) of DNA into RNA into protein, see, e.g., Alberts et al. (2002) *Molecular Biology of the Cell, 4th Edition* Taylor and Francis, Inc., and Lodish et al. (1999) *Molecular Cell Biology, 4th Edition* W H Freeman & Co. Other useful references, e.g. for cell isolation and culture include Freshney (1994) *Culture of Animal Cells, a Manual of Basic Technique*, third edition, Wiley-Liss, New York and the references cited therein and Atlas and Parks (Eds.) *The Handbook of Microbiological Media* (1993) CRC Press, Boca Raton, Fla.

Methods of making nucleic acids (e.g., by in vitro amplification, purification from cells, or chemical synthesis), methods for manipulating nucleic acids (e.g., site-directed mutagenesis, by restriction enzyme digestion, ligation, etc.), and various vectors, promoters, cell lines and the like useful in manipulating and making nucleic acids and polypeptides are described in the above references. For example, common vectors include, e.g., plasmids, cosmids, viruses, YACs, etc., and typically have one or more origins of replication, one or more sites into which recombinant DNA can be conveniently inserted, and one or more selectable markers for selecting cells containing vectors from those without. Expression vectors comprising elements that provide for or facilitate transcription of nucleic acids which are cloned into the vectors are also widely available; such elements include, e.g., transcription and translation terminators, transcription and translation initiation sequences, and promoters and/or enhancers useful for regulation of the expression of the particular target nucleic acid. A plethora of kits are commercially available for the preparation, purification, and cloning of plasmids or other relevant nucleic acids from cells, e.g., STRATACLEAN™ from Stratagene and QIAPREP™ from Qiagen. Any isolated and/or purified nucleic acid can be further manipulated to produce other nucleic acids, used to transfect cells, incorporated into related vectors to infect organisms, or the like. In addition, essentially any polynucleotide can be custom or standard ordered from any of a variety of commercial sources, such as The Midland Certified Reagent Company (www (dot) mcrc (dot) oligos (dot) com), The Great American Gene Company (www (dot) genco (dot) com), ExpressGen Inc. (www (dot) expressgen (dot) corn), Operon Technologies Inc. (Alameda, Calif.), and many others.

In addition to the various references noted above, a variety of protein manipulation and detection methods are well known in the art, including, e.g., those set forth in R. Scopes, *Protein Purification*, Springer-Verlag, N.Y. (1982); Deutscher, *Methods in Enzymology Vol.* 182: *Guide to Protein Purification*, Academic Press, Inc. N.Y. (1990); Sandana (1997) *Bioseparation of Proteins*, Academic Press, Inc.; Bollag et al. (1996) *Protein Methods, 2nd Edition* Wiley-Liss, NY; Walker (1996) *The Protein Protocols Handbook* Humana Press, NJ; Harris and Angal (1990) *Protein Purification Applications: A Practical Approach* IRL Press at Oxford, Oxford, England; Harris and Angal *Protein Purification Methods: A Practical Approach* IRL Press at Oxford, Oxford, England; Scopes (1993) *Protein Purification: Principles and Practice 3rd Edition* Springer Verlag, NY; Janson and Ryden (1998) *Protein Purification: Principles, High Resolution Methods and Applications, Second Edition* Wiley-VCH, NY; and Walker (1998) *Protein Protocols on CD-ROM* Humana Press, NJ; and the references cited therein. Additional details regarding protein purification and detection methods can be found in Satinder Ahuja ed., *Handbook of Bioseparations*, Academic Press (2000).

Regulating Expression of Dietary Restriction Related Genes

Expression (e.g., transcription and/or translation) of wwp-1, ubc-18, or other genes of interest can be altered using any of a variety of techniques known in the art, as noted above. For example, gene expression can be inhibited in cells or organisms using an antisense nucleic acid or an interfering RNA (RNAi), e.g., to decrease or knock out expression of wwp-1 and/or ubc-18; see, e.g., the Examples section herein. Similarly, genes can be overexpressed or heterologously expressed in transgenic organisms or cells. Other methods for reducing or eliminating expression or activity, e.g., by inducing artificial mutations (e.g., point, deletion, or insertion mutations) in a gene and screening for individuals with the desired loss of expression or activity, or the like, are also well known in the art. See, e.g., the references herein.

Inhibition of expression in cells, organisms, or particular cell types can be used for further studying the in vitro or in vivo role of these genes, as a mechanism for treating a condition caused by overexpression of a wwp-1 or ubc-18 gene, or for treating a dominant effect caused by a particular allele of such a gene. In a particularly useful aspect, expression of wwp-1 and/or ubc-18 is optionally altered (e.g., reduced, silenced, or increased, or altered by expression of a reporter construct) in cells or organisms used for screening for longevity modulators in the present invention.

Antisense, RNAi, and Related Techniques

Use of antisense nucleic acids is well known in the art. An antisense nucleic acid has a region of complementarity to a target nucleic acid, e.g., a target gene, mRNA, or cDNA. Typically, a nucleic acid comprising a nucleotide sequence in a complementary, antisense orientation with respect to a coding (sense) sequence of an endogenous gene is introduced into a cell. The antisense nucleic acid can be RNA, DNA, a PNA or any other appropriate molecule. Antisense oligomers are typically at least about 15 to at least about 50 nucleotides. A duplex forms between the antisense sequence and its complementary sense sequence, resulting in inactivation of the gene. The antisense nucleic acid can inhibit gene expression by forming a duplex with an RNA transcribed from the gene, by forming a triplex with duplex DNA, etc. An antisense nucleic acid can be produced, e.g., for any gene whose coding sequence is known or can be determined by a number of well-established techniques (e.g., chemical synthesis of an antisense RNA or oligonucleotide (optionally including modified nucleotides and/or linkages that increase resistance to degradation or improve cellular uptake) or in vitro transcription). Antisense nucleic acids and their use are described, e.g., in U.S. Pat. No. 6,242,258 to Haselton and Alexander (Jun. 5, 2001) entitled "Methods for the selective regulation of DNA and RNA transcription and translation by photoactivation"; U.S. Pat. Nos. 6,500,615; 6,498,035; 6,395,544; 5,563,050; E. Schuch et al (1991) Symp Soc. Exp Biol 45:117-127; de Lange et al., (1995) Curr Top Microbiol Immunol 197:57-75; Hamilton et al. (1995) Curr Top Microbiol Immunol 197:77-89; Finnegan et al., (1996) Proc Natl Acad Sci USA 93:8449-8454; Uhlmann and A. Pepan (1990), Chem. Rev. 90:543; P. D. Cook (1991), Anti-Cancer Drug Design 6:585; J. Goodchild, Bioconjugate Chem. 1 (1990) 165; and, S. L. Beaucage and R. P. Iyer (1993), Tetrahedron 49:6123; and F. Eckstein, Ed. (1991), *Oligonucleotides and Analogues—A Practical Approach*, IRL Press.

Gene expression can also be inhibited by RNA silencing or interference. "RNA silencing" refers to any mechanism through which the presence of a single-stranded or, typically, a double-stranded RNA in a cell or organism results in inhibition of expression of a target gene comprising a sequence identical or nearly identical to that of the RNA, including, but not limited to, RNA interference, repression of translation of a target mRNA transcribed from the target gene without alteration of the mRNA's stability, and transcriptional silencing (e.g., histone acetylation and heterochromatin formation leading to inhibition of transcription of the target mRNA).

The term "RNA interference" ("RNAi", sometimes called RNA-mediated interference, post-transcriptional gene silencing, or quelling) refers to a phenomenon in which the presence of RNA, typically double-stranded RNA, in a cell or organism results in inhibition of expression of a gene comprising a sequence identical, or nearly identical, to that of the double-stranded RNA. The double-stranded RNA responsible for inducing RNAi is called an "interfering RNA". Expression of the gene is inhibited by the mechanism of RNAi as described below, in which the presence of the interfering RNA results in degradation of mRNA transcribed from the gene and thus in decreased levels of the mRNA and any encoded protein.

The mechanism of RNAi has been and is being extensively investigated in a number of eukaryotic organisms and cell types. See, for example, the following reviews: McManus and Sharp (2002) "Gene silencing in mammals by small interfering RNAs" Nature Reviews Genetics 3:737-747; Hutvagner and Zamore (2002) "RNAi: Nature abhors a double strand" Curr Opin Genet & Dev 200:225-232; Hannon (2002) "RNA interference" Nature 418:244-251; Agami (2002) "RNAi and related mechanisms and their potential use for therapy" Curr Opin Chem Biol 6:829-834; Tuschl and Borkhardt (2002) "Small interfering RNAs: A revolutionary tool for the analysis of gene function and gene therapy" Molecular Interventions 2:158-167; Nishikura (2001) "A short primer on RNAi: RNA-directed RNA polymerase acts as a key catalyst" Cell 107:415-418; and Zamore (2001) "RNA interference: Listening to the sound of silence" Nature Structural Biology 8:746-750. RNAi is also described in the patent literature; see, e.g., CA 2359180 by Kreutzer and Limmer entitled "Method and medicament for inhibiting the expression of a given gene"; WO 01/68836 by Beach et al. entitled "Methods and compositions for RNA interference"; WO 01/70949 by Graham et al. entitled "Genetic silencing"; and WO 01/75164 by Tuschl et al. entitled "RNA sequence-specific mediators of RNA interference".

In brief, double-stranded RNA introduced into a cell (e.g., into the cytoplasm) is processed, for example by an RNAse III-like enzyme called Dicer, into shorter double-stranded fragments called small interfering RNAs (siRNAs, also called short interfering RNAs). The length and nature of the siRNAs produced is dependent on the species of the cell, although typically siRNAs are 21-25 nucleotides long (e.g., an siRNA may have a 19 base pair duplex portion with two nucleotide 3' overhangs at each end). Similar siRNAs can be produced in vitro (e.g., by chemical synthesis or in vitro transcription) and introduced into the cell to induce RNAi. The siRNA becomes associated with an RNA-induced silencing complex (RISC). Separation of the sense and antisense strands of the siRNA, and interaction of the siRNA antisense strand with its target mRNA through complementary base-pairing interactions, optionally occurs. Finally, the mRNA is cleaved and degraded.

Expression of a target gene in a cell can thus be specifically inhibited by introducing an appropriately chosen double-stranded RNA into the cell. Guidelines for design of suitable interfering RNAs are known to those of skill in the art. For example, interfering RNAs are typically designed against exon sequences, rather than introns or untranslated regions. Characteristics of high efficiency interfering RNAs may vary by cell type. For example, although siRNAs may require 3' overhangs and 5' phosphates for most efficient induction of RNAi in *Drosophila* cells, in mammalian cells blunt ended siRNAs and/or RNAs lacking 5' phosphates can induce RNAi as effectively as siRNAs with 3' overhangs and/or 5' phosphates (see, e.g., Czauderna et al. (2003) "Structural variations and stabilizing modifications of synthetic siRNAs in mammalian cells" Nucl Acids Res 31:2705-2716). As another example, since double-stranded RNAs greater than 30-80 base pairs long activate the antiviral interferon response in mammalian cells and result in non-specific silencing, interfering RNAs for use in mammalian cells are typically less than 30 base pairs (for example, Caplen et al. (2001) "Specific inhibition of gene expression by small double-stranded RNAs in invertebrate and vertebrate systems" Proc. Natl. Acad. Sci. USA 98:9742-9747, Elbashir et al. (2001) "Duplexes of 21-nucleotide RNAs mediate RNA interference in cultured mammalian cells" Nature 411:494-498 and Elbashir et al. (2002) "Analysis of gene function in somatic mammalian cells using small interfering RNAs" Methods 26:199-213 describe the use of 21 nucleotide siRNAs to specifically inhibit gene expression in mammalian cell lines, and Kim et al. (2005) "Synthetic dsRNA Dicer substrates enhance RNAi potency and efficacy" Nature Biotechnology 23:222-226 describes use of 25-30 nucleotide duplexes). The sense and antisense strands of a siRNA are typically, but not necessarily, completely complementary to each other over the double-stranded region of the siRNA (excluding any overhangs). The antisense strand is typically completely complementary to the target mRNA over the same region, although some nucleotide substitutions can be tolerated (e.g., a one or two nucleotide mismatch between the antisense strand and the mRNA can still result in RNAi, although at reduced efficiency). The ends of the double-stranded region are typically more tolerant to substitution than the middle; for example, as little as 15 bp (base pairs) of complementarity between the antisense strand and the target mRNA in the context of a 21 mer with a 19 bp double-stranded region has been shown to result in a functional siRNA (see, e.g., Czaudema et al. (2003) "Structural variations and stabilizing modifications of synthetic siRNAs in mammalian cells" Nucl Acids Res 31:2705-2716). Any overhangs can but need not be complementary to the target mRNA; for example, TT (two 2'-deoxythymidines) overhangs are frequently used to reduce synthesis costs.

Although double-stranded RNAs (e.g., double-stranded siRNAs) were initially thought to be required to initiate RNAi, several recent reports indicate that the antisense strand of such siRNAs is sufficient to initiate RNAi. Single-stranded antisense siRNAs can initiate RNAi through the same pathway as double-stranded siRNAs (as evidenced, for example, by the appearance of specific mRNA endonucleolytic cleavage fragments). As for double-stranded interfering RNAs, characteristics of high-efficiency single-stranded siRNAs may vary by cell type (e.g., a 5' phosphate may be required on the antisense strand for efficient induction of RNAi in some cell types, while a free 5' hydroxyl is sufficient in other cell types capable of phosphorylating the hydroxyl). See, e.g., Martinez et al. (2002) "Single-stranded antisense siRNAs guide target RNA cleavage in RNAi" Cell 110:563-574; Amarzguioui et al. (2003) "Tolerance for mutations and chemical modifications in a siRNA" Nucl. Acids Res. 31:589-595; Holen et al. (2003) "Similar behavior of single-strand and double-strand siRNAs suggests that they act through a common RNAi pathway" Nucl. Acids Res. 31:2401-2407; and Schwarz et al. (2002) Mol. Cell. 10:537-548.

Due to currently unexplained differences in efficiency between siRNAs corresponding to different regions of a given target mRNA, several siRNAs are typically designed and tested against the target mRNA to determine which siRNA is most effective. Interfering RNAs can also be produced as small hairpin RNAs (shRNAs, also called short hairpin RNAs), which are processed in the cell into siRNA-like molecules that initiate RNAi (see, e.g., Siolas et al. (2005) "Synthetic shRNAs as potent RNAi triggers" Nature Biotechnology 23:227-231). Such hairpins can be encoded by genes introduced into the cell or organism, optionally under the control of inducible or other desired promoters.

Further details on RNAi and induction thereof are available in the art; see, e.g., references herein. For construction of transgenic Drosophila in which RNAi of a given gene is inducible and/or heritable, for example, see also Takemae et al. (2003) "Proteoglycan UDP-Galactose:β-Xylose β1,4-Galactosyltransferase I Is Essential for Viability in Drosophila melanogaster" J. Biol. Chem. 278:15571-15578, Kamiyama et al. (2003) "Molecular Cloning and Identification of 3'-Phosphoadenosine 5'-Phosphosulfate Transporter" J. Biol. Chem. 278:25958-25963, Ichimiya et al. (2004) "The Twisted Abdomen Phenotype of Drosophila POMT1 and POMT2 Mutants Coincides with Their Heterophilic Protein O-Mannosyltransferase Activity" J. Biol. Chem. 279:42638-42647, and Kwon et al. (2003) "The Drosophila Selenoprotein BthD Is Required for Survival and Has a Role in Salivary Gland Development" Mol Cell Biol. 23:8495-8504.

See, e.g., the Examples section below for an example of RNAi in C. elegans, as well as for references describing useful libraries of RNAi constructs.

The presence of RNA, particularly double-stranded RNA, in a cell can result in inhibition of expression of a gene comprising a sequence identical or nearly identical to that of the RNA through mechanisms other than RNAi. For example, double-stranded RNAs that are partially complementary to a target mRNA can repress translation of the mRNA without affecting its stability. As another example, double-stranded RNAs can induce histone methylation and heterochromatin formation, leading to transcriptional silencing of a gene comprising a sequence identical or nearly identical to that of the RNA (see, e.g., Schramke and Allshire (2003) "Hairpin RNAs and retrotransposon LTRs effect RNAi and chromatin-based gene silencing" Science 301:1069-1074; Kawasaki and Taira (2004) "Induction of DNA methylation and gene silencing by short interfering RNAs in human cells" Nature 431: 211-217; and Morris et al. (2004) "Small interfering RNA-induced transcriptional gene silencing in human cells" Science 305:1289-1292).

Short RNAs called microRNAs (miRNAs) have been identified in a variety of species. Typically, these endogenous RNAs are each transcribed as a long RNA and then processed to a pre-miRNA of approximately 60-75 nucleotides that forms an imperfect hairpin (stem-loop) structure. The pre-miRNA is typically then cleaved, e.g., by Dicer, to form the mature miRNA. Mature miRNAs are typically approximately 21-25 nucleotides in length, but can vary, e.g., from about 14 to about 25 or more nucleotides. Some, though not all, miRNAs have been shown to inhibit translation of mRNAs bearing partially complementary sequences. Such miRNAs contain one or more internal mismatches to the corresponding mRNA that are predicted to result in a bulge in the center of the duplex formed by the binding of the miRNA antisense strand to the mRNA. The miRNA typically forms approximately 14-17 Watson-Crick base pairs with the mRNA; additional wobble base pairs can also be formed. In addition, short synthetic double-stranded RNAs (e.g., similar to siRNAs) containing central mismatches to the corresponding mRNA have been shown to repress translation (but not initiate degradation) of the mRNA. See, for example, Zeng et al. (2003) "MicroRNAs and small interfering RNAs can inhibit mRNA expression by similar mechanisms" Proc. Natl. Acad. Sci. USA 100:9779-9784; Doench et al. (2003) "siRNAs can function as miRNAs" Genes & Dev. 17:438-442; Bartel and Bartel (2003) "MicroRNAs: At the root of plant development?" Plant Physiology 132:709-717; Schwarz and Zamore (2002) "Why do miRNAs live in the miRNP?" Genes & Dev. 16:1025-1031; Tang et al. (2003) "A biochemical framework for RNA silencing in plants" Genes & Dev. 17:49-63; Meister et al. (2004) "Sequence-specific inhibition of microRNA- and siRNA-induced RNA silencing" RNA 10:544-550; Nelson et al. (2003) "The microRNA world: Small is mighty" Trends Biochem. Sci. 28:534-540; Scacheri et al. (2004) "Short interfering RNAs can induce unexpected and divergent changes in the levels of untargeted proteins in mammalian cells" Proc. Natl. Acad. Sci. USA 101:1892-1897; Sempere et al. (2004) "Expression profiling of mammalian microRNAs uncovers a subset of brain-expressed microRNAs with possible roles in murine and human neuronal differentiation" Genome Biology 5:R13; Dykxhoorn et al. (2003) "Killing the messenger: Short RNAs that silence gene expression" Nature Reviews Molec. and Cell Biol. 4:457-467; McManus (2003) "MicroRNAs and cancer" Semin Cancer Biol. 13:253-288; and Stark et al. (2003) "Identification of Drosophila microRNA targets" PLoS Biol. 1:E60.

The cellular machinery involved in translational repression of mRNAs by partially complementary RNAs (e.g., certain miRNAs) appears to partially overlap that involved in RNAi, although, as noted, translation of the mRNAs, not their stability, is affected and the mRNAs are typically not degraded.

The location and/or size of the bulge(s) formed when the antisense strand of the RNA binds the mRNA can affect the ability of the RNA to repress translation of the mRNA. Similarly, location and/or size of any bulges within the RNA itself can also affect efficiency of translational repression. See, e.g., the references above. Typically, translational repression is most effective when the antisense strand of the RNA is complementary to the 3' untranslated region (3' UTR) of the mRNA. Multiple repeats, e.g., tandem repeats, of the sequence complementary to the antisense strand of the RNA can also provide more effective translational repression; for example, some mRNAs that are translationally repressed by endogenous miRNAs contain 7-8 repeats of the miRNA binding sequence at their 3' UTRs. It is worth noting that translational repression appears to be more dependent on concentration of the RNA than RNA interference does; translational repression is thought to involve binding of a single mRNA by each repressing RNA, while RNAi is thought to involve cleavage of multiple copies of the mRNA by a single siRNA-RISC complex.

Guidance for design of a suitable RNA to repress translation of a given target mRNA can be found in the literature (e.g., the references above and Doench and Sharp (2004) "Specificity of microRNA target selection in translational repression" Genes & Dev. 18:504-511; Rehmsmeier et al. (2004) "Fast and effective prediction of microRNA/target duplexes" RNA 10:1507-1517; Robins et al. (2005) "Incorporating structure to predict microRNA targets" Proc Natl Acad Sci 102:4006-4009; and Mattick and Makunin (2005) "Small regulatory RNAs in mammals" Hum. Mol. Genet. 14:R121-R132, among many others) and herein. However, due to differences in efficiency of translational repression between RNAs of different structure (e.g., bulge size, sequence, and/or location) and RNAs corresponding to different regions of the target mRNA, several RNAs are optionally designed and tested against the target mRNA to determine which is most effective at repressing translation of the target mRNA.

Knockout and Transgenic Animals

Transgenic animals related to or of use in the methods and systems of the invention are also featured. Accordingly, one general class of embodiments provides a transgenic non-human animal comprising a knock out or knock down mutation in wwp-1 and/or ubc-18, overexpressing wwp-1 and/or ubc-18, or a recombinant reporter construct (e.g., a wwp-1 or ubc-18 GFP fusion protein or promoter-reporter construct) in the genome of the animal. The recombinant gene is optionally under control of an endogenous promoter, a heterologous promoter and/or an inducible promoter (e.g., a heat shock promoter), and is optionally from the same and/or a different species. Exemplary non-human animals have been described above.

Methods of making transgenic animals that have knock out or knock down mutations and/or that express heterologous genes are well known in the art. In general, such a transgenic animal is typically one that has had appropriate genes (or partial or recombinant genes, e.g., comprising coding sequences coupled to a promoter) introduced into one or more of its cells artificially. For example, a DNA can be integrated randomly, e.g., by injecting it into the pronucleus of a fertilized ovum such that the DNA can integrate anywhere in the genome without need for homology between the injected DNA and the host genome. P-element mediated transduction in *Drosophila* provides one such classical and well understood system. As another example, targeted insertion can be accomplished, e.g., by introducing the heterologous DNA, e.g., into embryonic stem (ES) cells, and selecting for cells in which the heterologous DNA has undergone homologous recombination with homologous sequences of the cellular genome. This is common particularly in non-human mammalian transgenic systems, e.g., in making transgenic rodents such as transgenic mice.

As noted, one common use of targeted insertion of DNA is to make knock-out mice. These are useful in the present invention in a variety of contexts, e.g., as targets for modulator studies. Similarly, transgenic animals that comprise deletions of natural wwp-1, ubc-18, or other dietary restriction pathway genes can also include targeted insertion of corresponding human genes. This provides an improved model system that is more highly correlated with the human pathway.

In these approaches, typically, homologous recombination is used to insert a selectable gene (e.g., an antibiotic resistance gene or another positive selectable marker) driven by a constitutive promoter into an essential exon of the gene that one wishes to disrupt (e.g., the first coding exon). To accomplish this, the selectable marker is flanked by large stretches of DNA that match the genomic sequences surrounding the desired insertion point (typically, there are several kilobases of homology between the heterologous and genomic DNA). Once this construct is electroporated into ES cells, the cells' own machinery performs the homologous recombination. To make it possible to select against ES cells that incorporate DNA by non-homologous recombination (e.g., random insertion), it is common for targeting constructs to include a negatively selectable gene outside the region intended to undergo recombination (typically the gene is cloned adjacent to the shorter of the two regions of genomic homology). Because DNA lying outside the regions of genomic homology is lost during homologous recombination, cells undergoing homologous recombination cannot be selected against, whereas cells undergoing random integration of DNA often can. A commonly used gene for negative selection is the herpes virus thymidine kinase gene, which confers sensitivity to the drug gancyclovir.

Following positive selection and negative selection if desired, ES cell clones are screened for incorporation of the construct into the correct genomic locus. Typically, one designs a targeting construct so that a band normally seen on a Southern blot or following PCR amplification becomes replaced by a band of a predicted size when homologous recombination occurs. Since ES cells are diploid, only one allele is usually altered by the recombination event so, when appropriate targeting has occurred, one usually sees bands representing both wild type and targeted alleles.

The embryonic stem (ES) cells that are used for targeted insertion are derived from the inner cell masses of blastocysts (early mouse embryos). These cells are pluripotent, meaning they can develop into any type of tissue.

Once positive ES clones have been grown up and frozen, the production of transgenic animals can begin. Donor females are mated, blastocysts are harvested, and several ES cells are injected into each blastocyst. Blastocysts are then implanted into a uterine horn of each recipient. By choosing an appropriate donor strain, the detection of chimeric offspring (i.e., those in which some fraction of tissue is derived from the transgenic ES cells) can be as simple as observing hair and/or eye color. If the transgenic ES cells do not contribute to the germline (sperm or eggs), the transgene cannot be passed on to offspring. It will be evident that analogous techniques can be used to introduce essentially any heterologous gene of interest, instead of or in addition to knocking out an endogenous gene in the mouse.

Methods for making transgenic insects, particularly *Drosophila melanogaster*, have also been described. For example, use of P elements to make transgenic flies is well known in the art. P elements can be used, e.g., to knock out or knock down expression of an endogenous gene and/or to introduce a heterologous gene. Typically, the gene of interest is placed between P element ends, usually within a plasmid, and injected into pre-blastoderm embryos in the presence of transposase. The P element then transposes from the plasmid to a random chromosomal site, carrying the gene with it. The P element typically also carries a second gene for convenient identification of transformants. A visible marker such as an eye color gene is generally preferred, although other markers can be employed, e.g., a selectable marker such as neomycin resistance. The transposase can be provided, for example, by binding a purified transposase protein to the element prior to injection, by coinjecting a transposase-encoding helper plasmid, or most typically by injecting directly into embryos that have an endogenous transposase. The transposase-bearing chromosome can be marked with a dominant mutation, such that stable transformants lacking the transposase gene can be selected among the progeny.

A variety of P element vectors are available in the art, including vectors to facilitate expression of the gene of interest in particular tissues, at particular times in development, or upon induction by elevated temperature, for example. Additional vectors can readily be constructed or modified as needed. Available vectors include those encoding the FLP site-specific recombinase and bearing its target site FRT, which can be used to generate somatic mosaics by site-specific recombination. P element mediated transformation can also be employed to achieve gene replacement by making use of P-induced double strand breaks. In addition, a P element can be mobilized such that insertion occurs at a large number of random sites. Progeny bearing such insertions are then screened to identify lines in which the element is inserted within a desired gene, e.g., to reduce or eliminate expression of the gene.

Similar techniques enable construction of transgenic animals of other species. Additional details are available in the art. See, e.g., Ashbumer et al. (2004) *Drosophila: A Laboratory Handbook* 2nd edition Cold Spring Harbor Laboratory Press, Greenspan (2004) *Fly Pushing: The Theory and Practice of Drosophila Genetics*, $2^{nd}$ edition Cold Spring Harbor Laboratory Press, Sullivan et al. (eds) (2000) *Drosophila Protocols* Cold Spring Harbor Laboratory Press, Roberts (ed) (1998) *Drosophila: A Practical Approach* Oxford University Press, USA, Schepers (2005) *RNA Interference in Practice: Principles, Basics, and Methods for Gene Silencing in C. elegans. Drosophila, and Mammals* Wiley-VCH, Nagy et al. (eds) (2002) *Manipulating the Mouse Embryo: A Laboratory Manual*, 3rd edition Cold Spring Harbor Laboratory Press, Tymms and Kola (eds) (2001) *Gene Knockout Protocols* (Methods in Molecular Biology) Humana Press, Hofker and van Deursen (eds) (2002) *Transgenic Mouse Methods and Protocols* (Methods in Molecular Biology) Humana Press, Hope (ed) (2002) *C. elegans: A Practical Approach* (Practical Approach Series) Oxford University Press, USA, and Strange (ed) (2006) *C. elegans: Methods and Applications* (Methods in Molecular Biology) Humana Press. See also the Examples section herein.

As with the murine system described above, human genes in the relevant pathway, e.g., wwp-1, ubc-18, or other genes in the dietary restriction pathway, can be introduced into *C. elegans* or *Drosophila* (or any other model organism) to more accurately screen for modulators of the human genes, and to study human gene function.

Transgenic animals are a useful tool for studying gene function and testing modulators or potential modulators. For example, a variety of transgenic animals useful in the screening systems and methods of the present invention have been described in detail above. As an additional example, human (or other selected) homolog genes can be introduced in place of the endogenous wwp-1, ubc-18, and/or other related genes of a laboratory animal, making it possible to study function of the human (or other) polypeptide or complex in the easily manipulated and studied laboratory animal. It will be appreciated that there is not always precise correspondence between protein structure or function of different animals, making the ability to study the human or other gene of interest particularly useful when developing clinical candidate modulators. Although similar genetic manipulations can be performed in tissue culture, the interaction of wwp-1, ubc-18, and other genes in the pathway in the context of an intact organism can provide a more complete and physiologically relevant picture of function than could be achieved in non-cell based assays or simple cell-based screening assays. Accordingly, transgenic animals are particularly useful when analyzing modulators identified in high throughput in vitro (e.g., cell-free and/or cell-based) systems. As another advantage, in higher organisms with at least two wwp-1 homolog genes, such as humans, compounds that selectively induce or inhibit the activity or expression of one wwp-1 protein and not another may be identified in assays using pairs of such transgenic animals (or, similarly, pairs of transgenic cell lines in cell-based assays) each only expressing one wwp-1 homolog gene and comparing the effect of the compound on each organism (or cell line).

Sequence Comparison, Identity, and Homology

Of particular interest in the present invention are nucleic acids that encode a protein component of the pathway that mediates dietary restriction induced longevity (e.g., wwp-1 and ubc-18), genes that regulate the pathway, and polypeptides that are components of or that regulate the pathway. As noted above, such genes, nucleic acids, and proteins of interest include those from *C. elegans* as well as homologs and orthologs thereof. Sequences substantially identical to the nucleotide or amino acid sequences thereof are also of interest in the present invention.

The terms "identical" or "percent identity", in the context of two or more nucleic acid or polypeptide sequences, refer to two or more sequences or subsequences that are the same or have a specified percentage of amino acid residues or nucleotides that are the same, when compared and aligned for maximum correspondence, as measured using one of the sequence comparison algorithms described below (or other algorithms available to persons of skill) or by visual inspection.

The phrase "substantially identical", in the context of two nucleic acids or polypeptides (e.g., DNAs encoding a dietary restriction pathway component, or domain thereof, or the amino acid sequence of a dietary restriction pathway component, or domain thereof) refers to two or more sequences or subsequences that have at least about 60%, about 80%, about 90, about 95%, about 98%, or about 99% or more nucleotide or amino acid residue identity, when compared and aligned for maximum correspondence, as measured using a sequence comparison algorithm or by visual inspection. Such "substantially identical" sequences are typically considered to be "homologous", without reference to actual ancestry. Preferably, the "substantial identity" exists over a region of the sequences that is at least about 50 residues in length, more preferably over a region of at least about 100 residues, and most preferably, the sequences are substantially identical over at least about 150 residues, at least about 250 residues, or over the full length of the two sequences to be compared.

Proteins and/or protein sequences are "homologous" when they are derived, naturally or artificially, from a common ancestral protein or protein sequence. Similarly, nucleic acids and/or nucleic acid sequences are homologous when they are derived, naturally or artificially, from a common ancestral nucleic acid or nucleic acid sequence. Homology is generally inferred from sequence similarity between two or more nucleic acids or proteins (or sequences thereof). The precise percentage of similarity between sequences that is useful in establishing homology varies with the nucleic acid and protein at issue, but as little as 25% sequence similarity (e.g., identity) over 50, 100, 150 or more residues (nucleotides or amino acids) is routinely used to establish homology (e.g., over the full length of the two sequences to be compared). Higher levels of sequence similarity (e.g., identity), e.g., 30%, 40%, 50%, 60%, 70%, 80%, 90%, 95%, or 99% or more, can also be used to establish homology. Methods for determining sequence similarity percentages (e.g., BLASTP and BLASTN using default parameters) are described herein and are generally available. Genes (or proteins) that are homologous are referred to as homologs. Optionally, homologous proteins demonstrate comparable activities (e.g., ubiquitin ligase activity, ubiquitin conjugating activity, or similar). "Orthologs" are genes in different species that evolved from a common ancestral gene by speciation. Normally, orthologs retain the same or similar function in the course of evolution. As used herein "orthologs" are included in the term "homologs".

For sequence comparison and homology determination, typically one sequence acts as a reference sequence to which test sequences are compared. When using a sequence comparison algorithm, test and reference sequences are input into a computer, subsequence coordinates are designated, if necessary, and sequence algorithm program parameters are designated. The sequence comparison algorithm then calculates the percent sequence identity for the test sequence(s) relative to the reference sequence, based on the designated program parameters. A typical reference sequence of the invention is optionally a nucleic acid or amino acid sequence corresponding to wwp-1 or ubc-18.

Optimal alignment of sequences for comparison can be conducted, e.g., by the local homology algorithm of Smith & Waterman, Adv. Appl. Math. 2:482 (1981), by the homology alignment algorithm of Needleman & Wunsch, J. Mol. Biol. 48:443 (1970), by the search for similarity method of Pearson & Lipman, Proc. Nat'l. Acad. Sci. USA 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by visual inspection (see generally Ausubel).

One example of an algorithm that is suitable for determining percent sequence identity and sequence similarity is the BLAST algorithm, which is described in Altschul et al., J. Mol. Biol. 215:403-410 (1990). Software for performing BLAST analyses is publicly available through the National Center for Biotechnology Information. This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always>0) and N (penalty score for mismatching residues; always<0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, a cutoff of 100, M=5, N=−4, and a comparison of both strands. For amino acid sequences, the BLASTP program uses as defaults a wordlength (W) of 3, an expectation (E) of 10, and the BLOSUM62 scoring matrix (see Henikoff & Henikoff (1989) Proc. Natl. Acad. Sci. USA 89:10915).

In addition to calculating percent sequence identity, the BLAST algorithm also performs a statistical analysis of the similarity between two sequences (see, e.g., Karlin & Altschul, Proc. Natl. Acad. Sci. USA 90:5873-5787 (1993)). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.1, more preferably less than about 0.01, and most preferably less than about 0.001. The above-described techniques are useful in identifying homologous sequences for use in the methods described herein.

Antibodies

Antibodies to wwp-1 and/or ubc-18 polypeptides (or complexes thereof), substrates of wwp-1, etc. can be generated using methods that are well known. The antibodies can be utilized for detecting and/or purifying polypeptides or complexes of interest. Antibodies can optionally discriminate the polypeptides from homologs, discriminate post-translationally modified forms from unmodified forms (or other post-translationally modified forms), and/or can be used in biosensor applications. Antibodies can also be used to block or enhance function of the polypeptides and complexes, in vivo, in situ or in vitro. Thus, antibodies to wwp-1 and/or ubc-18 and or a complex thereof can be used as therapeutic reagents. As used herein, the term antibody includes, but is not limited to, polyclonal antibodies, monoclonal antibodies, humanized or chimeric antibodies and biologically functional antibody fragments, which are those fragments sufficient for binding of the antibody fragment to the protein.

For the production of antibodies to a polypeptide encoded by a sequence of interest, e.g., wwp-1 or ubc-18 or a conservative variant or fragment thereof, various host animals may be immunized by injection with the polypeptide or a portion thereof. Such host animals may include, but are not limited to, rabbits, mice and rats, and the like. Various adjuvants may be used to enhance the immunological response, depending on the host species, including, but not limited to, Freund's (complete and incomplete), mineral gels such as aluminum hydroxide, surface active substances such as lysolecithin, pluronic polyols, polyanions, peptides, oil emulsions, keyhole limpet hemocyanin, dinitrophenol, and potentially useful human adjuvants such as BCG (Bacille Calmette-Guerin) and *Corynebacterium parvum*.

Polyclonal antibodies are heterogeneous populations of antibody molecules derived from the sera of animals immunized with an antigen, such as target gene product, or an antigenic functional derivative thereof. For the production of polyclonal antibodies, host animals, such as those described above, may be immunized by injection with the encoded protein, or a portion thereof, supplemented with adjuvants as also described above.

Monoclonal antibodies (mAbs), which are homogeneous populations of antibodies to a particular antigen, may be obtained by any technique that provides for the production of antibody molecules by continuous cell lines in culture. These include, but are not limited to, the hybridoma technique of Kohler and Milstein (*Nature* 256:495-497, 1975; and U.S. Pat. No. 4,376,110), the human B-cell hybridoma technique (Kosbor et al., *Immunology Today* 4:72, 1983; Cole et al., *Proc. Nat'l. Acad. Sci. USA* 80:2026-2030, 1983), and the EBV-hybridoma technique (Cole et al., *Monoclonal Antibodies and Cancer Therapy*, Alan R. Liss, Inc., pp. 77-96, 1985). Such antibodies may be of any immunoglobulin class, including IgG, IgM, IgE, IgA, IgD, and any subclass thereof. The hybridoma producing the mAb of this invention may be cultivated in vitro or in vivo. Production of high titers of mAbs in vivo makes this the presently preferred method of production.

In addition, techniques developed for the production of "chimeric antibodies" (Morrison et al., *Proc. Nat'l. Acad. Sci. USA* 81:6851-6855, 1984; Neuberger et al., *Nature* 312:604-608, 1984; Takeda et al., *Nature* 314:452-454, 1985) by splicing the genes from a mouse antibody molecule of appropriate antigen specificity together with genes from a human antibody molecule of appropriate biological activity can be used. A chimeric antibody is a molecule in which different portions are derived from different animal species, such as those having a variable or hypervariable region derived from a murine mAb and a human immunoglobulin constant region.

Alternatively, techniques described for the production of single-chain antibodies (U.S. Pat. No. 4,946,778; Bird, *Science* 242:423-426, 1988; Huston et al., *Proc. Nat'l. Acad. Sci. USA* 85:5879-5883, 1988; and Ward et al., *Nature* 334:544-546, 1989) can be adapted to produce differentially expressed gene-single chain antibodies. Single chain antibodies are formed by linking the heavy and light chain fragments of the Fv region via an amino acid bridge, resulting in a single-chain polypeptide.

Antibody fragments which recognize specific epitopes may be generated by known techniques. For example, such fragments include, but are not limited to, the $F(ab')_2$ fragments, which can be produced by pepsin digestion of the antibody molecule, and the Fab fragments, which can be generated by reducing the disulfide bridges of the $F(ab')_2$ fragments. Alternatively, Fab expression libraries may be constructed (Huse et al., Science 246:1275-1281, 1989) to allow rapid and easy identification of monoclonal Fab fragments with the desired specificity.

In addition, antibodies (e.g., for detection of protein expression or detection of post-translational modification levels) can typically be custom ordered from any of a variety of sources, such as PeptidoGenic (pkim (dot) ccnet (dot) corn), HTI Bio-products, Inc. (www (dot) htibio (dot) corn), BMA Biomedicals Ltd (U.K.), Bio. Synthesis, Inc., Research Genetics (Huntsville, Ala.) and many others.

Protocols for detecting and measuring expression of the described polypeptides herein using the above mentioned antibodies are well known in the art. Such methods include, but are not limited to, dot blotting, western blotting, competitive and noncompetitive protein binding assays, enzyme-linked immunosorbant assays (ELISA), immunohistochemistry, fluorescence-activated cell sorting (FACS), and others commonly used and widely described in scientific and patent literature, and many employed commercially.

One method which can be employed for ease of detection is the sandwich ELISA, of which a number of variations exist, all of which are intended to be encompassed by the present invention. For example, in a typical forward assay, unlabeled antibody is immobilized on a solid substrate and the sample to be tested is brought into contact with the bound molecule and incubated for a period of time sufficient to allow formation of an antibody-antigen binary complex. At this point, a second antibody, labeled with a reporter molecule capable of inducing a detectable signal, is then added and incubated, allowing time sufficient for the formation of a ternary complex of antibody-antigen-labeled antibody. Any unreacted material is washed away, and the presence of the antigen, e.g., a wwp-1 or ubc-18 polypeptide, a ubiquitinated wwp-1 substrate, etc., is determined by observation of a signal or optionally quantitated by comparing with a control sample containing known amounts of antigen. Variations on the forward assay include the simultaneous assay, in which both sample and antibody are added simultaneously to the bound antibody, or a reverse assay, in which the labeled antibody and sample to be tested are first combined, incubated and added to the unlabeled surface bound antibody. These techniques are well known to those skilled in the art, and the possibility of minor variations will be readily apparent. As used herein, "sandwich assay" is intended to encompass all variations on the basic two-site technique. For the immunoassays of the present invention, the only limiting factor is that the labeled antibody be an antibody that is specific for the protein expressed by the gene of interest, the particular post-translationally modified form of interest, or the like.

The most commonly used reporter molecules in this type of assay are enzymes and fluorophore- or radionuclide-containing molecules. In the case of an enzyme immunoassay, an enzyme is conjugated to the second antibody, usually by means of glutaraldehyde or periodate. As will be readily recognized, however, a wide variety of different ligation techniques exist which are well-known to the skilled artisan. Commonly used enzymes include horseradish peroxidase, glucose oxidase, beta-galactosidase and alkaline phosphatase, among others. The substrates to be used with the specific enzymes are generally chosen for the production, upon hydrolysis by the corresponding enzyme, of a detectable color change. For example, p-nitrophenyl phosphate is suitable for use with alkaline phosphatase conjugates; for peroxidase conjugates, 1,2-phenylenediamine or toluidine are commonly used. It is also possible to employ fluorogenic substrates, which yield a fluorescent product, or chemiluminescent substrates rather than the chromogenic substrates noted above. A solution containing the appropriate substrate is then added to the tertiary complex. The substrate reacts with the enzyme linked to the second antibody, giving a qualitative visual signal, which may be further quantitated, usually spectrophotometrically, to give an evaluation of the amount of antigen present in a sample.

Alternately, fluorescent compounds, such as fluorescein and rhodamine, can be chemically coupled to antibodies without altering their binding capacity. When activated by illumination with light of a particular wavelength, the fluorochrome-labeled antibody absorbs the light energy, inducing a state of excitability in the molecule, followed by emission of the light at a characteristic longer wavelength. The emission appears as a characteristic color visually detectable with a light microscope. Immunofluorescence and EIA techniques are both very well established in the art and are particularly preferred for the present method. However, other reporter molecules, such as radioisotopes, chemiluminescent or bioluminescent molecules may also be employed. It will be readily apparent to the skilled artisan how to vary the procedure to suit the required use.

Antibodies specific for wwp-1 and/or ubc-18 are useful in modulating (e.g., increasing) lifespan, as well as in targeting cells that express wwp-1 and/or ubc-18. In human therapeutic applications of such antibodies, e.g., where an increase in longevity is desired, including any of those applications noted herein, antibodies will normally be humanized before use. Thus, antibodies to wwp-1 and/or ubc-18 can be generated by any available method as noted above and subsequently humanized appropriately for use in vivo in humans. Many methods of humanizing antibodies are currently available, including those described in Howard and Kaser *Making and Using Antibodies: A Practical Handbook* ISBN: 0849335280

(2006). In typical approaches, humanized Abs are created by combining, at the genetic level, the complementarity-determining regions of a murine (or other mammalian) mAb with the framework sequences of a human Ab variable domain. This leads to a functional Ab with reduced immunogenic side effects in human therapy. Such techniques are generally described in U.S. Pat. Nos. 5,932,448; 5,693,762; 5,693,761; 5,585,089; 5,530,101; 5,569,825; 5,625,126; 5,633,425; 5,789,650; 5,661,016; and 5,770,429. Methods of making "superhumanized" antibodies with still further reduced immunogenicity in humans are described in Tan et al. (2002) ""Superhumanized" Antibodies: Reduction of Immunogenic Potential by Complementarity-Determining Region Grafting with Human Germline Sequences: Application to an Anti-CD28" The Journal of Immunology, 169:1119-1125. Any available humanization method can be applied to making humanized antibodies of the present invention.

EXAMPLES

It is understood that the examples and embodiments described herein are for illustrative purposes only and that various modifications or changes in light thereof will be suggested to persons skilled in the art and are to be included within the spirit and purview of this application and scope of the appended claims. Accordingly, the following examples are offered to illustrate, but not to limit, the claimed invention.

Example 1

The HECT E3 Ligase WWP-1 and the E2 UBC-18 Regulate Longevity Via Dietary Restriction in *C. elegans*

When diet is restricted (Dietary Restriction or DR), lifespan is extended in diverse species suggesting that there is a conserved mechanism for nutrient regulation of aging. How DR life extension occurs has not previously been clear. We present results herein that uncover a role for the HECT E3 ubiquitin ligase WWP-1 as a lifespan regulator in *C. elegans*. We find that overexpression of wwp-1 in worms can extend their lifespan by 20%. Our studies identify wwp-1 as an essential regulator of DR-induced longevity. Reduction of WWP-1 levels by dsRNA (double-stranded RNA) treatment completely suppressed the extended longevity of eat-2 mutant animals. In addition, the lifespan of wwp-1 mutant animals grown under true DR conditions was not extended. Overexpression of a mutant form of WWP-1, lacking catalytic activity as a result of mutation of the conserved catalytic cysteine in the HECT domain, suppressed eat-2 mutant increased lifespan indicating that ubiquitin ligase activity is essential for longevity. Additionally, we show the E2 ubiquitin conjugating enzyme UBC-18 is also essential for DR induced longevity. Our results show that WWP-1 and UBC-18 function together to ubiquitinate substrates that regulate DR induced longevity.

Protein ubiquitination is required for diverse biological processes and is carried out by a defined enzymatic cascade which consists of the actions of an E1 (ubiquitin activating enzyme), E2 (ubiquitin conjugating enzyme), and E3 (ubiquitin ligase) (reviewed in[1,2]) The E3s determine specificity of substrate recognition via protein-protein interactions. HECT (homologous to E6AP C-terminus) E3 ligases promote the ubiquitination of proteins that are essential in a variety of cellular events (see, e.g.,[59]). HECT domains are structurally similar to E2s and possess an active site cysteine residue that transfers the activated ubiquitin from the E2 to itself and then to a lysine on its target protein[3,4]. A family of WW domain HECT ligases consisting of the mammalian WWP1, WWP2 and Itch were initially identified in a search for novel proteins containing WW domains, which are modular protein interaction domains that can recognize short proline motifs in their partners[5]. WWP ligases generally contain an N-terminal C2 domain, which is a phospholipid membrane interaction motif, in addition to their four WW domains. To identify cellular pathways in which WWP E3 ligases are involved we have taken advantage of *C. elegans* as a model organism, which is not only genetically tractable, but also has only a single wwp ortholog, wwp-1 (Y65B4BR.4). Disruption of wwp-1 using RNA interference (RNAi) yields an embryonic lethal phenotype. This lethality occurs late in embryogenesis, and is characterized by abnormal embryogenesis despite normal cell proliferation early in embryogenesis[6]. The embryonic lethal phenotype of wwp-1 RNAi indicates an essential developmental function, but we were interested in elucidating additional functions wwp-1 may have in the adult worm.

Approximately 15% of *C. elegans* genes are encoded in operons. Operons contain co-transcribed genes that make a polycistronic pre-mRNA that are subsequently separated into single-gene mRNA by trans-splicing (reviewed in[7]). wwp-1 has been predicted to be organized in an operon downstream of two uncharacterized genes y65b4br. 5 and y65b4br.8[8]. wwp-1 contains a putative SL2 site, an internal trans-splice site found in polycistronic pre-mRNAs, upstream of its coding region. To determine if dsRNA against wwp-1 specifically interferes with its expression and not with the other genes in the putative operon, we performed RT-PCR using specific primers for each gene. Worms fed wwp-1 dsRNA had significant loss of wwp-1 mRNA expression but not y65b4br.5 or y65b4br. 8 mRNA expression even after dsRNA treatment over multiple generations (FIG. 5 Panel B). We find that mutant allele wwp-1(ok1102) has a partially penetrant embryonic lethal phenotype. To confirm the results obtained using wwp-1 dsRNA, we have performed parallel experiments with wwp-1 null worms (ok1102) that survive to adulthood (FIG. 5 Panel A).

To elucidate the tissue distribution to which WWP-1 localizes in *C. elegans*, we generated a gfp-tagged wwp-1 cDNA construct under the control of the endogenous wwp-1 promoter, which expresses an N-terminal GFP-WWP-1 fusion protein, and created stable transgenic lines (see materials and methods). We observed GFP fluorescence in the cytoplasm of several neurons localized in the head and tail and the ventral nerve chord (FIG. 6 Panels A-F). The GFP signal was reduced upon treatment with wwp-1 dsRNA (FIG. 7 Panels A-D), confirming that WWP-1 was specifically expressed and that our wwp-1 RNAi construct targeted wwp-1. The cell type specific expression of GFP indicates that wwp-1 can be transcriptionally regulated by a promoter immediately upstream of its coding region. Recently wwp-1 was identified in a RNAi screen for genes required for synapse structure and function[9]. This along with our localization results suggests that WWP-1 functions in neurons in *C. elegans*.

Figure 8A:
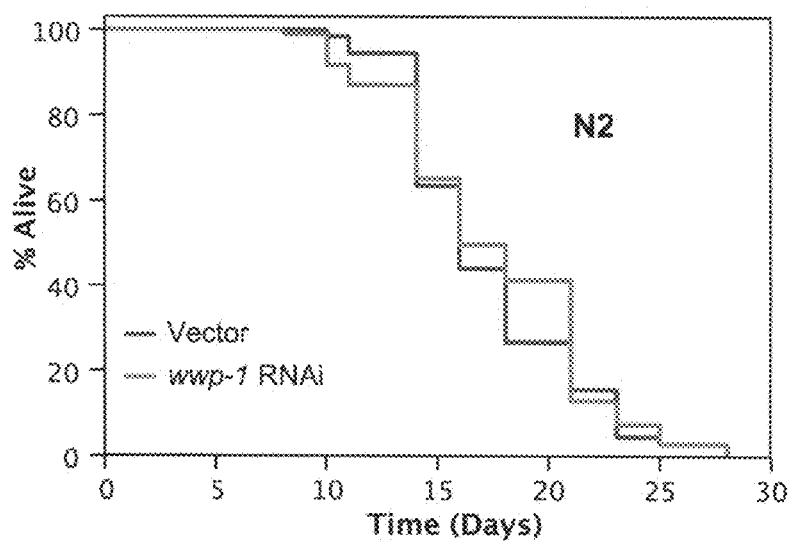
FIG. 8 Panels A-C present line graphs showing that loss of wwp-1 or ubc-18 has no affect on lifespan at 20° C. Lifespan analysis of N2 worms fed wwp-1 RNAi or control vector (Panel A), wwp-1(ok1102) mutant worms (Panel B), and N2 worms fed ubc-18 RNAi or control vector (Panel C) at 20° C. is shown.
Figure 8B:
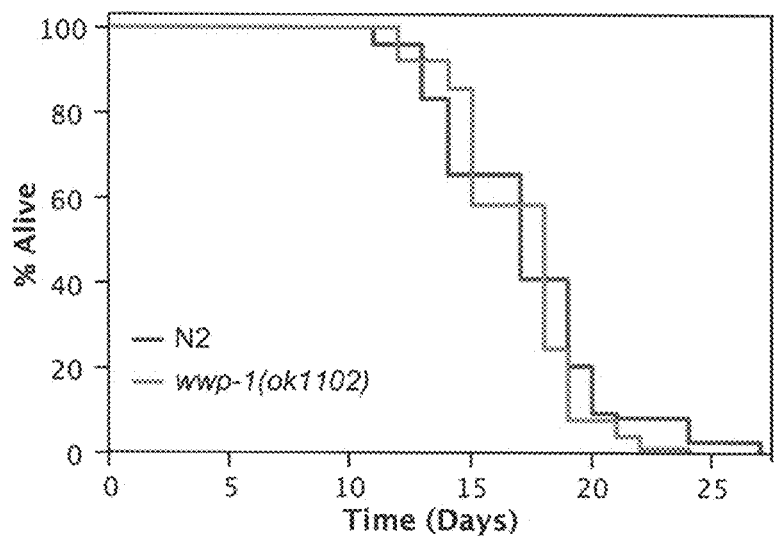
Figure 8C:
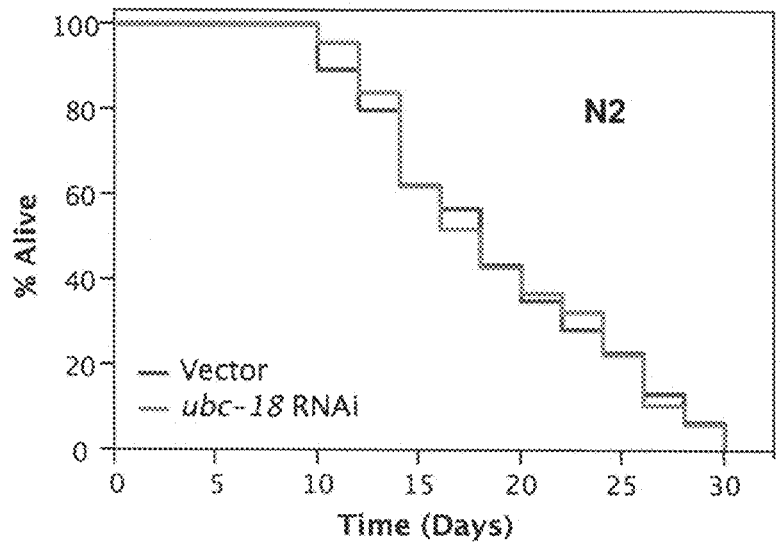
Figure 9A:
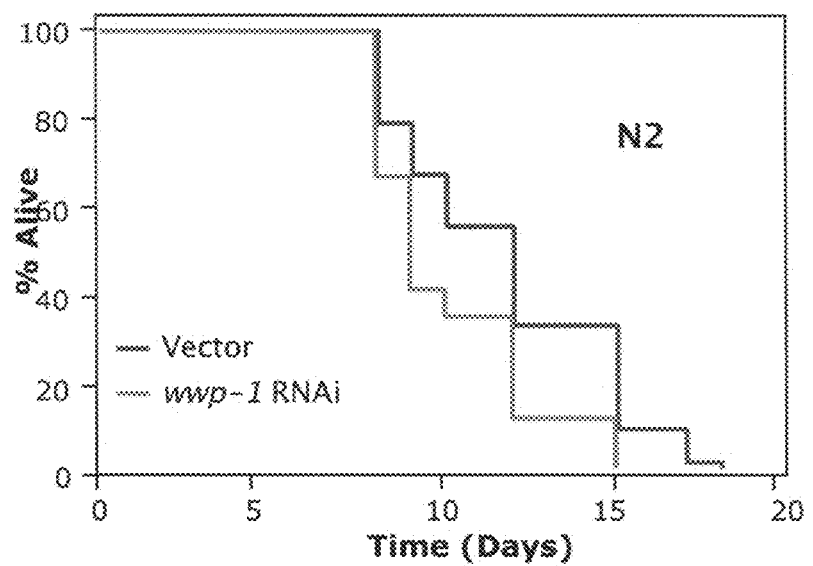
FIG. 9 Panels A-B present line graphs showing that mild heat stress shortens lifespan with loss of wwp-1. Panel A illustrates lifespan analysis of N2 worms fed wwp-1 RNAi or control vector at 25° C. Panel B illustrates lifespan analysis of N2 or wwp-1(ok1102) mutant worms at 25° C.
Figure 9B:
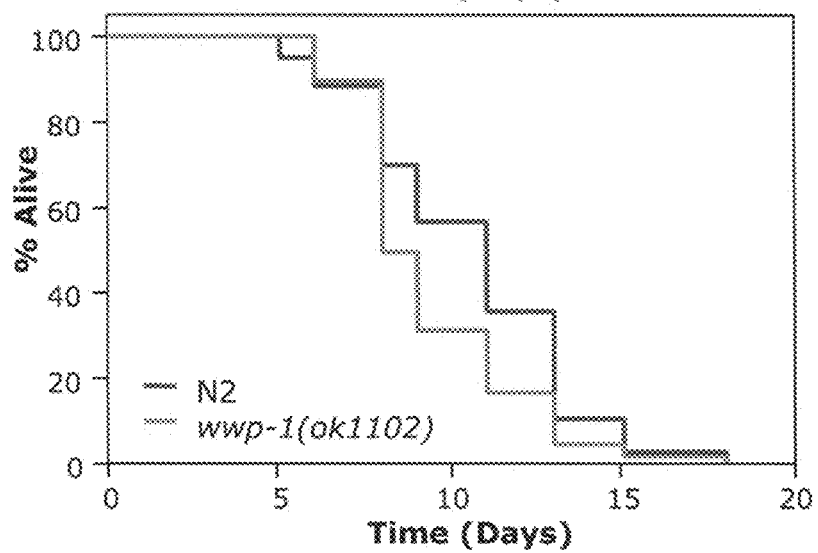
Figure 11B:
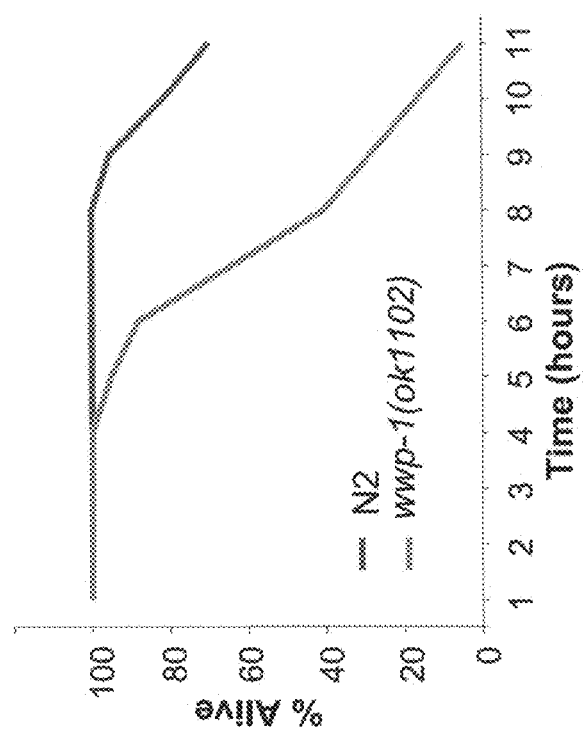
FIG. 11 Panels A-B indicate that wwp-1 regulates stress resistance. Panel A presents a graph showing wwp-1 dsRNA fed N2 animals are more sensitive to paraquat (300 mM) (Vector: mean=4.7±0.3, n=40; wwp-1 RNAi: mean=2.7±0.2, n=40, P<0.0001 vs. vector). Panel B presents a graph showing wwp-1(ok1102) mutant animals are more sensitive to heat stress (35° C.) (n=44).
Figure 11A:
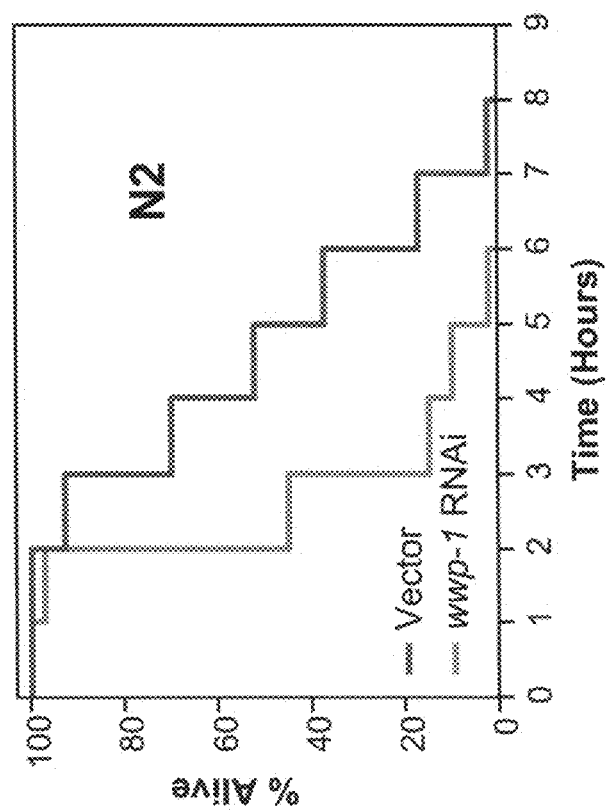

Prompted by studies in *C. elegans* and *Drosophila* showing that the nervous system can control longevity 10-14 and since wwp-1 plays an essential role in stress resistance in *C. elegans* (independent of the early developmental function of wwp-1, we found that loss of wwp-1 decreased stress resistance, both heat and oxidative, during adulthood; FIG. 11 Panels A-B), we went on to determine if wwp-1 plays a role in longevity in *C. elegans*. Loss of wwp-1 function by RNAi or wwp-1 mutant animals had no affect on lifespan at 20° C. (see FIG. 8 Panels A-B and Table 3). However, we did observe shortened lifespan at 25° C. (FIG. 9 Panels A-B and Table 3). To investigate if increased expression of wwp-1 extended longevity in worms, we compared the lifespan of our transgenic lines that overexpress WWP-1 (GFP::WWP-1) to a control line that expresses GFP under the same endogenous promoter. Our two independent wwp-1 overexpressing lines had lifespans extended by 20% compared with the control (FIG. 1 Panel A and Table 1) implying that wwp-1 is a positive regulator of lifespan.

When diet is restricted (Dietary Restriction or DR), lifespan is extended in diverse species suggesting that there is a conserved mechanism for nutrient regulation of aging. DR can be reproduced genetically by using eat-2 mutant worms. eat-2 mutations cause neuronal and muscular defects that impair pumping of the pharynx, which results in increased longevity, presumably by enforcing a DR regimen[15-7]. We fed eat-2(ad1116) mutant animals bacteria expressing wwp-1 dsRNA or empty vector as a control. Reduced levels of WWP-1 completely suppressed the extended longevity of eat-2 mutant animals (FIG. 1 Panel B). Suppression of DR extended lifespan by WWP-1 depletion is not likely due to an increased food intake, since we did not see a difference in pharyngeal pumping rates with loss or knockdown of wwp-1 (N2 treated with vector RNAi, 205.2±15.2 pumps per min (±s.d.); N2 treated with wwp-1 RNAi, 201.5±11.1 pumps per min; wwp-1(ok1102) treated with vector RNAi, 202.2±21.1; eat-2(ad1116) treated with vector RNAi, 50.3±11.9; eat-2 (ad1116) treated with wwp-1 RNAi, 53.3±10.1).

The first report of DR-induced longevity in C. elegans involved dilution of E. coli in buffer[18]. A decrease of E. coli concentration reduced fertility and increased lifespan. Because reduced wwp-1 gene activity suppressed the extended lifespan of eat-2 mutant animals back to wild type levels, we tested whether wwp-1 mutant animals can suppress the extended longevity of true dietary restriction. N2 animals showed a bell-shaped like curve for life expectancy in response to varying bacterial concentrations (FIG. 1 Panel D and Table 2). N2 animals grown under optimal DR conditions had a lifespan of more than double that of animals fed ad libitum (AL) (FIG. 1 Panels C-D). In contrast, the lifespan of wwp-1 (ok1102) mutant worms did not change dramatically when cultured in identical bacterial concentrations (FIG. 1 Panels C-D).

Figure 17A:
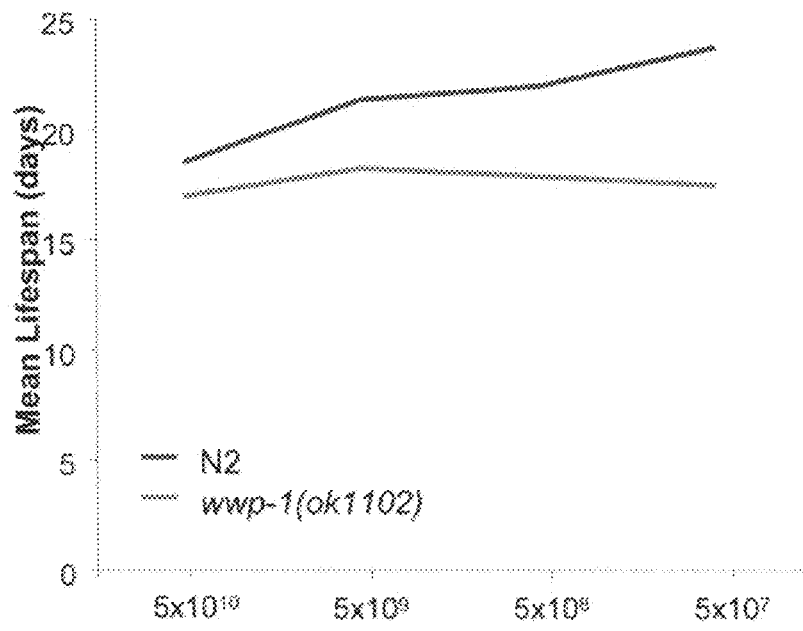
FIG. 17 Panels A-B illustrate that wwp-1 is required of solid plate DR. Panel A presents a graph of lifespans of N2 and wwp-1(ok1102) mutant animals grown on NG plates with different *E. coli* concentrations. Panel B presents a graph of lifespan analysis of N2 and wwp-1(ok1102) mutant worms grown in DR or AL *E. coli* concentrations.
Figure 17B:
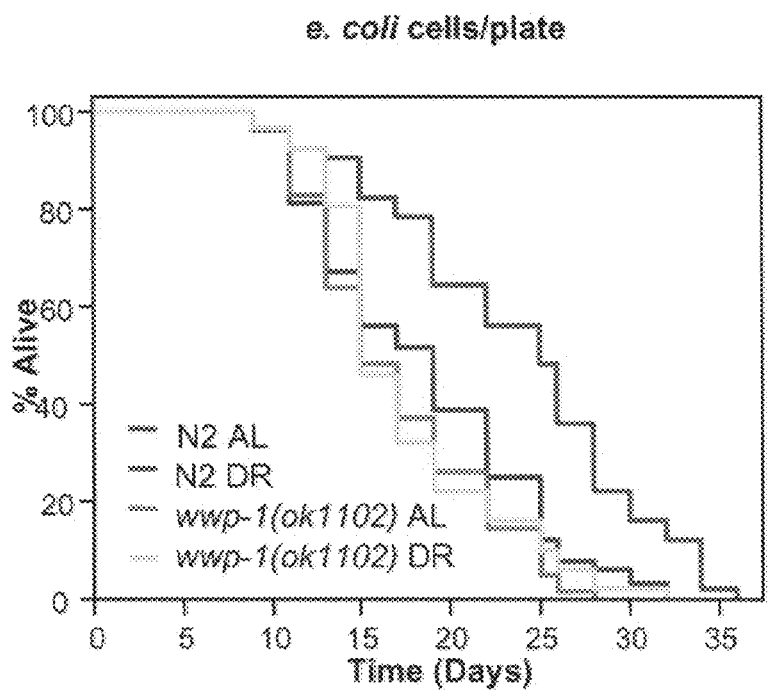
Figure 18A:
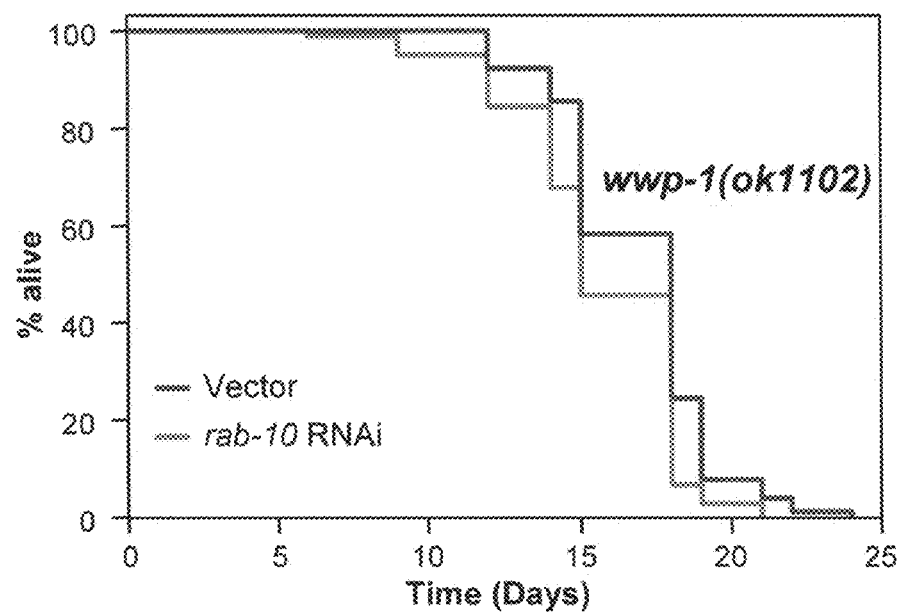
FIG. 18 Panels A-B illustrate that wwp-1 is required for the extended lifespan of N2 animals fed bacteria expressing rab-10 dsRNA. Lifespan analysis of wwp-1(ok1102) mutant animals fed bacteria expressing rab-10 RNAi or vector control (Panel A) or N2 animals fed bacteria expressing both rab-10 and wwp-1 dsRNA or rab-10 and vector control (Panel B) is shown.
Figure 18B:
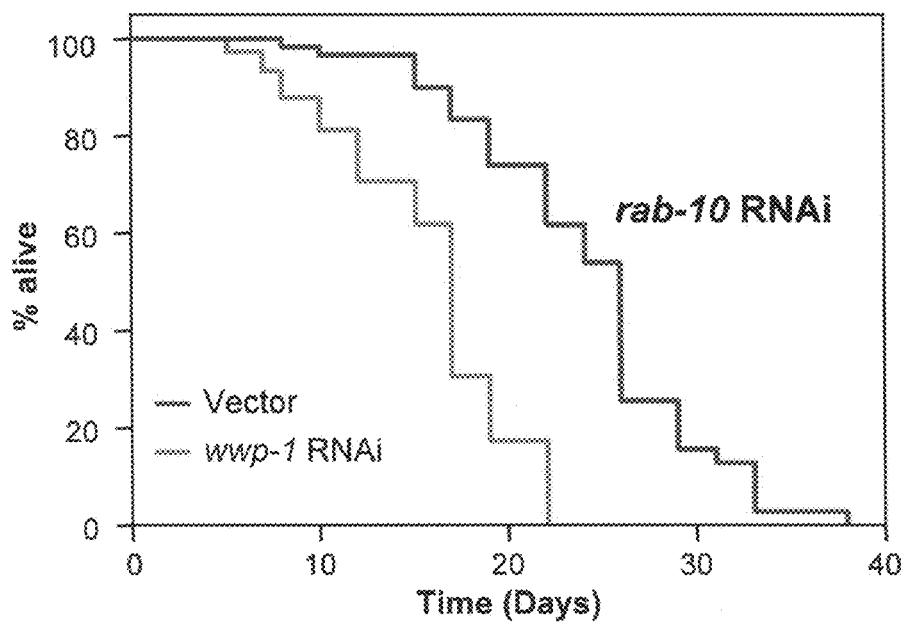
Figure 19A:
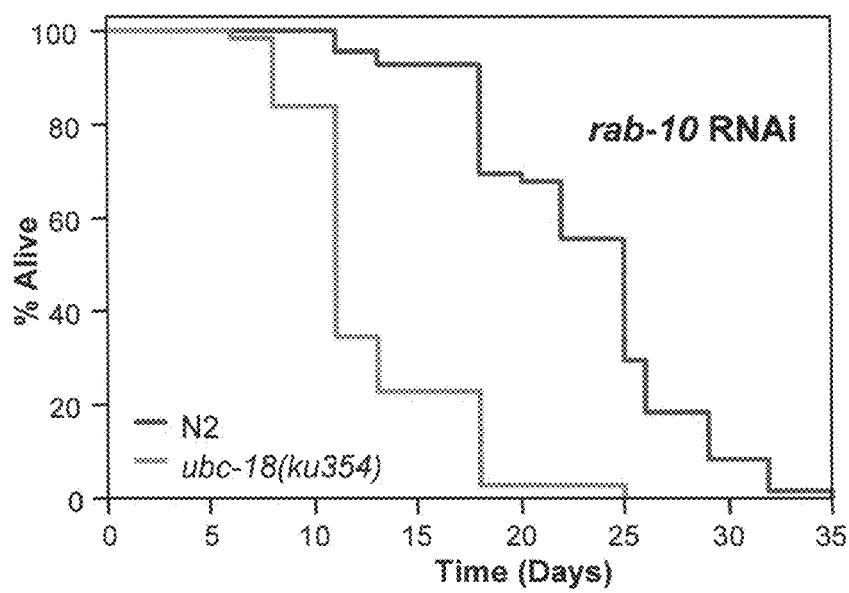
FIG. 19 Panels A-B illustrate that ubc-18 is required for the extended lifespan of N2 animals fed bacteria expressing rab-10 dsRNA. Lifespan analysis of N2 or ubc-18(ku354) mutant animals fed bacteria expressing rab-10 RNAi (Panel A) or N2 animals fed bacteria expressing both rab-10 and ubc-18 dsRNA or rab-10 and vector control (Panel B) is shown.
Figure 19B:
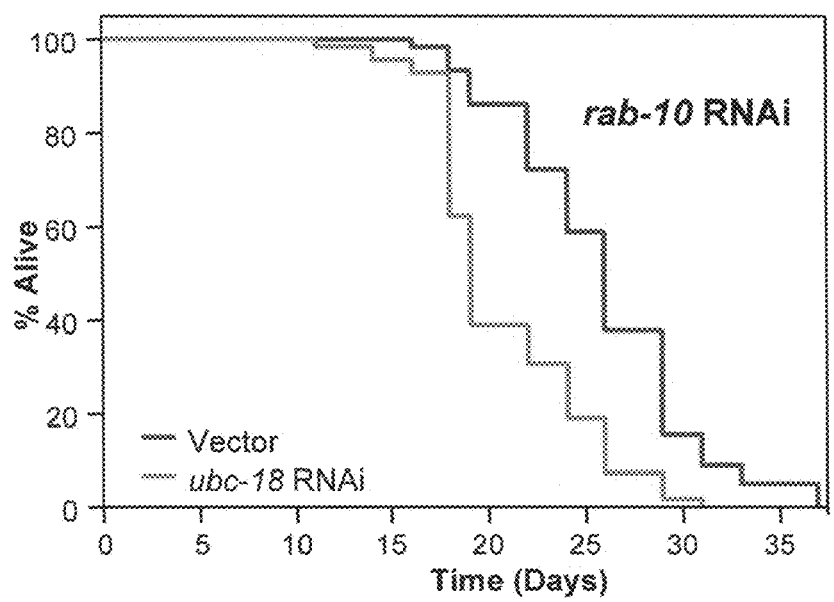

Similar results were observed using a different dietary restriction protocol in which the E. coli are grown on solid plates (FIG. 17 Panels A-B). Since different methods of DR may potentially activate distinct signaling pathways or activate them to varying degrees (e.g., because they restrict food intake by different methods), we also present data using solid plate DR as an additional method to look at DR induced longevity. This method was first developed and verified in Anne Brunet's laboratory[61]. Adult worms are transferred every 2 days to freshly seeded plates with restrictive amounts of bacteria ($5 \times 10^7$ to $5 \times 10^{10}$ bacteria/ml) starting at day 5 of adulthood. This method differs from bacterial dilution DR in that animals are not in liquid (reducing osmotic stress) and that it does not use antibiotics (which may extend lifespan by reducing food-related toxicity). We found that, like under bacterial dilution DR, the lifespan of wwp-1(ok1102) mutant animals did not change in response to varying bacterial concentrations under the solid plate DR protocol (FIG. 17 Panels A-B and Table 5).

Since the lifespan of wwp-1(ok1102) animals grown in DR conditions (whether bacterial dilution DR or solid plate DR) was not extended and did not change in response to varying bacterial concentrations, we conclude that wwp-1 is essential in the increased longevity response to DR.

Recently, the Foxa transcription factor pha-4 has been shown to mediate DR induced longevity in C. elegans[19]. Using our wwp-1 overexpressing lines, we found that loss of pha-4 expression by RNAi suppressed the increased longevity of these worms (FIG. 1 Panel E). This was not seen when these worms were fed bacteria expressing dsRNA against daf-16, the forkhead transcription factor involved in insulin/IGF1 signaling[20,21] (FIG. 1 Panel F).

Figure 15A:
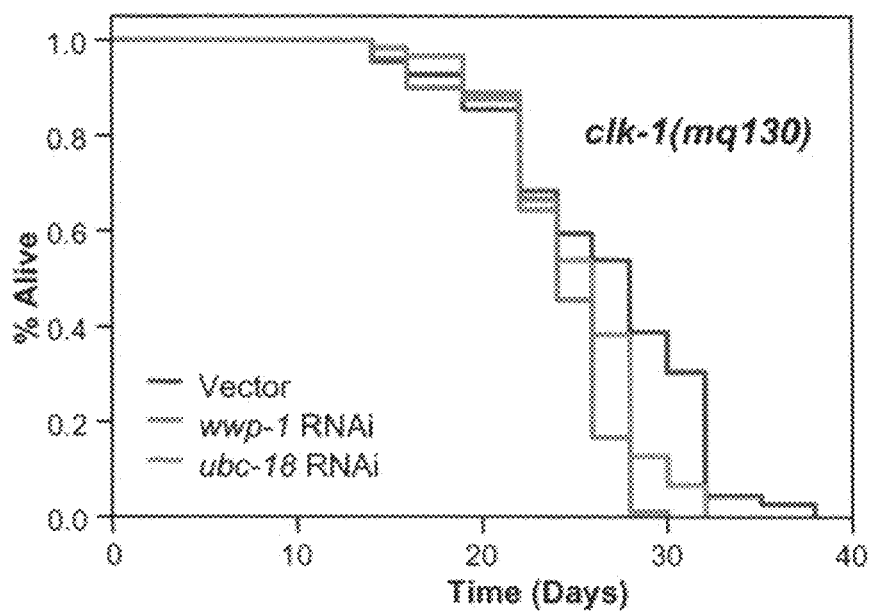
FIG. 15 Panels A-B illustrate that loss of wwp-1 and ubc-18 does not fully suppress the extended lifespan of animals with reduced mitochondrial function. Panel A presents a graph of lifespan analysis of clk-1(qm30) mutant worms fed bacteria expressing wwp-1 dsRNA, ubc-18 dsRNA or control vector. Panel B presents a graph of lifespan analysis of N2 and wwp-1(ok1102) mutant worms fed bacteria expressing cyc-1 dsRNA.
Figure 15B:
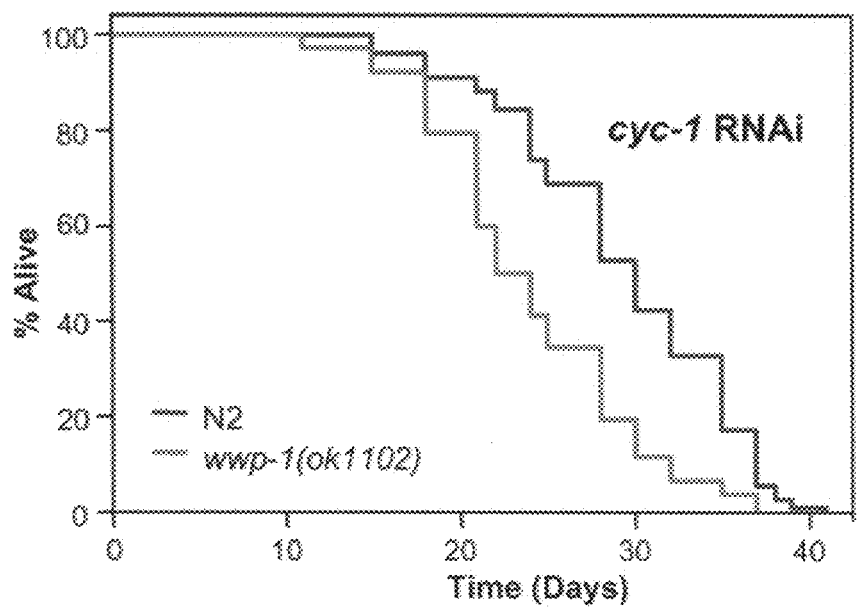

To determine whether wwp-1 was acting specifically to affect DR longevity, we examined the effect of loss of wwp-1 function on other pathways that influence longevity. Reduction of mitochondrial function by RNAi or mutation increases lifespan. Mutations in the iron sulfur component of complex III, isp-1, increase longevity by decreasing oxygen consumption[22-24]. We tested whether wwp-1 was required for the increased longevity of isp-1(qm150) mutants. RNAi of wwp-1 did not suppress the extended lifespan of these animals (FIG. 1 Panel G). In addition, loss of wwp-1 did not fully suppress the extended lifespan of clk-1(qm30) mutant animals or N2 animals fed bacteria expressing cyc-1 dsRNA (FIG. 15 Panels A and B, respectively).

Figure 10A:
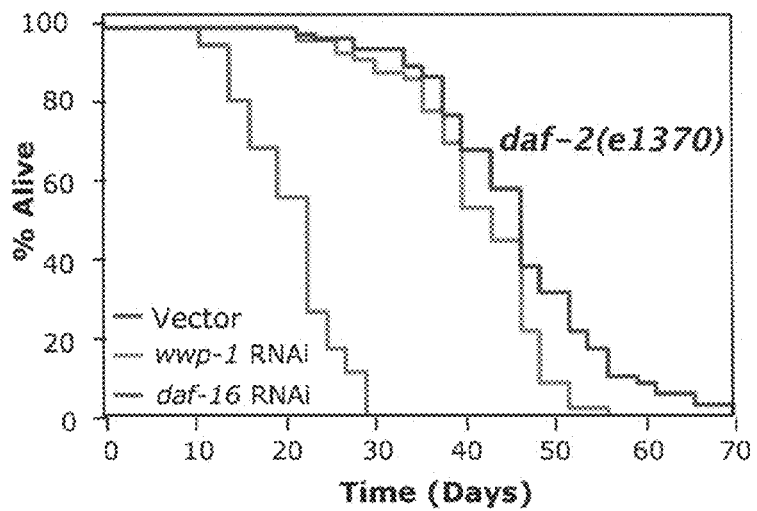
FIG. 10 Panels A-B present line graphs showing that loss of wwp-1 or ubc-18 partially suppresses the increased longevity of daf-2(e1370) mutants. Lifespan analysis of daf-2(e1370) fed bacteria expressing wwp-1 dsRNA (Panel A), ubc-18 dsRNA (Panel B), daf-16 dsRNA or control vector is shown. The reduction of the mean lifespan of daf-2(e1370) mutant animals may be explained by the fact that the two classes of daf-2 alleles can act very differently: daf-2(e1370) mutant animals exhibit a slight eat mutant phenotype, whereas daf-2(e1368) mutant animals do not.
Figure 10B:
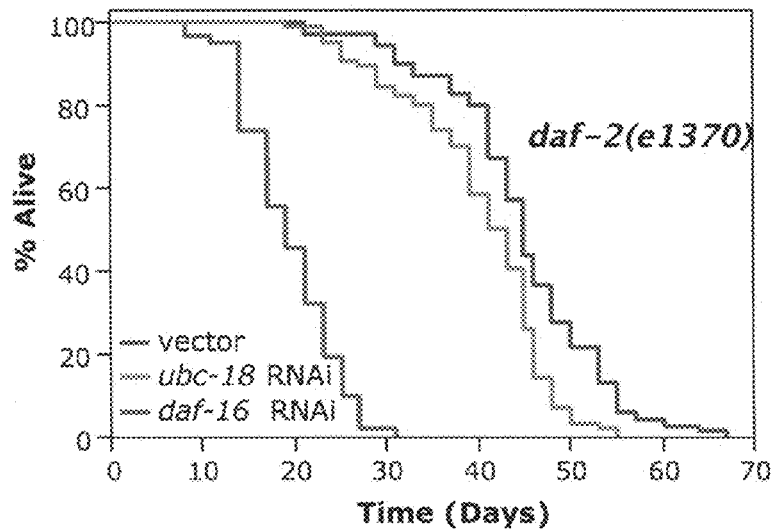

Partial loss of function mutations in the insulin/IGF-1 receptor homolog DAF-2 double lifespan[25]. This is dependent on the forkhead family transcription factor DAF-16. While RNAi knockdown of daf-16 completely suppressed the long lifespan of the daf-2(e1368) mutant animals, we saw no difference in lifespan in these animals fed wwp-1 dsRNA or vector control (FIG. 1 Panel H). Similar results were seen using daf-2(e1370) mutants (FIG. 10 Panel A). RNAi knockdown of daf-16 had no significant effect on the increased longevity we see with our WWP-1 overexpressing worms (FIG. 1 Panel F). Our results indicate that wwp-1 is not essential for longevity in this pathway.

Figure 2A:
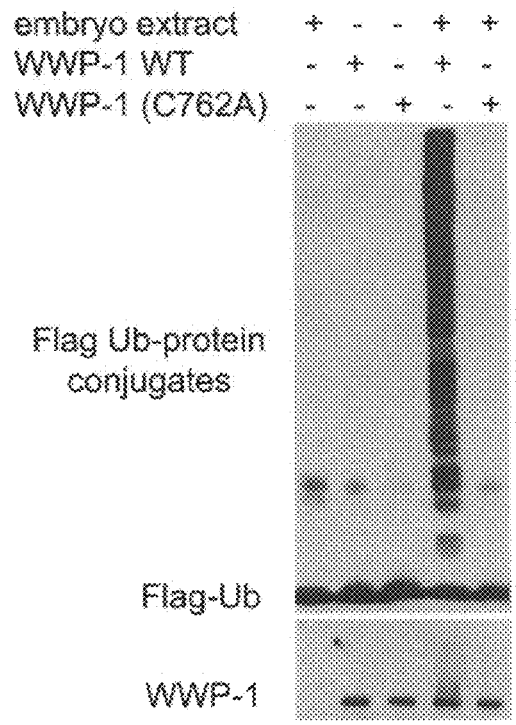
FIG. 2 Panels A-B illustrate that WWP-1 ubiquitin ligase activity is essential for DR induced longevity. Panel A presents data from an in vitro ubiquitination assay of WT WWP-1 or mutant WWP-1 (C762A) using $C.$ $elegans$ embryo extract, showing that mutation of the conserved catalytic cysteine of WWP-1 abolishes its ubiquitin ligase activity. Panel B presents a line graph showing that eat-2(ad116) mutant worms expressing a dominant negative wwp-1 (C762A) have significantly shorter lifespans than control worms expressing GFP.
Figure 2B:
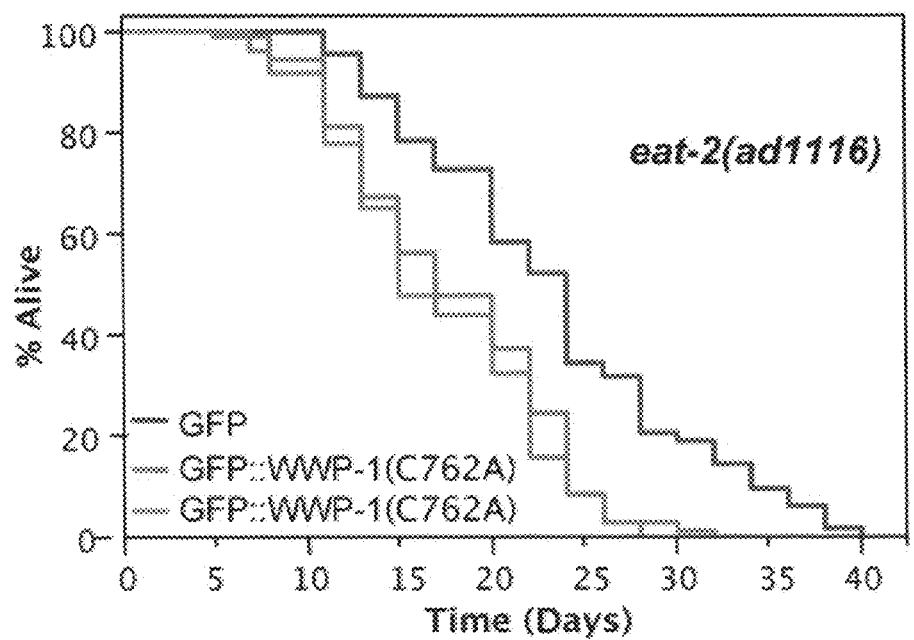
Figure 3A:
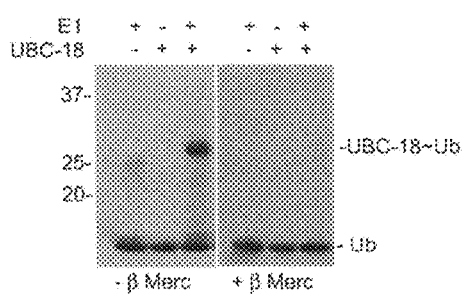
FIG. 3 Panels A-D illustrate that the E2 ubc-18 is essential for DR induced longevity. Panel A presents data from an in vitro ubiquitin conjugation reaction in which samples were subjected to SDS/PAGE with or without β-mercaptoethanol (β-mercap), showing that UBC-18 forms thiol sensitive adducts with ubiquitin. The position of molecular mass standards are shown to the left. Panel B presents a line graph showing that the ubc-18 is essential for increased longevity of eat-2 mutants; lifespan analysis of eat-2(ad1116) mutant worms fed ubc-18 dsRNA or control vector is presented. Panels C-D present line graphs showing that loss of ubc-18 does not effect other longevity pathways. Panel C presents a line graph showing that feeding ubc-18 dsRNA cannot suppress the extended longevity of isp-1 (qm150) mitochondrial mutant worms. Panel D presents a line graph showing that ubc-18 is not required for increased longevity of DAF-2 signaling; lifespan analysis of daf-2(e1368) fed ubc18 dsRNA or control vector is presented.
Figure 3B:
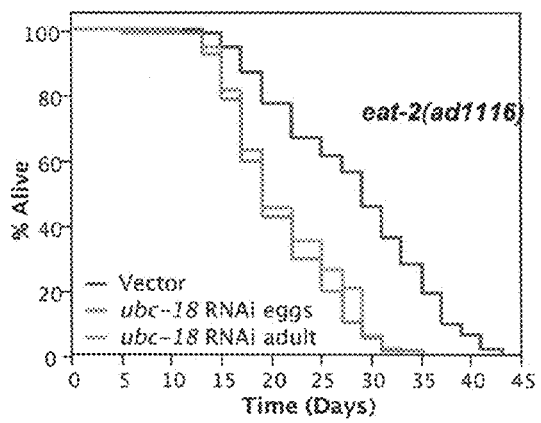
Figure 3C:
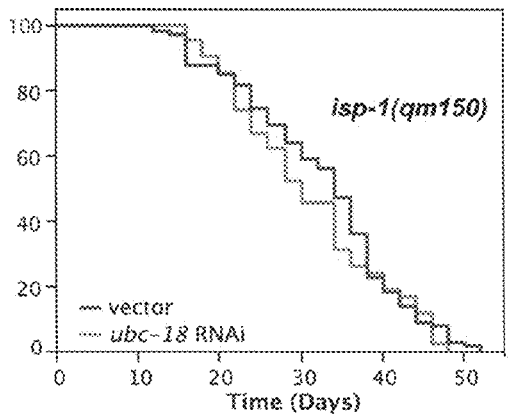
Figure 3D:
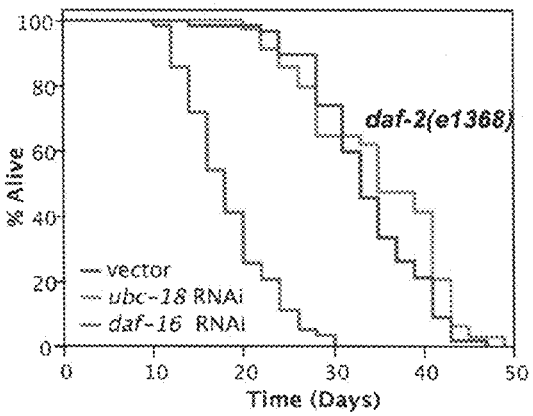
Figure 4A:
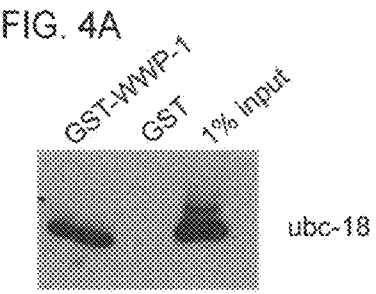
FIG. 4 Panels A-D illustrate that WWP-1 and UBC-18 function together to regulate DR induced longevity. Panel A presents data from a GST pulldown assay in which GST WWP-1 (or GST alone) bound to glutathione agarose beads was incubated with lysates from NIH3T3 cells expressing UBC-18 by transient transfection, showing that the E2 UBC-18 physically associates with WWP-1. Panel B illustrates that UBC-18 is essential for ubiquitin ligase activity in vitro. The left panel presents data from an in vitro ubiquitination assay of WT WWP-1 using WT *C. elegans* embryo extract (N2) or extract from ubc-18 mutant extracts [ubc-18(ku354)]; recombinant UBC-18 was added in the last lane. The right panel presents data from an in vitro ubiquitination assay using purified components. Panel C presents a line graph showing that wwp-1 and ubc-18 are epistatic; lifespan analysis of eat-2(ad1116) mutant animals fed bacteria expressing wwp-1 dsRNA and vector plasmid (wwp-1 RNAi), ubc-18 dsRNA and vector plasmid (ubc-18 RNAi) or wwp-1 and ubc-18 dsRNA is presented. Panel D presents a line graph showing that ubc-18 knockdown suppresses the lifespan of wwp-1 overexpressing worms; lifespan analysis of wwp-1 overexpressing worms (GFP::WWP-1) or control worms (GFP) fed bacteria expressing ubc-18 dsRNA or control vector is shown.
Figure 4B:
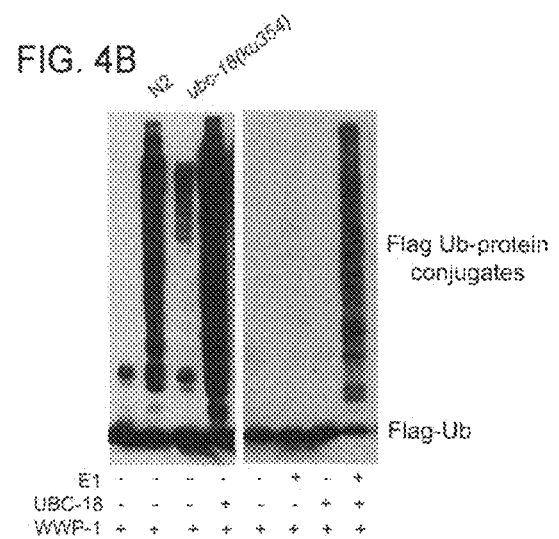
Figure 4C:
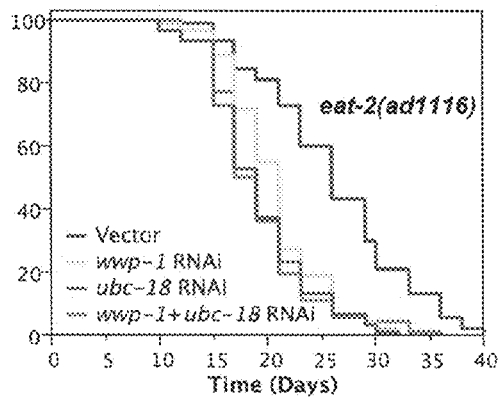
Figure 4D:
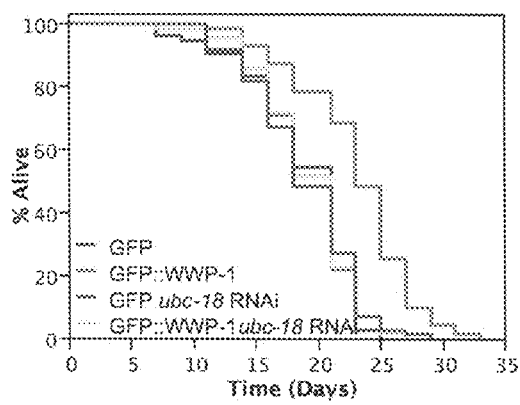

Ubiquitination by HECT ubiquitin ligases require the intermolecular transfer of ubiquitin from an associated E2 to the E3 ligase prior to transfer to the target. These transfers are dependent on the formation of a thioester bond between ubiquitin and a conserved cysteine residue that is localized close to the C-terminus of the HECT domain. HECT proteins with a point mutation of this site are catalytically inactive and act as dominant negative mutants in vivo[26]. We established an in vitro ubiquitination assay for WWP-1 ligase activity using C. elegans embryo extract as a source of substrates. We found that, in the presence of extract, WWP-1 had very robust ligase activity which was abolished with a point mutation to the catalytic cysteine (C762A) (FIG. 2 Panel A). To determine if the ubiquitin ligase activity of WWP-1 is essential for the extended longevity seen when animals are dietarily restricted, we compared the longevity of eat-2(ad1116) transgenic animals that overexpress a GFP-WWP-1 (C762A) fusion protein under the control of the wwp-1 promoter to a control line that express GFP under the same promoter. We found that two independent transgenic lines overexpressing the dominant negative wwp-1 had significantly shorter lifespans comparable to WT animals (FIG. 2 Panel B). This indicates that ubiquitin ligase activity of WWP-1 is essential for DR induced longevity.

UBC-18 is a putative E2 that has been shown to regulate pharyngeal development[27-29]. ubc-18 shows greatest similarity to UbCH7 in humans, and is also similar to S. cerevisiae E2 proteins Ubc5p and Ubc4p[29]. Recently a two-hybrid screen using UBC-18 as a bait molecule identified three ubiquitin ligases that interacted with UBC-18, including WWP-1 and a ring finger E3 ligase, ARI-1 and F56D2.2[27]. Inactivation of wwp-1 by dsRNA treatment failed to produce a pharynx unattached phenotype in pha-1(e2123) animals like ubc-18 and ari-1 dsRNA indicating that WWP-1 functions with UBC-18 to ubiquitinate targets not involved in pharyngeal development[27]. Similar to WWP-1, UBC-18 is expressed in head and tail neurons (FIG. 16 Panels A-H).

We have been able to show that UBC-18 is indeed a functional E2 and is capable of forming a thiol ester bond with ubiquitin (FIG. 3 Panel A). We went on to investigate if ubc-18 was essential for DR-induced longevity like wwp-1. Like wwp-1, ubc-18 loss did not affect N2 lifespan (FIG. 8 Panel C). We found that worms fed ubc-18 dsRNA completely suppressed the increased longevity of eat-2 mutants (FIG. 3 Panel B). This decreased lifespan is not likely due to impaired pharynx function since we initiated RNAi at the L1 stage when the pharynx is completely developed. RNAi initiated at D1 adults gave similar results (FIG. 3 Panel B). Suppression of DR extended lifespan by ubc-18 depletion is not likely to be due to an increased food intake, since we did not see a difference in pharyngeal pumping rates with loss of ubc-18 [N2 treated with ubc-18 RNAi, 200.6±13.2 (±s.d.); eat-2(ad1116) treated with ubc-18 RNAi, 49.1±8.3]. ubc-18 was acting specifically to affect DR longevity, since RNAi of ubc-18 initiated at L1 stage had no effect on reduction of mitochondrial function (FIG. 3 Panel C) and daf-2 longevity (FIG. 3 Panel D and FIG. 10 Panel B). These results indicate WWP-1 and UBC-18 act in similar pathways.

Figure 13A:
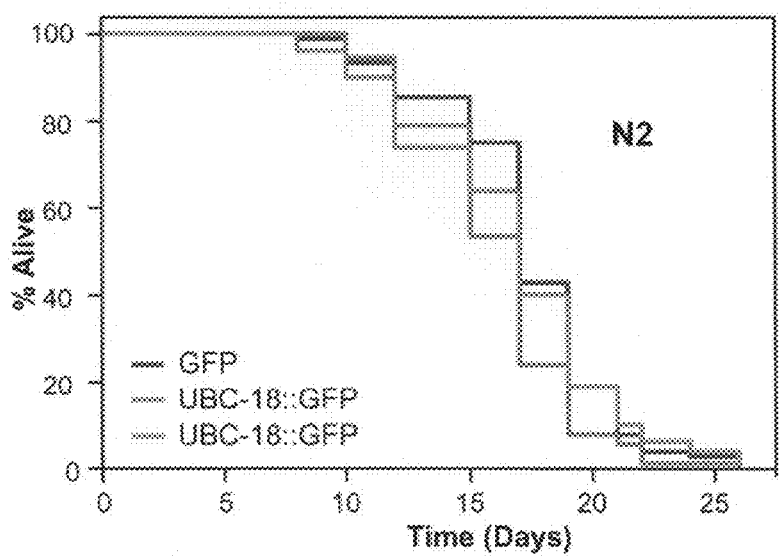
FIG. 13 Panels A-B illustrate that overexpression of ubc-18 does not extend lifespan. Panel A presents a graph showing that two independent strains expressing UBC-18-GFP fusion protein (UBC-18::GFP) do not extend longevity compared to control worms expressing gfp. Panel B presents a graph showing that three independent strains expressing non-tagged UBC-18 (UBC-18) do not extend longevity compared to control worms expressing gfp.
Figure 13B:
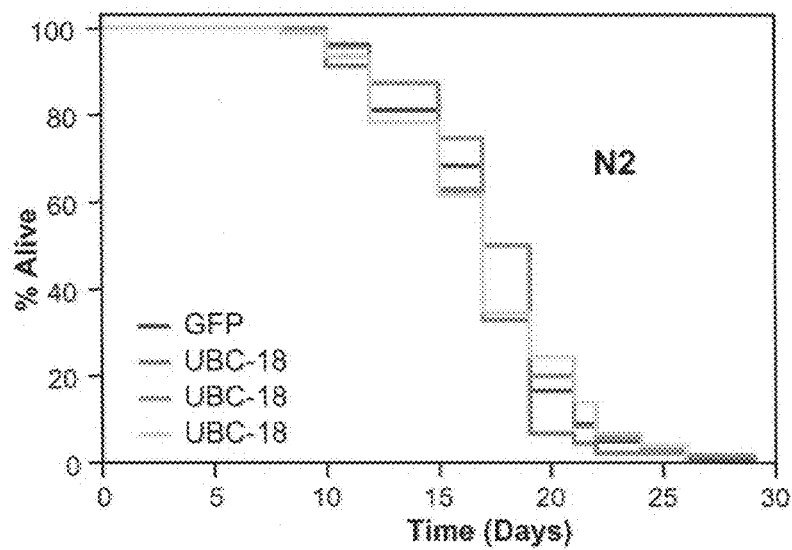
Figure 14:
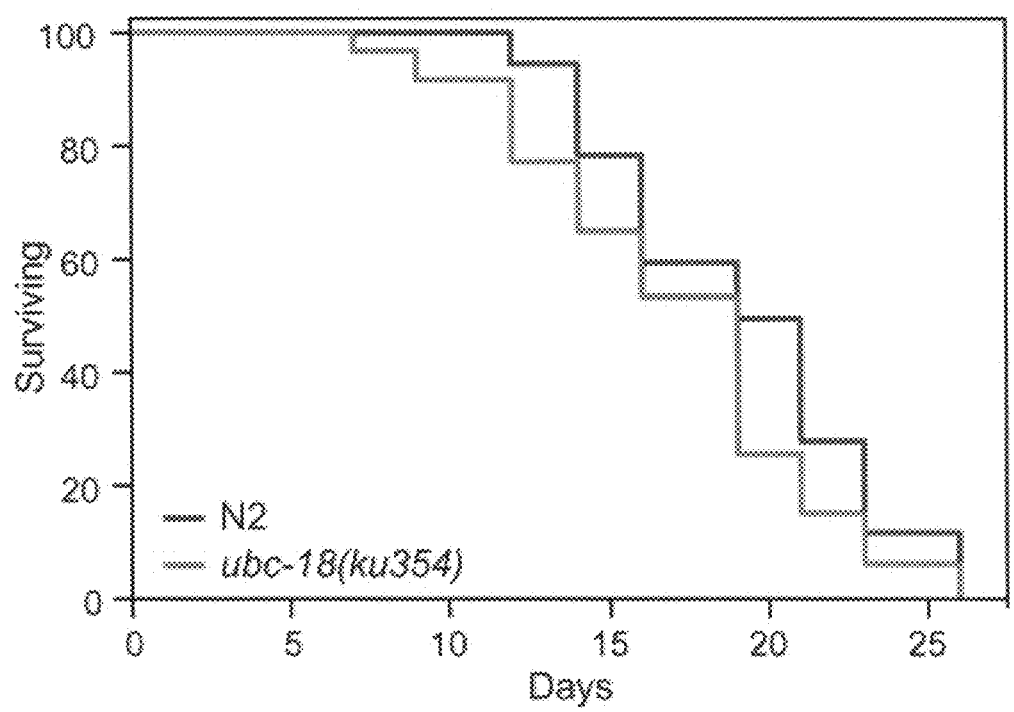
FIG. 14 presents a line graph of lifespan analysis of ubc-18(ku354) mutant animals compared to N2 animals, showing that ubc-18 mutant animals have slightly shorter lifespans.

Incidentally, we note that ubc-18(ku354) mutant animals had slightly shorter lifespans than N2 animals (FIG. 14) and that overexpression of ubc-18 did not extend lifespan (FIG. 13 Panels A-B), probably due to ubc-18's role in pharyngeal development. We have generated transgenic animals that express ubc-18 GFP fusion protein under the control of the endogenous ubc-18 promoter. We found that overexpression of this fusion protein does not extend lifespan (FIG. 13 Panel A). It was possible that we did not see extension because the GFP tag interfered with UBC-18 function (and in fact, we were not able to see E2 activity of our recombinant UBC-18 unless we removed its GST tag). However, we do not see lifespan extension in animals that express untagged ubc-18 under the control of its endogenous promoter (FIG. 13 Panel B). Because ubc-18 also plays a role in early development in the worm and we know that ubc-18(ku354) mutant animals have shorter lifespans, most likely due to general sickness (FIG. 14), it is possible that the developmental effects of ubc-18 expression negate any subtle extension that may otherwise have been observed.

Given that UBC-18 is a functional E2 and essential for DR longevity, we went on to see if wwp-1 and ubc-18 function together to regulate DR induced longevity. To confirm the association between WWP-1 and UBC-18, a GST pull-down assay was performed. UBC-18-Myc fusion protein from transiently transfected NIH3T3 cell extract could be pulled down by GST fused WWP-1 (FIG. 4 Panel A). UBC-18 was also essential for WWP-1 ubiquitin ligase activity in vitro (FIG. 4 Panel B). We saw a great reduction in WWP-1 induced ubiquitination when using embryo extract from ubc-18(ku354) mutant worms. However, ligase activity was restored with the addition of recombinant UBC-18. Using a purified system, we show that WWP-1 exhibited ubiquitin ligase activity in an E1 and UBC-18 dependent manner. In addition, epistasis analysis of wwp-1 and ubc-18 showed that knockdown of both genes by double RNAi in eat-2(ad116) animals did not shorten lifespan any further than RNAi of a single gene (FIG. 4 Panel C). Finally, we show that knockdown of ubc-18 can suppress the extended lifespan we see with our wwp-1 overexpressing animals (FIG. 4 Panel D).

Figure 12:
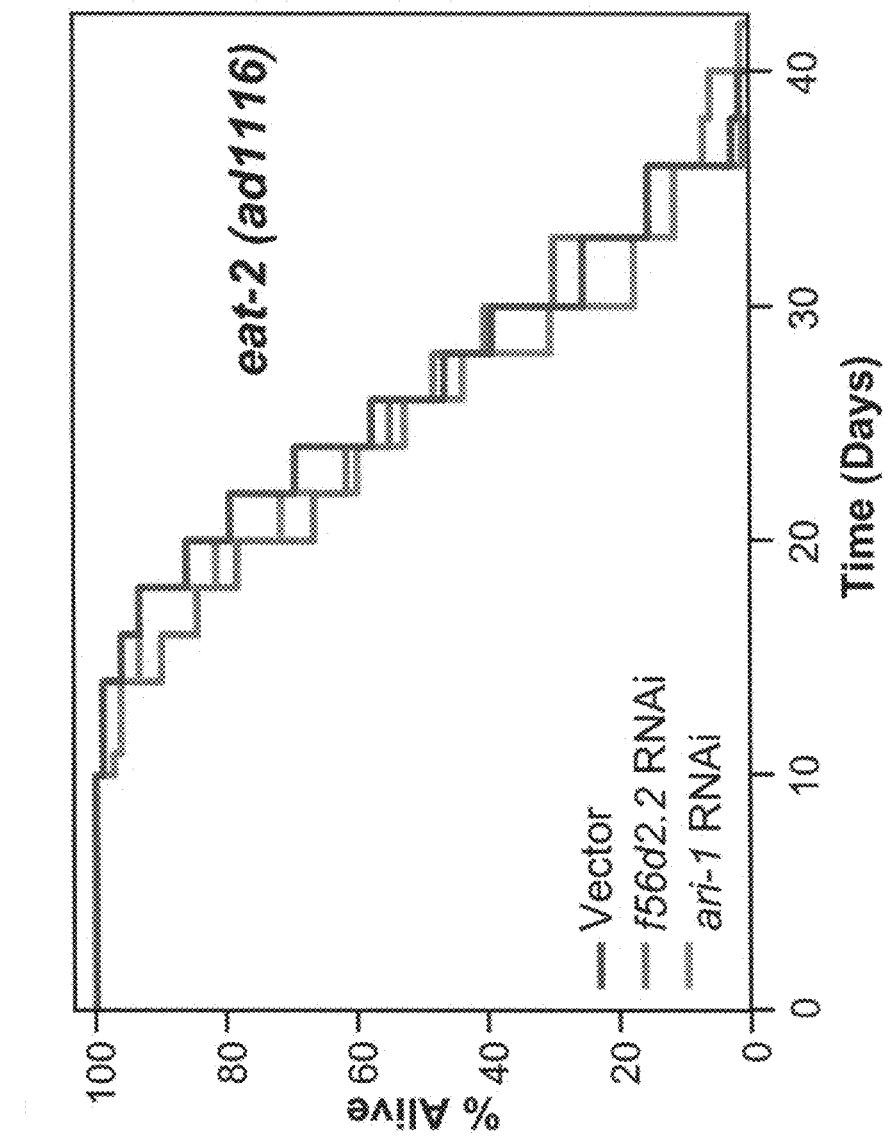
FIG. 12 shows that depletion of other ligases that interact with UBC-18 do not affect the extended lifespan of eat-2 mutant animals. A graph of lifespan analysis of eat-2(ad1116) mutant worms fed bacteria expressing f56d2.2, ari-1 or vector control is presented. RNAi was initiated at day 1 of adulthood. Lifespan values are given in Table 3.

In summary, the UBC-18/WWP-1 complex functions to specify the longevity response of diet restricted animals. Loss of either wwp-1 or ubc-18 specifically suppressed the extended longevity of DR animals while not affecting mitochondrial or Insulin/IGF-1 perturbed animals. Because E2s often function with multiple E3s, it is surprising to find that ubc-18 was essential, but also specific for the response to DR. The other E3s found to interact with UBC-18 may be dedicated instead to the developmental function of UBC-18, as is the case for ARI-1[27]. In fact, RNAi depletion of these ligases had no effect on the extended lifespan of eat-2 mutant animals (FIG. 12 and Table 4).

Several targets have been identified for the mammalian orthologs of wwp-1. Mammalian WWP1 has been shown to associate in vitro with the transcription factor NF-E2 and to polyubiquitinate and target the transcription factors LKLF, KLF5 and Runx2 for degradation[39-43]. Most recently, WWP1 has been reported to negatively regulate p53 by sequestering the protein in the cytoplasm[44]. WWP2 interacts with EBV latent membrane protein 2A (LMP2A) and also ubiquitinates the OCT-4 transcription factor[45,46]. Itch has been shown to associate with endophilin, and to ubiquitinate Notch, Occludin, HEF1, Smad7, JunB, c-Jun, p73, p63 and LMP2A[47-57]. Itch can also mediate ubiquitination of the G protein-coupled receptor CXCR4 at the plasma membrane, and of the ubiquitin-binding protein Hrs on endosomes[57].

Many of the mammalian targets described are transcription factors, suggesting that WWP-1 targets one or more of the transcription factors recently found to be essential for diet restricted longevity in the worm: pha-4 and skn-1b[19,38]. In addition, the genetic epistasis analysis of UBC-18/WWP-1 suggests PHA-4 as a target for ubiquitination, and SKN-1 is the worm ortholog of NF-E2 related transcription factors, Nrf1 and Nrf2. However, because ubc-18, wwp-1, pha-4 and skn-1b all appear to positively regulate longevity in response to DR, in one model (without limitation to any particular mechanism) the UBC-18/WWP-1 complex mono-ubiquitinates these transcription factors resulting in their activation, rather than mediating poly-ubiquitination and degradation of these targets. However, neither PHA-4 nor SKN-1b have PPxY motifs which recruit WW containing E3 ligases and have been shown to be essential for the binding of NF-E2 to the WW domains of mammalian WWP1[39]. Since both SKN-1b and PHA-4 are constitutively nuclear and we find that WWP-1 is located in the cytoplasm, even under conditions of stress and restricted diet, in another model (without limitation to any particular mechanism) WWP-1 targets transcription factors that undergo nucleo-cytoplasmic shuttling. Examples of transcription factors that undergo such shuttling include, but are not limited to, p53/cep-1, cJun, and daf-16. Furthermore, in one model (again without limitation to any particular mechanism) WWP-1 and the protein deacetylase Sir-2 act upon the same target, optionally the same lysine residue within the target, to help mediate the longevity response to diet restriction. Because both Sir2 and WWP-1 have been implicated in the response to diet restriction, in this model their mode of action is a combined two step mechanism in which SIR2 deacetylates critical lysine residues followed by ubiquitination by WWP-1.

Other substrates of interest include, but are not limited to, cep-1/p53 (see, e.g., Genbank accession no. NM_001026307 for C. elegans cep-1). Recent results identify p53 as a substrate for WWP1, where WWP1-mediated ubiquitination of p53 promotes its nuclear export and accumulation in the cytoplasm resulting in decreased p53 transcriptional activity[58,59]. In addition, expression of a dominant negative p53 in neurons can extend lifespan in Drosophila[62]; these results indicate that p53 is involved in DR longevity because expression of the dominant negative p53 in neurons can not further extend the lifespan of DR long lived animals, suggesting that a decrease in p53 activity may mediate a component of the DR lifespan-extending pathway in flies. Furthermore, loss of cep-1 can extend lifespan in *C. elegans*[60]

Methods

*C. elegans* Methods

Strain RB1178 including wwp-1(ok1102) was generated by the *C. elegans* Gene Knockout Consortium; a description of the RB1178 strain is available on the internet at www (dot) wormbase (dot) org/db/gene/strain?name=RB1178; class=Strain. The wwp-1 mutant strain used herein was generated by backcrossing RB1178 [wwp-1 (ok1102)] to N2 three times. The ubc-18(ku354) mutant was also generated by the *C. elegans* Gene Knockout Consortium (www (dot) wormbase (dot) org/db/gene/variation?name=ku354). Some strains were provided by the *Caenorhabditis* Genetics Center, which is funded by the NIH National Center for Research Resources (NCRR). Nematodes were handled using standard methods[30].

Lifespan Analysis

Lifespan analyses were performed as described previously[31]. JMP IN 5.1 software was used to determine means and percentiles. In all cases, p values were calculated using the log-rank (Mantel-Cox method). True DR lifespans were performed as described[19] with the following modifications: synchronized populations of eggs were hatched and grown at 20° C. on NG agar plates containing OP50 *E. coli* until the L4 larval stages when they were transferred to new plates of OP50 *E. coli* containing 100 μg/ml FUDR. At day 1 adulthood, worms were transferred into liquid culture and placed on a gentle rocker at 20° C. All lifespans presented are representative experiments from at least two independent experiments. All lifespans were performed at 20° C. unless noted.

RNAi Treatment

RNAi-treated strains were fed *E. coli* (HT115) containing an empty control vector pAD12 or *E. coli* expressing double-stranded RNA against the genes wwp-1, ubc-18, daf-2, pha-4, daf-16, ari-1 and f56d2.2. RNAi constructs for wwp-1 and ubc-18 were from established libraries previously described in Nature (2000) 408(6810):325-30 and Genome Res. (2004) 14(10B):2162-8, respectively. Double RNAi experiments were performed as described[32].

Creation of GFP::WWP-1 Constructs

To construct the plasmid expressing GFP::WWP-1 driven by wwp-1 endogenous promoter, sequences 644 bases upstream of the wwp-1 coding region (sequence immediately following stop codon of y54b4br.5 to sequence immediately before start codon of wwp-1) were amplified from genomic DNA by PCR and inserted upstream of GFP sequences in the worm expression vector pPD95.77. This construct (GFP), which expresses GFP under the control of the endogenous wwp-1 promoter, was used for a control in our experiments. To generate a N-terminal GFP fusion construct, point mutagenesis (Stratagene) was performed on PD95.77 to eliminate the stop codon in the gfp cDNA. Full length wwp-1 cDNA was amplified from a first strand cDNA from N2 worms by PCR and inserted into the N-terminal GFP fusion construct containing the wwp-1 endogenous promoter downstream and in frame with the gfp sequence at the N-terminus. This construct (GFP::WWP-1) expresses GFP-WWP-1 fusion protein under the control of the wwp-1 promoter. To generate the wwp-1 (C762A) dominant negative, point mutagenesis was performed on GFP::WWP-1 construct to generate GFP::WWP-1(C762A). Primers for N-terminal GFP mutagenesis: forward, TGGATGAACTATACAAA-GAATTCCAACTGAGCGC (SEQ ID NO: 1); reverse, GCGCTCAGTTGGAATTCTTTGTATAGTTCATCCA (SEQ ID NO:2). Primers for wwp-1 promoter: forward, GCTCTAGACTTGTTTCCTGATGACCTTG (SEQ ID NO:3); reverse, CGGGATCCTCGATCATGAAACTG-GCTG (SEQ ID NO:4). Primers for wwp-1: forward, ATG-GCTCGTAATGAACCATCATCTCAGCAG (SEQ ID NO:5); reverse, CTACTCGTTTCCAAATCCTTCCGT-CATCTC (SEQ ID NO:6). Primers for C762A dominant negative: forward, CCACGGTCGCATACGGCCT-TCAATCGACTCGAC (SEQ ID NO:7); reverse, GTC-GAGTCGATTGAAGGCCGTATGCGACCGTGG (SEQ ID NO: 8).

Generation of Transgenic Lines

The wwp-1 mutant strain was generated by backcrossing RB1178 [wwp-1 (ok1102)] to N2 three times. Nematodes were handled using standard methods 30. For generation of N2 animals overexpressing WWP-1, GFP::WWP-1 plasmid DNA construct described above was mixed at 20 μg/ml with 80 μg/ml of pRF4(rol-6) construct 33. For generation of eat-2(ad1116) worms overexpressing dominant negative WWP-1 (C762A), GFP::WWP-1(C762A) plasmid DNA was mixed at 30 μg/ml with 80 μg/ml of pRF4 (rol-6) construct. Worms used as controls against wwp-1 overexpressing strains contained 30 μg/ml GFP expressing construct described above injected with 30 μg/ml pRF4(rol-6). Mixtures were microinjected into the gonads of L4/early adult hermaphrodite animals using standard methods[33]. Transgenic F1 progeny were selected on the basis of roller phenotype. Individual transgenic F2 animals were isolated to establish independent lines. All transgenic wwp-1 overexpressing lines used had similar levels of expression as determined by GFP fluorescence.

GFP Localization

Paralyzed transgenic animals were assayed for GFP expression at 40× and 63× magnification using a Leica 6000B digital microscope. Images were acquired using Leica FW4000 software. Intestinal granule autofluorescence viewed with the DAPI filter.

RNA Isolation and RT-PCR

Total RNA was isolated from asynchronous populations of worms and extracted using TRIzol reagent (GIBCO). cDNA was created using Superscript II RT (Invitrogen) and oligo dT primers.

Recombinant Proteins and GST Pulldown Experiments

Full length wwp-1 cDNA (WT and C762A mutant) or ubc-18 cDNA was inserted into pGEX-KG bacterial expression vector. GST purification was performed according to the manufacturer's instructions (GE Healthcare). Flag tagged ubiquitin has been previously described[34,35]. For active protein, the GST tag on UBC-18 was removed by thrombin cleavage according to the manufacturer's instructions (GE Healthcare). To remove thrombin, the supernatant was incubated with Benzmidine Sepharose-4B beads (GE Healthcare) for 15 minutes at room temperature. Full length ubc-18 cDNA was inserted into pCDNA6/myc-His mammalian expression vector to generate a myc-His fusion protein. GST-pulldown experiments were performed using 500 μg NIH3T3 lysates expressing ubc-18 by transient transfection (Effectene, Qiagen). Lysates were prepared as previously described[36]. Lysates were incubated with GST-WWP-1 or GST bound to glutathione agarose beads for 1.5 hours. Beads were washed 4 times with lysis buffer and analyzed by SDS-PAGE. UBC-18 was detected by anti-myc (9E10) immunoblotting.

Protein Extraction for In Vitro Ubiquitination Assay

*C. elegans* embryos were isolated using an alkaline hypochlorite solution from gravid N2 worms grown at 20° C.[37] The embryos were resuspended in lysis buffer [50 mM Tris/Hcl (pH 7.5), 0.75 mM EDTA, 1.5 mM DTT, 2.5 mM PMSF, 1 μg/ml Aprotonin, 1 μg/ml leupeptin, 1 μg/ml Pepstatin A] and homogenized with 30 strokes in a Dounce homogenizer. The extract was then centrifuged 15,000×g at 4° C. and stored at −70° C.

In Vitro Ubiquitination Assay

The ubiquitin ligase assay was carried out by incubating 1 μg Flag tagged ubiquitin, 0.5 μg GST-WWP-1 (WT or C762A mutant), 0.1 μg UBC-18 and 15-20 μg embryo extract in 30 μl reaction buffer (50 mM Tris-HCl, pH 7.5, 5 mM $MgCl_2$, 1 mM DTT and 5 mM ATP) for 1 hour at 30° C. The reaction was stopped with sample buffer and run on protein gels under denaturing conditions. Ubiquitinated substrates were identified by anti-Flag (M2, Sigma) immunoblotting. For in vitro ubiquitination assay using just purified components similar conditions were administered except 0.5 μg UBC-18 and 1 μg E1 was used. To measure UBC-18 ubiquitin conjugation activity, a similar reaction was performed and the reaction was stopped with sample buffer without β-mercaptoethanol.

Stress Assays

For heat-shock assays, eggs from worms were transferred to plates seeded with various RNAi treatments and grown to D1 adulthood. Worms were then transferred to plates without food and heat shocked at 35° C. Worms were checked every 2 hours for viability. Paraquat (methyl viologen, Sigma) assays were performed as described[31]. For all stress assays a representative experiment from at least two independent experiments is presented.

Pumping Rate Assays

Pumping rates were determined by counting pumps of the terminal pharyngeal bulb for one-minute intervals to determine pumps per min. For each condition, worms were treated with bacteria expressing dsRNA since hatching. The pumping rates of ten D1 adult worms per condition were measured and averaged.

TABLE 1

Lifespan data for FIGS. 1-4.

| FIG. | Strain | Treatment | Mean Lifespan +/− SEM (Days) | p Value | $75^{th}$ Percentile | Total Animals Died/Total |
|---|---|---|---|---|---|---|
| 1a | N2 GFP[a] | | 16.6 ± 0.7 | | 22 | 54/90 |
| | N2 GFP::WWP-1[b] | | 20.0 ± 0.8 | 0.0047[c] | 23 | 48/72 |
| | N2 GFP::WWP-1[d] | | 20.4 ± 0.8 | 0.0003[c] | 25 | 65/90 |
| 1b | eat-2(ad1116) | vector | 28.3 ± 1.0 | | 35 | 66/80 |
| | eat-2(ad1116) | wwp-1 dsRNA | 17.1 ± 0.6 | <0.0001[e] | 18 | 73/80 |
| 1c | N2 | AL[f] | 27.0 ± 1.2 | | 36 | 73/91 |
| | N2 | DR[g] | 51.9 ± 1.8 | <0.0001[h] | 64 | 74/90 |
| | wwp-1(ok1102) | AL[f] | 20.3 ± 0.9 | | 22 | 71/90 |
| | wwp-1(ok1102) | DR[g] | 18.9 ± 1.0 | <0.0001[h], 0.3865[i] | 25 | 89/90 |
| 1e | N2 GFP[a] | Vector | 18.7 ± 0.5 | | 21 | 72/80 |
| | N2 GFP[a] | pha-4 dsRNA | 16.7 ± 0.5 | 0.0100[j] | 21 | 68/80 |
| | N2 GFP::WWP-1[k] | Vector | 23.1 ± 0.5 | <0.0001[j] | 27 | 70/80 |
| | N2 GFP::WWP-1[k] | pha-4 dsRNA | 17.5 ± 0.5 | 0.0164[j] 0.6058[l] | 21 | 66/80 |
| 1f | N2 GFP[a] | Vector | 18.1 ± 0.7 | | 21 | 58/80 |
| | N2 GFP[a] | daf-16 dsRNA | 17.2 ± 0.6 | 0.2682[j] | 21 | 64/80 |
| | N2 GFP::WWP-1[k] | Vector | 22.5 ± 0.7 | <0.0001[j] | 25 | 65/80 |
| | N2 GFP::WWP-1[k] | daf-16 dsRNA | 21.0 ± 0.7 | 0.2474[m], 0.0001[n] | 23 | 62/80 |
| 1g | isp-1(qm150) | Vector | 26.2 ± 1.1 | | 32 | 67/96 |
| | isp-1(qm150) | wwp-1 dsRNA | 28.1 ± 0.9 | 0.6438[o] | 32 | 49/80 |
| 1h | daf-2(e1368) | Vector | 33.5 ± 0.8 | | 39 | 57/80 |
| | daf-2(e1368) | wwp-1 dsRNA | 32.3 ± 0.8 | 0.5147[p] | 39 | 72/80 |
| | daf-2(e1368) | daf-16 dsRNA | 18.3 ± 0.6 | <0.0001[p] | 22 | 63/80 |
| 2b | eat-2(ad1116) GFP[a] | | 23.4 ± 0.9 | | 28 | 65/80 |
| | eat-2(ad1116) GFP::WWP-1(C762A)[q] | | 17.9 ± 0.7 | <0.0001[c] | 22 | 73/80 |
| | eat-2(ad1116) GFP::WWP-1(C762A)[r] | | 17.0 ± 0.7 | <0.0001[c] | 22 | 71/80 |
| 3b | eat-2(ad1116) | vector | 28.2 ± 0.9 | | 35 | 74/80 |
| | eat-2(ad1116) | ubc-18 dsRNA[s] | 20.5 ± 0.6 | <0.0001[e] | 25 | 78/80 |
| | eat-2(ad1116) | ubc-18 dsRNA D1 | 21.1 ± 0.7 | <0.0001[e] | 27 | 69/80 |
| 3c | isp-1(qm150) | Vector | 32.4 ± 1.2 | | 38 | 66/80 |
| | isp-1(qm150) | ubc-18 dsRNA | 31.0 ± 1.4 | 0.3882[o] | 38 | 42/80 |
| 3d | daf-2(e1368) | Vector | 33.5 ± 0.8 | | 39 | 57/80 |
| | daf-2(e1368) | ubc-18 dsRNA | 34.9 ± 1.4 | 0.0977[p] | 41 | 34/80 |
| | daf-2(e1368) | daf-16 dsRNA | 18.7 ± 0.5 | <0.0001[p] | 21 | 75/80 |
| 4c | eat-2(ad1116) | Vector | 26.2 ± 0.7 | | 30 | 90/96 |
| | eat-2(ad1116) | wwp-1 dSRNA[u] | 20.6 ± 0.5 | <0.0001[e] | 17 | 91/96 |
| | eat-2(ad1116) | ubc-18 dSRNA[v] | 19.1 ± 0.5 | <0.0001[e] | 15 | 89/96 |
| | eat-2(ad1116) | wwp-1 + ubc-18 dSRNA[w] | 19.2 ± 0.5 | <0.0001[e] 0.8732[y] | 17 | 92/96 |

TABLE 1-continued

Lifespan data for FIGS. 1-4.

| FIG. | Strain | Treatment | Mean Lifespan +/− SEM (Days) | p Value | 75th Percentile | Total Animals Died/Total |
|---|---|---|---|---|---|---|
| 4d | N2 GFP[a] | Vector | 18.7 ± 0.5 | | 21 | 72/80 |
|  | N2 GFP[a] | ubc-18 dsRNA | 18.9 ± 0.5 | 0.6335[j] | 23 | 70/80 |
|  | N2 GFP::WWP-1[k] | Vector | 23.1 ± 0.5 | <0.0001[j] | 27 | 70/80 |
|  | N2 GFP::WWP-1[k] | ubc-18 dsRNA | 19.1 ± 0.5 | 0.6772[j] 0.9020[y] | 21 | 70/80 | p values were calculated for individual experiments, each consisting of control and experimental animals examined at the same time. The 75th percentile is the age when the fraction of animals alive reaches 0.25. The total number of observations equals the number of animals that died plus the number censored. Animals that crawled off the plate, exploded, or bagged were censored at the time of event. Control and experimental animals were cultured in parallel and transferred to fresh plates at the same time. The log-rank (Mantel-Cox) test was used for statistical analysis.

[a]Transgenic worms expressing GFP under the control of the wwp-1 promoter.
[b]Transgenic worms expressing GFP-WWP-1 fusion protein under the control of the wwp-1 promoter (plotted in red in FIG. 1a).
[c]Compared to transgenic worms expressing GFP under the control of the wwp-1 promoter.
[d]Transgenic worms expressing GFP-WWP-1 fusion protein under the control of the wwp-1 promoter (plotted in pink in FIG. 1a).
[e]Compared to eat-2(ad1116) worms grown on HT115 bacteria harboring the RNAi plasmid vector.
[f]Worms fed ad libitum (AL) where the $E.\ coli$ (OP50) concentration was $7.5 \times 10^8$ cells/ml.
[g]Worms fed a restricted diet (DR) where the $E.\ coli$ (OP50) concentration was $7.5 \times 10^7$ cells/ml.
[h]Compared to N2 worms fed AL diet.
[i]Compared to wwp-1(ok1102) worms fed AL diet.
[j]Compared to transgenic worms expressing GFP under the control of the wwp-1 promoter grown on HT115 bacteria harboring the RNAi plasmid vector.
[k]Transgenic worms expressing GFP-WWP-1 fusion protein under the control of the wwp-1 promoter.
[l]Compared to transgenic worms expressing GFP under the control of the wwp-1 promoter grown on pha-4 dsRNA expressing bacteria.
[m]Compared to transgenic worms expressing GFP-WWP-1 fusion protein under the control of the wwp-1 promoter grown on HT115 bacteria harboring the RNAi plasmid vector.
[n]Compared to transgenic worms expressing GFP under the control of the wwp-1 promoter grown on daf-16 dsRNA expressing bacteria.
[o]Compared to isp-1(qm150) grown on HT115 bacteria harboring the RNAi plasmid vector.
[p]Compared to daf-2(e1368) grown on HT115 bacteria harboring the RNAi plasmid vector.
[q]Transgenic worms expressing GFP-WWP-1(C762A) fusion protein under the control of the wwp-1 promoter (plotted in red in FIG. 2b).
[r]Transgenic worms expressing GFP-WWP-1 (C762A) fusion protein under the control of the wwp-1 promoter (plotted in pink in FIG. 2b).
[s]grown on ubc-18 dsRNA expressing bacteria from hatching of eggs.
[t]grown on HT115 bacteria harboring the RNAi plasmid vector from hatching of eggs. At Day 1 adulthood worms were switched to plates with bacteria expressing ubc-18 dsRNA.
[u]Worms grown on HT115 bacteria harboring the RNAi plasmid vector and wwp-1 RNAi vector.
[v]Worms grown on bacteria harboring the RNAi plasmid vector and ubc-18 RNAi vector.
[w]Worms grown on bacteria harboring the wwp-1 and ubc-18 RNAi vectors.
[x]Compared to worms grown on bacteria harboring the RNAi plasmid vector and ubc-18 RNAi vector.
[y]Compared to transgenic worms expressing GFP under the control of the wwp-1 promoter grown on ubc-18 dsRNA expressing bacteria.

TABLE 2

Effects of Dietary Restriction on Lifespan (FIG. 1d).

| Strain | bacterial conc. ($10^8$ cells/ml) | Mean Lifespan +/− SEM (Days) | p Value[a] | 75th Percentile | Total Animals Died/Total |
|---|---|---|---|---|---|
| N2 | 0.05 | 43.7 ± 1.9 | <0.0001 | 53 | 36/40 |
| N2 | 0.25 | 59.5 ± 1.9 | <0.0001 | 69 | 39/40 |
| N2 | 0.75 | 55.2 ± 3.0 | <0.0001 | 66 | 35/40 |
| N2 | 1.5 | 34.3 ± 2.3 | <0.0001 | 46 | 38/40 |
| N2 | 7.5 | 18.2 ± 1.4 | | 25 | 38/41 |
| N2 | 15 | 14.9 ± 1.0 | 0.0394 | 22 | 39/40 |
| wwp-1(ok1102) | 0.05 | 15.7 ± 1.1 | 0.1059 | 22 | 39/40 |
| wwp-1(ok1102) | 0.25 | 19.6 ± 1.3 | 0.6916 | 25 | 37/40 |
| wwp-1(ok1102) | 0.75 | 20.9 ± 1.6 | 0.1236 | 29 | 40/40 |
| wwp-1(ok1102) | 1.5 | 18.8 ± 1.7 | 0.6061 | 25 | 31/40 |
| wwp-1(ok1102) | 7.5 | 13.9 ± 0.9 | 0.0072 | 18 | 38/40 |
| wwp-1(ok1102) | 15 | 16.5 ± 0.6 | 0.1203 | 18 | 39/40 |

[a]Compared to N2 worms fed AL ($7.5 \times 10^8$ cells/ml).

TABLE 3

Lifespan data for FIGS. 8-10 and 12.

| FIG. | Strain | Treatment | Mean Lifespan +/− SEM (Days) | p Value | 75th Percentile | Total Animals Died/Total |
|---|---|---|---|---|---|---|
| 9a | N2 (25° C.) | Vector | 11.8 ± 0.4 | | 15 | 76/80 |
|  | N2 (25° C.) | wwp-1 dsRNA | 10.1 ± 0.3 | 0.0002[a] | 12 | 78/80 |
| 9b | N2 | 25° C. | 10.6 ± 0.4 | | 13 | 75/80 |
|  | wwp-1(ok1102) | 25° C. | 9.4 ± 0.3 | 0.0063[b] | 11 | 72/80 |
| 8a | N2 | Vector | 17.2 ± 0.5 | | 21 | 71/80 |
|  | N2 | wwp-1 dsRNA | 17.5 ± 0.5 | 0.5789[a] | 21 | 71/80 |

TABLE 3-continued

Lifespan data for FIGS. 8-10 and 12.

| FIG. | Strain | Treatment | Mean Lifespan +/− SEM (Days) | p Value | 75th Percentile | Total Animals Died/Total |
|---|---|---|---|---|---|---|
| 8b | N2 | | 17.2 ± 0.4 | | 19 | 76/80 |
| | wwp-1(ok1102) | | 16.9 ± 0.3 | 0.9725[b] | 18 | 77/80 |
| 8c | N2 | Vector | 18.8 ± 0.7 | | 24 | 74/80 |
| | N2 | ubc-18 dsRNA | 18.9 ± 0.7 | 0.9469[a] | 24 | 68/80 |
| 10a | daf-2(e1370) | Vector | 42.8 ± 1.1 | | 48 | 70/80 |
| | daf-2(e1370) | wwp-1 dsRNA | 38.6 ± 0.9 | 0.0011[c] | 43 | 60/72 |
| | daf-2(e1370) | daf-16 dsRNA | 19.3 ± 0.6 | <0.0001[c] | 23 | 64/80 |
| 10b | daf-2(e1370) | Vector | 44.7 ± 1.0 | | 50 | 69/80 |
| | daf-2(e1370) | ubc-18 dsRNA | 40.1 ± 0.9 | 0.0002[c] | 46 | 84/120 |
| | daf-2(e1370) | daf-16 dsRNA | 19.3 ± 0.6 | <0.0001[c] | 23 | 58/80 |
| 12 | eat-2(ad1116) | Vector | 26.6 ± 0.8 | | 33 | 71/80 |
| | eat-2(ad1116) | f56d2.2 dsRNA | 25.9 ± 0.9 | 0.7535[a] | 33 | 77/80 |
| | eat-2(ad1116) | ari-1 dsRNA | 25.6 ± 0.9 | 0.6258[a] | 30 | 69/80 |

[a]Compared to N2 worms grown on HT115 bacteria harboring the RNAi plasmid vector.
[b]Compared to N2 worms grown on OP50 bacteria.
[c]Compared to daf-2(e1370) worms grown on HT115 bacteria harboring the RNAi plasmid vector.

TABLE 4

Lifespan data for FIGS. 12-15 and 18-19.

| FIG. | Strain | Treatment | Mean Lifespan +/− SEM (Days) | p Value | 75th Percentile | Total Animals Died/Total |
|---|---|---|---|---|---|---|
| 12 | eat-2(ad1116) | Vector | 26.6 ± 0.8 | | 33 | 71/80 |
| | eat-2(ad1116) | ari-1 dsRNA | 25.6 ± 0.9 | 0.6258[a] | 30 | 69/80 |
| | eat-2(ad1116) | f56d2.2 dsRNA | 25.9 ± 0.9 | 0.7535[a] | 33 | 77/80 |
| 13A | GFP[b] | | 17.3 ± 0.4 | | 19 | 75/96 |
| | UBC-18::GFP[c] | | 16.1 ± 0.4 | 0.0115[d] | 17 | 75/96 |
| | UBC-18::GFP[e] | | 16.7 ± 0.5 | 0.6828[d] | 19 | 80/96 |
| 13B | GFP[b] | | 17.0 ± 0.4 | | 19 | 79/96 |
| | UBC-18[f] | | 16.3 ± 0.5 | 0.3160[d] | 19 | 46/76 |
| | UBC-18[g] | | 17.7 ± 0.5 | 0.2868[d] | 19 | 70/96 |
| | UBC-18[h] | | 17.0 ± 0.2 | 0.9075[d] | 19 | 73/96 |
| 14 | N2 | | 19.1 ± 0.5 | | 23 | 69/80 |
| | ubc-18(ku354) | | 17.1 ± 0.6 | 0.0237[i] | 21 | 52/80 |
| 15A | clk-1(qm30) | Vector | 26.5 ± 0.7 | | 32 | 69/80 |
| | clk-1(qm30) | wwp-1 dsRNA | 23.9 ± 0.4 | <0.0001[j] | 26 | 72/80 |
| | clk-1(qm30) | ubc-18 dsRNA | 25.0 ± 0.5 | 0.0034[j] | 28 | 64/80 |
| 15B | N2 | cyc-1 dsRNA | 29.3 ± 0.7 | | 35 | 76/80 |
| | wwp-1(ok1102) | cyc-1 dsRNA | 24.0 ± 0.7 | <0.0001[k] | 28 | 78/80 |
| 18A | wwp-1(ok1102) | Vector | 16.9 ± 0.3 | | 18 | 77/80 |
| | wwp-1(ok1102) | rab-10 dsRNA | 15.6 ± 0.3 | 0.0026[m] | 18 | 76/80 |
| 18B | N2 | Vector + rab-10 dsRNA | 24.2 ± 0.9 | | 29 | 41/80 |
| | N2 | wwp-1 + rab-10 dsRNA | 15.7 ± 0.6 | <0.0001[l] | 19 | 64/80 |
| 19A | N2 | rab-10 dsRNA | 23.1 ± 0.7 | | 26 | 65/80 |
| | ubc-18(ku354) | rab-10 dsRNA | 12.5 ± 0.6 | <0.0001[l] | 13 | 39/80 |
| 19B | N2 | Vector + rab-10 dsRNA | 24.0 ± 0.7 | | 29 | 71/80 |
| | N2 | ubc-18 + rab-10 dsRNA | 20.8 ± 0.5 | 0.0001[l] | 24 | 69/80 |

[a]Compared to eat-2(ad1116) worms grown on HT115 bacteria harboring the RNAi plasmid vector.
[b]Transgenic worms expressing GFP under the control of the ubc-18 promoter.
[c]Transgenic worms expressing GFP-UBC-18 fusion protein under the control of the ubc-18 promoter (plotted in red in FIG. 13 Panel A).
[d]Compared to transgenic worms expressing GFP under the control of the ubc-18 promoter.
[e]Transgenic worms expressing GFP-UBC-18 fusion protein under the control of the ubc-18 promoter (plotted in pink in FIG. 13 Panel A).
[f]Transgenic worms expressing UBC-18 under the control of the ubc-18 promoter (plotted in red in FIG. 13 Panel B).
[g]Transgenic worms expressing UBC-18 under the control of the ubc-18 promoter (plotted in pink in FIG. 13 Panel B).
[h]Transgenic worms expressing UBC-18 under the control of the ubc-18 promoter (plotted in yellow in FIG. 13 Panel B).
[i]Compared to N2 worms grown on HT115 bacteria harboring the RNAi plasmid vector.
[j]Compared to clk-1(qm30) worms grown on HT115 bacteria harboring the RNAi plasmid vector.
[k]Compared to N2 worms grown on HT115 bacteria expressing cyc-1 dsRNA.
[l]Compared to N2 worms grown on HT115 bacteria harboring the RNAi plasmid vector and HT115 bacteria expressing rab-10 RNAi.
[m]Compared to wwp-1(ok1102) worms grown on HT115 bacteria harboring the RNAi plasmid vector.
[n]Compared to N2 worms grown on HT115 bacteria expressing rab-10 dsRNA.

TABLE 5

Effects of solid plate dietary restriction on lifespan (FIG. 17).

| Strain | bacterial conc. (cells/ml) | Mean Lifespan +/− SEM (Days) | p Value[a] | 75th Percentile | Total Animals Died/Total |
|---|---|---|---|---|---|
| N2 | $5 \times 10^{10}$ | 18.5 ± 0.8 | | 25 | 64/65 |
| N2 | $5 \times 10^{9}$ | 21.3 ± 0.8 | 0.0134 | 26 | 59/65 |
| N2 | $5 \times 10^{8}$ | 21.9 ± 0.8 | 0.0063 | 26 | 60/66 |
| N2 | $5 \times 10^{7}$ | 23.6 ± 1.0 | <0.0001 | 28 | 64/65 |
| wwp-1(ok1102) | $5 \times 10^{10}$ | 16.9 ± 0.6 | 0.0590 | 22 | 63/66 |
| wwp-1(ok1102) | $5 \times 10^{9}$ | 18.1 ± 0.6 | 0.4110 | 22 | 59/65 |
| wwp-1(ok1102) | $5 \times 10^{8}$ | 17.8 ± 0.6 | 0.2875 | 19 | 58/68 |
| wwp-1(ok1102) | $5 \times 10^{7}$ | 17.4 ± 0.7 | 0.3283 | 19 | 50/65 |

[a]Compared to N2 worms fed AL ($5 \times 10^{10}$ cells/ml).

REFERENCES

1. Pickart, C. M. Mechanisms underlying ubiquitination. *Annu Rev Biochem* 70, 503-33 (2001).
2. Weissman, A. M. Themes and variations on ubiquitylation. *Nat Rev Mol Cell Biol* 2, 169-78 (2001).
3. Verdecia, M. A. et al. Conformational Flexibility Underlies Ubiquitin Ligation Mediated by the WWP1 HECT Domain E3 Ligase. *Mol Cell* 11, 249-59 (2003).
4. Huang, L. et al. Structure of an E6AP-UbCH7 complex: insights into ubiquitination by the E2-E3 enzyme cascade. *Science* 286, 1321-6 (1999).
5. Pirozzi, G. et al. Identification of novel human WW domain-containing proteins by cloning of ligand targets. *J Biol Chem* 272, 14611-6 (1997).
6. Huang, K. et al. A HECT domain ubiquitin ligase closely related to the mammalian protein WWP1 is essential for *Caenorhabditis elegans* embryogenesis. *Gene* 252, 137-45 (2000).
7. Blumenthal, T. & Spieth, J. Gene structure and organization in *Caenorhabditis elegans*. *Curr Opin Genet Dev* 6, 692-8 (1996).
8. Blumenthal, T. et al. A global analysis of *Caenorhabditis elegans* operons. *Nature* 417, 851-4 (2002).
9. Sieburth, D. et al. Systematic analysis of genes required for synapse structure and function. *Nature* 436, 510-7 (2005).
10. Wolkow, C. A., Kimura, K. D., Lee, M. S. & Ruvkun, G. Regulation of *C. elegans* life-span by insulinlike signaling in the nervous system. *Science* 290, 147-50 (2000).
11. Apfeld, J. & Kenyon, C. Regulation of lifespan by sensory perception in *Caenorhabditis elegans*. *Nature* 402, 804-9 (1999).
12. Parkes, T. L. et al. Extension of *Drosophila* lifespan by overexpression of human SOD1 in motomeurons. *Nat Genet.* 19, 171-4 (1998).
13. Wang, M. C., Bohmann, D. & Jasper, H. JNK signaling confers tolerance to oxidative stress and extends lifespan in *Drosophila*. *Dev Cell* 5, 811-6 (2003).
14. Alcedo, J. & Kenyon, C. Regulation of *C. elegans* longevity by specific gustatory and olfactory neurons. *Neuron* 41, 45-55 (2004).
15. Lakowski, B. & Hekimi, S. The genetics of caloric restriction in *Caenorhabditis elegans*. *Proc Natl Acad Sci USA* 95, 13091-6 (1998).
16. Rogina, B. & Helfand, S. L. Sir2 mediates longevity in the fly through a pathway related to calorie restriction. *Proc Natl Acad Sci USA* 101, 15998-6003 (2004).
17. Tissenbaum, H. A. & Guarente, L. Increased dosage of a sir-2 gene extends lifespan in *Caenorhabditis elegans*. *Nature* 410, 227-30 (2001).
18. Klass, M. R. Aging in the nematode *Caenorhabditis elegans*: major biological and environmental factors influencing life span. *Mech Ageing Dev* 6, 413-29 (1977).
19. Panowski, S. H., Wolff, S., Aguilaniu, H., Durieux, J. & Dillin, A. PHA-4/Foxa mediates diet-restriction-induced longevity of *C. elegans*. *Nature* 447, 550-5 (2007).
20. Lin, K., Hsin, H., Libina, N. & Kenyon, C. Regulation of the *Caenorhabditis elegans* longevity protein DAF-16 by insulin/IGF-1 and germline signaling. *Nat Genet.* 28, 139-45 (2001).
21. Ogg, S. et al. The Fork head transcription factor DAF-16 transduces insulin-like metabolic and longevity signals in *C. elegans*. *Nature* 389, 994-999 (1997).
22. Dillin, A. et al. Rates of behavior and aging specified by mitochondrial function during development. *Science* 298, 2398-401 (2002).
23. Feng, J., Bussiere, F. & Hekimi, S. Mitochondrial electron transport is a key determinant of life span in *Caenorhabditis elegans*. *Dev Cell* 1:633-644 (2001).
24. Lee, S. S. et al. A systematic RNAi screen identifies a critical role for mitochondria in *C. elegans* longevity. *Nat. Genet.* 33, 40-48 (2003).
25. Kimura, K. D., Tissenbaum, H. A., Liu, Y. & Ruvkun, G. daf-2, an insulin receptor-like gene that regulates longevity and diapause in *Caenorhabditis elegans*. *Science* 277, 942-946 (1997).
26. Hoppe, T. et al. Activation of a membrane-bound transcription factor by regulated ubiquitin/proteasome-dependent processing. *Cell* 102, 577-86 (2000).
27. Qiu, X. & Fay, D. S. ARI-1, an RBR family ubiquitin-ligase, functions with UBC-18 to regulate pharyngeal development in *C. elegans*. *Dev Biol* 291, 239-52 (2006).
28. Fay, D. S. et al. The coordinate regulation of pharyngeal development in *C. elegans* by lin-35/Rb, pha-1, and ubc-18. *Dev Biol* 271, 11-25 (2004).
29. Fay, D. S., Large, E., Han, M. & Darland, M. lin-35/Rb and ubc-18, an E2 ubiquitin-conjugating enzyme, function redundantly to control pharyngeal morphogenesis in *C. elegans*. *Development* 130, 3319-30 (2003).
30. Brenner, S. The genetics of *Caenorhabditis elegans*. *Genetics* 77, 71-94 (1974).
31. Dillin, A., Crawford, D. K. & Kenyon, C. Timing requirements for insulin/IGF-1 signaling in *C. elegans*. *Science* 298, 830-4 (2002).
32. Wolff, S. et al. SMK-1, an essential regulator of DAF-16-mediated longevity. *Cell* 124, 1039-53 (2006).
33. Mello, C. C., Kramer, J. M., Stinchcomb, D. & Ambros, V. Efficient gene transfer in *C. elegans*: extrachromosomal maintenance and integration of transforming sequences. *Embo J* 10, 3959-70 (1991).
34. Leverson, J. D. et al. The APC11 RING-H2 finger mediates E2-dependent ubiquitination. *Mol Biol Cell* 11, 2315-25 (2000).
35. Xia, Y., Pao, G. M., Chen, H. W., Verma, I. M. & Hunter, T. Enhancement of BRCA1 E3 ubiquitin ligase activity through direct interaction with the BARD1 protein. *J Biol Chem* 278, 5244-63 (2003).
36. Carrano, A. C., Eytan, E., Hershko, A. & Pagano, M. SKP2 is required for ubiquitin-mediated degradation of the CDK inhibitor p27.PG-193-9. *Nat Cell Biol* 1 (1999).
37. Hope, I. *C. elegans*: A practical approach Oxford (Oxford University Press, 1999).
38. Bishop, N. A. & Guarente, L. Two neurons mediate diet-restriction-induced longevity in *C. elegans*. *Nature* 447, 545-9 (2007).

39. Mosser, E. A. et al. Physical and functional interactions between the transactivation domain of the hematopoietic transcription factor NF-E2 and WW domains. Biochemistry 37, 13686-95 (1998).
40. Conkright, M. D., Wani, M. A. & Lingrel, J. B. Lung Kruppel-like factor contains an autoinhibitory domain that regulates its transcriptional activation by binding WWP1, an E3 ubiquitin ligase. J Biol Chem 276, 29299-306 (2001).
41. Zhang, X., Srinivasan, S. V. & Lingrel, J. B. WWP1-dependent ubiquitination and degradation of the lung Kruppel-like factor KLF2. Biochem Biophys Res Commun 316, 139-48 (2004).
42. Jones, D. C. et al. Regulation of adult bone mass by the zinc finger adapter protein Schnurri-3. Science 312, 1223-7 (2006).
43. Chen, C. et al. Human Kruppel-like factor 5 is a target of the E3 ubiquitin ligase WWP1 for proteolysis in epithelial cells. J Biol Chem 280, 41553-61 (2005).
44. Laine, A. & Ronai, Z. Regulation of p53 localization and transcription by the HECT domain E3 ligase WWP1. Oncogene (2006).
45. Ikeda, M., Ikeda, A., Longan, L. C. & Longnecker, R. The Epstein-Barr virus latent membrane protein 2A PY motif recruits WW domain-containing ubiquitin-protein ligases. Virology 268, 178-91 (2000).
46. Xu, H. M. et al. WWP2, an E3 ubiquitin ligase that targets transcription factor Oct-4 for ubiquitination. J Biol Chem 279, 23495-503 (2004).
47. Fang, D. et al. Dysregulation of T lymphocyte function in itchy mice: a role for Itch in TH2 differentiation. Nat Immunol 3, 281-7 (2002).
48. Qiu, L. et al. Recognition and ubiquitination of Notch by Itch, a hect-type E3 ubiquitin ligase. J Biol Chem 275, 35734-7 (2000).
49. Traweger, A. et al. The tight junction-specific protein occludin is a functional target of the E3 ubiquitin-protein ligase itch. J Biol Chem 277, 10201-8 (2002).
50. Gao, M. et al. Jun turnover is controlled through JNK-dependent phosphorylation of the E3 ligase Itch. Science 306, 271-5 (2004).
51. Rossi, M. et al. The ubiquitin-protein ligase Itch regulates p73 stability. EMBO J. 24, 836-848 (2005).
52. Rossi, M. et al. The E3 ubiquitin ligase Itch controls the protein stability of p63. Proc Natl Acad Sci USA 103, 12753-8 (2006).
53. Rossi, M. et al. Itch/AIP4 associates with and promotes p63 protein degradation. Cell Cycle 5, 1816-22 (2006).
54. Feng, L., Guedes, S. & Wang, T. Atrophin-1-interacting protein 4/human Itch is a ubiquitin E3 ligase for human enhancer of filamentation 1 in transforming growth factor-beta signaling pathways. J Biol Chem 279, 29681-90 (2004).
55. Lallemand, F. et al. AIP4 restricts transforming growth factor-beta signaling through a ubiquitination-independent mechanism. J Biol Chem 280, 27645-53 (2005).
56. Ingham, R. J. et al. The Epstein-Barr virus protein, latent membrane protein 2A, co-opts tyrosine kinases used by the T cell receptor. J Biol Chem 280, 34133-42 (2005).
57. Angers, A., Ramjaun, A. R. & McPherson, P. S. The HECT domain ligase itch ubiquitinates endophilin and localizes to the trans-Golgi network and endosomal system. J Biol Chem 279, 11471-9 (2004).
58. Laine, A., & Ronai, Z. Regulation of p53 localization and transcription by the HECT domain E3 ligase WWP1. Oncogene 26, 1477-1483 (2007).
59. Bernassola, F. et al. The HECT family of E3 ubiquitin ligases: Multiple players in cancer development. Cancer Cell 14, 10-21 (2008).
60. Arum, O. & Johnson, T. E. Reduced expression of the *Caenorhabditis elegans* p53 ortholog cep-1 results in increased longevity. J Gerontol A Biol Sci Med. Sci. 62, 951-9 (2007).
61. Greer, E. L. et al. An AMPK-FOXO pathway mediates longevity induced by a novel method of dietary restriction in *C. elegans*. Curr Biol 17, 1646-1656 (2007).
62. Bauer et al. Neuronal expression of p53 dominant-negative proteins in adult *Drosophila melanogaster* extends life span. Curr Biol 15, 2063-2068 (2005).

Example 2

WWP-1 and UBC-18 Regulate Dietary Restriction-Induced Autophagy Involved in Lifespan Extension Autophagy is an important eukaryotic response to cellular stress/nutrient limitation. In this process, portions of the cytoplasm and cytoplasmic organelles are degraded, allowing cellular macromolecules to be catabolized and recycled. Large double-membrane vesicles (autophagosomes) are generated and, along with their contents, degraded in lysosomes. The process of autophagy allows an animal to recycle macromolecules during times of starvation and stress to deploy scarce resources in a more beneficial fashion.

How autophagy is regulated has been studied extensively in yeast. Autophagy in yeast is controlled by ATG (autophagy regulated genes), most of which are highly conserved and have functional homologs in higher organisms. Briefly, TOR (Target Of Rapamycin) inhibits the protein kinase ATG1, which would otherwise mediate an early activation step in the autophagic process. In response to ATG1 activity, the VPS34-Beclin1 complex stimulates the formation of autophagosomes.

Autophagy undergoes a steady loss of function with age. Inefficient autophagy results in buildup of damaged cellular components and may lead to disease. Restricted food supply speeds up autophagy; thus, dietary restriction may offset the natural age-related decline of autophagy. Recently it has been shown in *C. elegans* that dietary restriction produces an autophagic response and that inhibiting genes required for autophagy prevents DR from extending lifespan (Hansen et al. (2008) "A role for autophagy in the extension of lifespan by dietary restriction in *C. elegans*" PLoS Genetics e24).

As in yeast, autophagy pathway genes in *C. elegans* include TOR, ATG6/beclin1/bec-1/vps-30, and vps-34. The foxa transcription factor pha-4 is also involved in dietary restriction-induced autophagy in *C. elegans* (Hansen et al. (2008) supra), as is rab-10.

The small GTPase rab-10 has previously been shown to be involved in the longevity response to dietary restriction in *C. elegans* (Hansen et al. (2005) "New genes tied to endocrine, metabolic, and dietary regulation of lifespan from a *Caenorhabditis elegans* genomic RNAi screen" PLoS Genetics e17). Similar to TOR inhibition, rab-10 inhibition extends the lifespan of animals fed ad libitum, but does not further extend the lifespan of animals subjected to dietary restriction (Hansen et al. (2005) supra). Recently it has been shown that rab-10 inhibition triggers autophagy (Hansen et al. (2008) supra). We show that loss of wwp-1 and ubc-18 significantly shortened the extended lifespan of animals fed bacteria expressing rab-10 dsRNA (FIG. 18 Panels A-B and FIG. 19 Panels A-B for wwp-1 and ubc-18, respectively). Our results suggest that both wwp-1 and ubc-18 are essential for the extended longevity of animals with loss of expression of rab-10 by RNAi.

rab-10 mRNA levels fall with DR, and RNAi to rab-10 increases lifespan. Since loss of wwp-1 suppresses the lifespan extension otherwise seen with knockdown of rab-10, in one model (without limitation) wwp-1 is downstream of this event. In another model (again without limitation), rab-10 and wwp-1 act in parallel autophagy pathways regulating longevity.

The results presented in this example indicate that wwp-1 and ubc-18 are part of the mechanism by which dietary restriction stimulates autophagy and regulates longevity. The results provide further support for the relevance of wwp-1 and ubc-18 and the ubiquitin pathway in identification of novel modulators of longevity, and further suggest autophagy pathway parameters as useful parameters to monitor in screens for such modulators.

While the foregoing invention has been described in some detail for purposes of clarity and understanding, it will be clear to one skilled in the art from a reading of this disclosure that various changes in form and detail can be made without departing from the true scope of the invention. For example, all the techniques and apparatus described above can be used in various combinations. All publications, patents, patent applications, and/or other documents cited in this application are incorporated by reference in their entirety for all purposes to the same extent as if each individual publication, patent, patent application, and/or other document were individually indicated to be incorporated by reference for all purposes.

What is claimed is:

1. A method of identifying a modulator of longevity, the method comprising:
providing a C. elegans animal;
administering a test compound to the C. elegans animal; and
monitoring expression or activity of a C. elegans wwp-1 E3 ubiquitin ligase or a homolog thereof, expression or activity of a C. elegans ubc-18 E2 ubiquitin conjugation enzyme or a homolog thereof, and/or post-translational modification state of a C. elegans wwp-1 E3 ubiquitin ligase or a homolog thereof or a substrate thereof in the animal, wherein an increase in expression or activity of the C. elegans wwp-1 or the homolog thereof, an increase in expression or activity of the C. elegans ubc-18 or the homolog thereof, increased phosphorylation of the C. elegans wwp-1 or the homolog thereof, and/or increased ubiquitination of the substrate indicates that the test compound modulates longevity.

2. The method of claim 1, wherein the C. elegans animal expresses a fusion protein comprising GFP or a homolog thereof and either a C. elegans wwp-1 or a homolog thereof or a C. elegans ubc-18 or a homolog thereof, wherein monitoring expression of the C. elegans wwp-1 or ubc-18 or the homolog thereof comprises monitoring an optical signal from the GFP.

3. A method of identifying a modulator of longevity, the method comprising:
providing an isolated cell;
contacting the cell with a test compound; and
monitoring expression or activity of a C. elegans wwp-1 E3 ubiquitin ligase or a homolog thereof, expression or activity of a C. elegans ubc-18 E2 ubiquitin conjugation enzyme or a homolog thereof, and/or post-translational modification state of a C. elegans wwp-1 E3 ubiquitin ligase or a homolog thereof or a substrate thereof in the cell, wherein an increase in expression or activity of the C. elegans wwp-1 or the homolog thereof, an increase in expression or activity of the C. elegans ubc-18 or the homolog thereof, increased phosphorylation of the C. elegans wwp-1 or the homolog thereof, and/or increased ubiquitination of the substrate indicates that the test compound modulates longevity.

4. The method of claim 3, wherein the cell expresses a fusion protein comprising GFP or a homolog thereof and either a C. elegans wwp-1 or a homolog thereof or a C. elegans ubc-18 or a homolog thereof, wherein monitoring expression of the C. elegans wwp-1 or ubc-18 or the homolog thereof comprises monitoring an optical signal from the GFP.

5. The method of claim 1, wherein the C elegans animal is dietary-restricted.

6. The method of claim 1, wherein the C. elegans wwp-1 homolog is selected from Drosophila and mammalian homologs.

7. The method of claim 1, wherein the C. elegans wwp-1 homolog comprises an amino acid sequence at least 90% identical to the amino acid sequence depicted in SEQ ID NO: 9.

8. The method of claim 1, wherein the C. elegans wwp-1 comprises the amino acid sequence depicted in SEQ ID NO: 9.

9. The method of claim 1, wherein the C. elegans ubc-18 homolog is selected from Drosophila and mammalian homologs.

10. The method of claim 1, wherein the C. elegans ubc-18 homolog comprises an amino acid sequence at least 90% identical to the amino acid sequence depicted in SEQ ID NO: 11.

11. The method of claim 1, wherein the C. elegans ubc-18 comprises the amino acid sequence depicted in SEQ ID NO: 11.

12. The method of claim 1, wherein the C. elegans animal exhibits increased phosphorylation of the C. elegans wwp-1 or the homolog thereof, and/or increased ubiquitination of the substrate.

13. The method of claim 5, wherein the dietary-restricted C. elegans animal exhibits reduced expression or activity of the C. elegans wwp-1 or the homolog thereof and/or reduced expression or activity of the C. elegans ubc-18 or the homolog thereof.

14. The method of claim 5, wherein the dietary-restricted C. elegans animal expresses a dominant negative of the C. elegans wwp-1 or the homolog thereof or a dominant negative form of the C. elegans ubc-18 or the homolog thereof.

15. The method of claim 1, wherein the C. elegans animal overexpresses C. elegans wwp-1 or the homolog thereof.

16. The method of claim 1, wherein the test compound is selected from the group consisting of: a small molecule, a polypeptide, an antibody, a nucleic acid, an antisense molecule, and a double-stranded RNA.

17. The method of claim 1, wherein the C. elegans wwp-1 homolog is encoded by a nucleic acid sequence at least 90% identical to the nucleic acid sequence depicted in SEQ ID NO: 10.

18. The method of claim 1, wherein the C. elegans ubc-18 homolog is encoded by a nucleic acid sequence at least 90% identical to the nucleic acid sequence depicted in SEQ ID NO: 12.

* * * * *